(12) United States Patent
Lin et al.

(10) Patent No.: US 10,340,466 B2
(45) Date of Patent: Jul. 2, 2019

(54) ORGANIC METAL COMPOUND, ORGANIC LIGHT-EMITTING DEVICES EMPLOYING THE SAME

(71) Applicant: INDUSTRIAL TECHNOLOGY RESEARCH INSTITUTE, Hsinchu (TW)

(72) Inventors: Jin-Sheng Lin, Taipei (TW); Yung-Chen Cheng, Changhua (TW); Jia-Lun Liou, Hengshan Township (TW); Pang-Chi Huang, Taoyuan (TW); Cheng-An Wu, New Taipei (TW); Meng-Hao Chang, New Taipei (TW); Bing-Huang Jiang, New Taipei (TW); Han-Cheng Yeh, Taipei (TW); Chun-Neng Ku, Tainan (TW); Mei-Rurng Tseng, Hsinchu (TW); Jung-Yu Liao, Hsinchu County (TW); Jui-Chih Kao, Taoyuan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 298 days.

(21) Appl. No.: 15/361,239

(22) Filed: Nov. 25, 2016

(65) Prior Publication Data
US 2017/0155065 A1    Jun. 1, 2017

(30) Foreign Application Priority Data

Nov. 26, 2015 (TW) .............................. 104139355 A
Nov. 7, 2016  (TW) .............................. 105136104 A

(51) Int. Cl.
*H01L 51/00* (2006.01)
*H01L 51/50* (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
CPC .............. C09K 11/06; C09K 2211/185; C09K 2211/1029; H01L 51/0085; H01L 51/5016;
(Continued)

(56) References Cited

U.S. PATENT DOCUMENTS 6,277,860 B1   8/2001  Sugie et al.
7,067,515 B2   6/2006  Wishka et al.
(Continued)

FOREIGN PATENT DOCUMENTS

CN   102911211 A   2/2013
CN   102952162 A   3/2013
(Continued)

OTHER PUBLICATIONS

U.S. Office Action for U.S. Appl. No. 14/972,716 dated Jun. 26, 2017.
(Continued)

*Primary Examiner* — Amanda C. Walke
(74) *Attorney, Agent, or Firm* — Birch, Stewart, Kolasch & Birch, LLP

(57) ABSTRACT

Organic metal compounds, and organic light-emitting devices employing the same are provided. The organic metal compound has a chemical structure represented by Formula (I) or Formula (II):

(Continued)

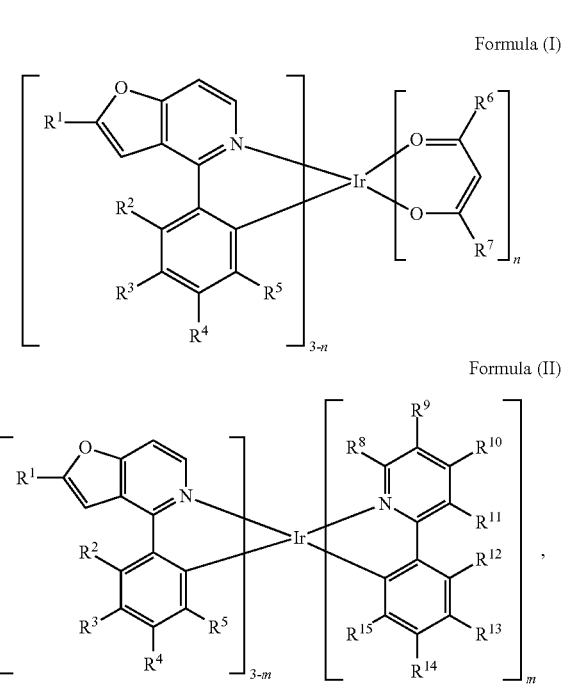

Formula (I)

Formula (II)

wherein, $R^1$ is hydrogen, $C_{1-12}$ alkyl, $C_{1-12}$ alkoxy, amine, $C_{2-6}$ alkenyl, $C_{2-6}$ alkynyl, $C_{5-10}$ cycloalkyl, $C_{3-12}$ heteroaryl, or $C_{6-12}$ aryl; $R^2$, $R^3$, $R^4$, and $R^5$ can be hydrogen, halogen, $C_{1-12}$ alkyl, $C_{1-12}$ alkoxy, $C_{1-12}$ fluoroalkyl; $R^6$ and $R^7$ are independent and can be $C_{1-6}$ alkyl, or phenyl; $R^8$, $R^9$, $R^{10}$, $R^{11}$, $R^{12}$, $R^{13}$, $R^{14}$, and $R^{15}$ can be hydrogen, halogen, $C_{1-12}$ alkyl, $C_{1-12}$ fluoroalkyl, or two adjacent groups of $R^2$, $R^3$, $R^4$, $R^5$, $R^8$, $R^9$, $R^{10}$, $R^{11}$, $R^{12}$, $R^{13}$, $R^{14}$ and $R^{15}$ are optionally combined with the carbon atoms which they are attached to, to form a cycloalkyl group, or aryl; m is 1 or 2; and, n is 0 or 1.

20 Claims, 1 Drawing Sheet

(51) Int. Cl.
C07F 15/00 (2006.01)
C09K 11/06 (2006.01)

(52) U.S. Cl.
CPC ...... *H01L 51/0071* (2013.01); *H01L 51/5012* (2013.01); *C09K 2211/1007* (2013.01); *C09K 2211/1011* (2013.01); *C09K 2211/1033* (2013.01); *C09K 2211/185* (2013.01); *H01L 51/5016* (2013.01)

(58) Field of Classification Search
CPC .............. H01L 51/5012; H01L 51/0071; C07F 51/0033
USPC ................ 428/690; 546/4, 10; 257/E51.026, 257/E51.041; 252/301.16
See application file for complete search history.

(56) References Cited

U.S. PATENT DOCUMENTS

| | | | |
|---|---|---|---|
| 7,445,857 B2 | 11/2008 | Shen et al. | |
| 7,592,352 B2 | 9/2009 | Miyazaki | |
| 7,799,775 B2 | 9/2010 | Sato et al. | |
| 7,943,634 B2 | 5/2011 | Gharat et al. | |
| 8,598,156 B2 | 12/2013 | Axten et al. | |
| 9,634,264 B2 | 4/2017 | Beers et al. | |
| 2007/0237891 A1 | 10/2007 | Sugiura et al. | |
| 2007/0237981 A1 | 10/2007 | Shen et al. | |
| 2008/0085886 A1 | 4/2008 | Savy et al. | |
| 2010/0261736 A1 | 10/2010 | Lampe et al. | |
| 2010/0295032 A1 | 11/2010 | Kwong et al. | |
| 2011/0284799 A1 | 11/2011 | Stoessel et al. | |
| 2011/0285275 A1 | 11/2011 | Huang et al. | |
| 2012/0061654 A1 | 3/2012 | Rayabarapu et al. | |
| 2012/0119190 A1 | 5/2012 | Alleyne et al. | |
| 2012/0181511 A1 | 7/2012 | Ma et al. | |
| 2012/0184743 A1 | 7/2012 | Watanabe et al. | |
| 2012/0217868 A1 | 8/2012 | Ma et al. | |
| 2012/0309739 A1 | 12/2012 | Bell et al. | |
| 2013/0033171 A1 | 2/2013 | Huang et al. | |
| 2013/0116755 A1 | 5/2013 | Anemian et al. | |
| 2014/0350642 A1 | 11/2014 | Anemian et al. | |
| 2015/0001472 A1 | 1/2015 | Boudreault et al. | |
| 2015/0090974 A1 | 4/2015 | Kim et al. | |
| 2015/0097169 A1 | 4/2015 | Xia et al. | |
| 2015/0105843 A1 | 4/2015 | Heun et al. | |
| 2015/0188059 A1 | 7/2015 | Chao et al. | |
| 2017/0155063 A1* | 6/2017 | Wu ..................... H01L 51/0085 |

FOREIGN PATENT DOCUMENTS

| | | |
|---|---|---|
| CN | 103002949 A | 3/2013 |
| CN | 104744517 A | 7/2015 |
| CN | 105505378 A | 4/2016 |
| EP | 2 730 583 A1 | 5/2014 |
| JP | 2012-522844 A | 9/2012 |
| JP | 2013-526773 A | 6/2013 |
| JP | 2013-537519 A | 10/2013 |
| JP | 2014-94941 A | 5/2014 |
| TW | 200623955 A | 7/2006 |
| TW | 201100432 A1 | 1/2011 |
| TW | 201224114 A1 | 6/2012 |
| TW | I395804 B1 | 5/2013 |
| TW | I429652 B | 3/2014 |
| TW | 201446775 A | 12/2014 |

OTHER PUBLICATIONS

Japanese Office Action for Appl. No. 2016-229364 dated Jan. 16, 2018 (w/ English translation).
Extended European Search Report for Appl. No. 16200901.3 dated Mar. 21, 2017.
Hrašna et al. "Synthesis, complex compounds and antimicrobial activity of some derivatives of furo[3,2-C]pyridine and their starting compounds," Nova Biotechnologica et Chemica, vol. 11, No. 1, 2012, pp. 73-85.
Ikawa et al., "Photo- and electroluminescence from deep-red- and near-infrared-phosphorescent tris-cyclometalated iridium(III) complexes bearing largely π-extended ligands," Elsevier, Inorganic Chemistry Communications, vol. 38, 2013 (available online Oct. 11, 2013), pp. 14-19.
Jasselin-Hinschberger et al., "Elaboration of Furopyridine Scaffolds," Eur. J. Org. Chem., 2015 (published online Jan. 22, 2015), pp. 2321-2331.
Shiotani et al., "Furopyridines. XXII [1]. Elaboration of the C-Substituents alpha to the Heteronitrogen Atom of Furo[2,3-b]-,-[3,2-b]-,-[2,3-c]- and -[3,2-c]pyridine," J. Heterocyclic Chem., vol. 34, May-Jun. 1997, pp. 901-907.
Taiwanese Office Action and Search Report, dated Jul. 7, 2016, for Taiwanese Application No. 104139355.
Tsujimoto et al., "Pure red electrophosphorescence from polymer light-emitting diodes doped with highly emissive bis-cyclometalated iridium(III) complexes" Elsevier, Journal of Organometallic Chemistry, vol. 695, 2010 (available online May 31, 2010), pp. 1972-1978.
Yook et al., "Furopyridine derivatives as host materials for solution processed blue phosphorescent organic light-emitting diodes," Elsevier, Thin Solid Films, vol. 562, 2014 (available online Apr. 18, 2014), pp. 608-611.

(56) References Cited

OTHER PUBLICATIONS

Chinese Office Action for Appl. No. 201611039280.2 dated Jun. 26, 2018.

* cited by examiner

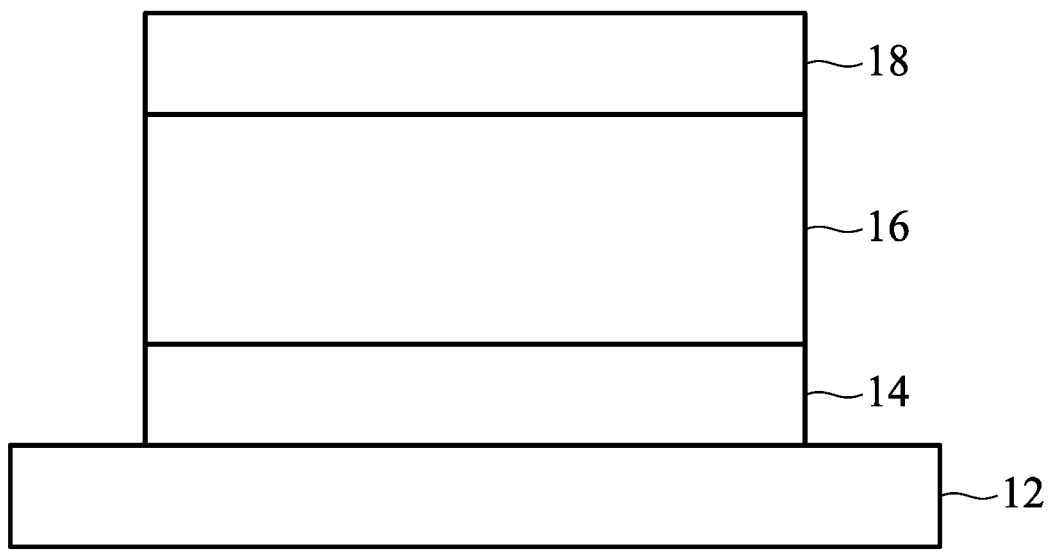

ORGANIC METAL COMPOUND, ORGANIC LIGHT-EMITTING DEVICES EMPLOYING THE SAME

CROSS REFERENCE TO RELATED APPLICATIONS

The application is based on, and claims priority from, Taiwan Application Serial Number 104139355, filed on Nov. 26, 2015, the disclosure of which is hereby incorporated by reference herein in its entirety. Further, the application is also based on, and claims priority from, Taiwan Application Serial Number 105136104, filed on Nov. 7, 2016, the disclosure of which is hereby incorporated by reference herein in its entirety.

TECHNICAL FIELD

The disclosure relates to an organic metal compound and an organic light-emitting device employing the same.

BACKGROUND

An organic light-emitting diode (OLED) is a light-emitting diode employing an organic electroluminescent layer as an active layer. OLED display devices have high luminescent efficiency and long operating lifespans. In comparison with liquid-crystal displays, due to the characteristic of spontaneous emission, a device employing an organic light-emitting diode is free of a back-light source.

Generally, an organic light-emitting device is composed of a light-emission layer sandwiched between a pair of electrodes. When an electric field is applied to the electrodes, the cathode injects electrons into the light-emission layer and the anode injects holes into the light-emission layer. When the electrons recombine with the holes in the light-emission layer, excitons are formed. Recombination of the electron and hole results in light emission.

Depending on the spin states of the hole and electron, the exciton, which results from the recombination of the hole and electron, can have either a triplet or singlet spin state. Luminescence from a singlet exciton results in fluorescence whereas luminescence from a triplet exciton results in phosphorescence. The emissive efficiency of phosphorescence is three times that of fluorescence. Therefore, it is crucial to develop highly efficient phosphorescent material, in order to increase the emissive efficiency of an OLED.

SUMMARY

According to an embodiment of the disclosure, the disclosure provides an organic metal compound having a structure of Formula (I) or Formula (II):

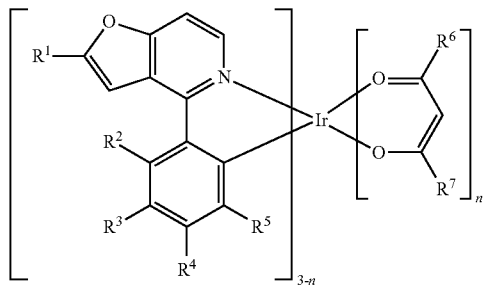

Formula (I)

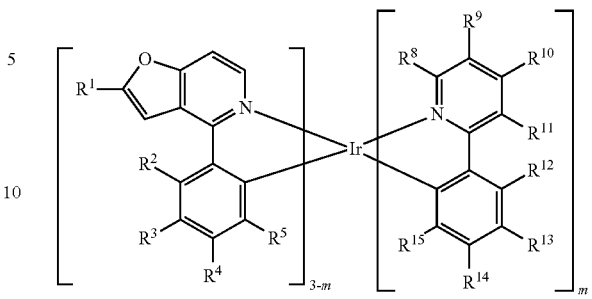

Formula (II)

wherein, $R^1$ is independently hydrogen, $C_{1-12}$ alkyl group, $C_{1-12}$ alkoxy group, amine, $C_{2-6}$ alkenyl group, $C_{2-6}$ alkynyl group, $C_{5-10}$ cycloalkyl group, $C_{3-12}$ heteroaryl group, or $C_{6-12}$ aryl group; $R^2$, $R^3$, $R^4$, and $R^5$ are independent and can be hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group; $R^6$ and $R^7$ are independent and can be $C_{1-6}$ alkyl group, or phenyl group; $R^8$, $R^9$, $R^{10}$, and $R^{11}$ are independent and can be hydrogen, halogen, $C_{1-12}$ alkyl group, $C_{1-12}$ fluoroalkyl group, or two adjacent groups of $R^8$, $R^9$, $R^{10}$, and $R^{11}$ are optionally combined with the carbon atoms which they are attached to, to form a cycloalkyl group, or aryl group; $R^{12}$, $R^{13}$, $R^{14}$, and $R^{15}$ are independent and can be hydrogen, halogen, $C_{1-12}$ alkyl group, $C_{1-12}$ fluoroalkyl group, or two adjacent groups of $R^{12}$, $R^{13}$, $R^{14}$, and $R^{15}$ are optionally combined with the carbon atoms which they are attached to, to form a cycloalkyl group, or aryl group; m is 1 or 2; and, n is 0 or 1.

According to another embodiment of the disclosure, the disclosure provides an organic light-emitting device, the device includes a pair of electrodes; and an organic light-emitting element disposed between the electrodes, wherein the organic light-emitting element includes the aforementioned organic metal compound.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein:

FIG. 1 shows a cross section of an organic light-emitting device disclosed by an embodiment of the disclosure.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

According to embodiments of the disclosure, the disclosure provides an organic metal compound having a structure of Formula (I) or Formula (II):

Formula (I)

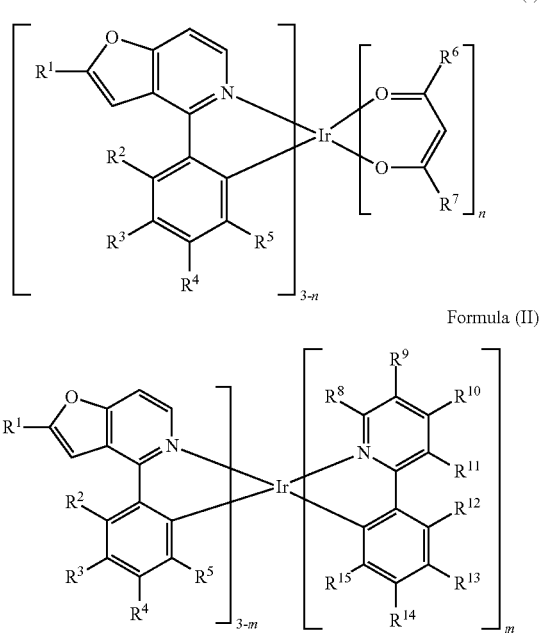

Formula (II)

wherein, $R^1$ is independently hydrogen, $C_{1-12}$ alkyl group, $C_{1-12}$ alkoxy group, amine, $C_{2-6}$ alkenyl group, $C_{2-6}$ alkynyl group, $C_{5-10}$ cycloalkyl group, $C_{3-12}$ heteroaryl group, or $C_{6-12}$ aryl group; $R^2$, $R^3$, $R^4$, and $R^5$ are independent and can be hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group; $R^6$ and $R^7$ are independent and can be $C_{1-6}$ alkyl group, or phenyl group; $R^8$, $R^9$, $R^{10}$, and $R^{11}$ are independent and can be hydrogen, halogen, $C_{1-12}$ alkyl group, $C_{1-12}$ fluoroalkyl group, or two adjacent groups of $R^8$, $R^9$, $R^{10}$, and $R^{11}$ are optionally combined with the carbon atoms which they are attached to, to form a cycloalkyl group, or aryl group; $R^{12}$, $R^{13}$, $R^{14}$, and $R^{15}$ are independent and can be hydrogen, halogen, $C_{1-12}$ alkyl group, $C_{1-12}$ fluoroalkyl group, or two adjacent groups of $R^{12}$, $R^{13}$, $R^{14}$, and $R^{15}$ are optionally combined with the carbon atoms which they are attached to, to form a cycloalkyl group, or aryl group; m is 1 or 2; and, n is 0 or 1. For example, $R^1$ can be hydrogen, methyl group, ethyl group, propyl group, isopropyl group, n-butyl group, isobutyl group, tert-butyl group, pentyl group, hexyl group, cyclohexyl group, phenyl group, biphenyl group, or naphthyl group; $R^2$, $R^3$, $R^4$, and $R^5$ are independent and can be hydrogen, fluorine, methyl group, ethyl group, propyl group, isopropyl group, n-butyl group, isobutyl group, tert-butyl group, pentyl group, hexyl group, fluoromethyl, fluoroethyl, methoxy, ethoxy, propoxy, or isopropoxy or $R^3$ and $R^4$ are combined with the carbon atoms which they are attached to, to form a phenyl group; and, $R^6$ and $R^7$ are independently methyl group, ethyl group, propyl group, isopropyl group, n-butyl group, isobutyl group, tert-butyl group, pentyl group, hexyl group, or phenyl group.

According to embodiments of the disclosure, at least one of $R^1$, $R^2$, $R^3$, $R^4$, and $R^5$ cannot be hydrogen, in order to adjust the luminescent color, increase the solubility of the compound, improve the sublimation yield, and increase the luminous efficiency and lifetime of the organic light-emitting device. According to some embodiments of the disclosure, $R^1$ is independently hydrogen, or $C_{1-12}$ alkyl group; $R^2$, $R^3$, $R^4$, and $R^5$ are independently hydrogen, halogen, $C_{1-12}$ alkyl group, $C_{1-12}$ alkoxy group, or two adjacent groups of $R^2$, $R^3$, $R^4$, and $R^5$ are optionally combined with the carbon atoms which they are attached to, to form an aryl group; $R^6$ and $R^7$ are independent $C_{1-6}$ alkyl group; and, n is 0 or 1. According to embodiments of the disclosure, $R^8$, $R^9$, $R^{10}$, and $R^{11}$ are independent and can be hydrogen, fluorine, methyl group, ethyl group, propyl group, isopropyl group, n-butyl group, isobutyl group, tert-butyl group, pentyl group, hexyl group, fluoromethyl, or fluoroethyl, or $R^9$ and $R^{10}$ are combined with the carbon atoms which they are attached to, to form a phenyl group, and/or $R^{10}$ and $R^{11}$ are combined with the carbon atoms which they are attached to, to form a phenyl group. $R^{12}$, $R^{13}$, $R^{14}$, and $R^{15}$ are independent and can be hydrogen, fluorine, methyl group, ethyl group, propyl group, isopropyl group, n-butyl group, isobutyl group, tert-butyl group, pentyl group, hexyl group, fluoromethyl, or fluoroethyl, or $R^{12}$ and $R^{13}$ are combined with the carbon atoms which they are attached to, to form a phenyl group, and/or $R^{13}$ and $R^{14}$ are combined with the carbon atoms which they are attached to, to form a phenyl group. Herein, the term "fluoroalkyl group" means hydrogen atoms bonded on carbon atoms of alkyl group can be partially or totally replaced with fluorine. For Example, fluoromethyl can be —$CH_2F$, —$CHF_2$— or —$CF_3$. According to some embodiments of the disclosure, $R^1$ is independently hydrogen, or $C_{1-12}$ alkyl group; $R^2$, $R^3$, $R^4$, and $R^5$ are independently hydrogen, halogen, $C_{1-12}$ alkyl group, $C_{1-12}$ alkoxy group, or two adjacent groups of $R^2$, $R^3$, $R^4$, and $R^5$ are optionally combined with the carbon atoms which they are attached to, to form an aryl group; $R^8$, $R^9$, $R^{10}$, and $R^{11}$ are independently hydrogen, $C_{1-12}$ alkyl group, or two adjacent groups of $R^8$, $R^9$, $R^{10}$, and $R^{11}$ are optionally combined with the carbon atoms which they are attached to, to form an aryl group; $R^{12}$, $R^{13}$, $R^{14}$, and $R^{15}$ are independently hydrogen, or $C_{1-12}$ alkyl group; and, m is 1 or 2.

The organic metal compounds of the disclosure can serve as a green phosphorescent dopant material, and can be applied to an organic light-emitting device for enhancing the luminous efficiency and lifetime.

According to some embodiments of the disclosure, the organic metal compound can be

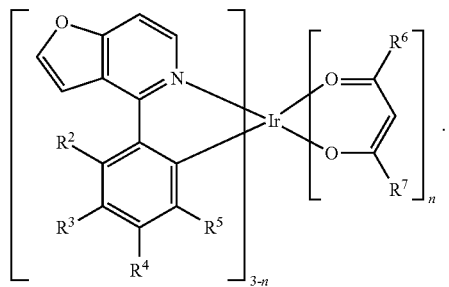

$R^2$, $R^3$, $R^4$, and $R^5$ are independent and can be hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group; $R^6$ and $R^7$ are independent $C_{1-6}$ alkyl group, or phenyl group; and, n is 0, or 1. For example, $R^2$, $R^3$, $R^4$, and $R^5$ are independently hydrogen, fluorine, methyl group, ethyl group, propyl group, isopropyl group, n-butyl group, isobutyl group, tert-butyl group, pentyl group, hexyl group, fluoromethyl, fluoroethyl, methoxy, ethoxy, propoxy, or isopropoxy. Furthermore, $R^3$ and $R^4$ can be combined with the carbon atoms which they are attached to, to form a phenyl group. $R^6$ and $R^7$ can be independently methyl group, ethyl group, propyl group, isopropyl group, n-butyl group, isobutyl group, tert-butyl group, pentyl group, hexyl group, or phenyl group. According to embodiments of the disclosure, $R^2$, $R^3$, $R^4$, and $R^5$ cannot be hydrogen.

According to some embodiments of the disclosure, the organic metal compound can be

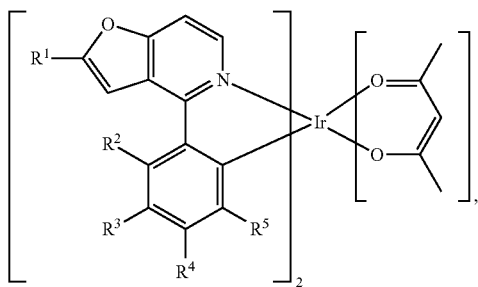

or,

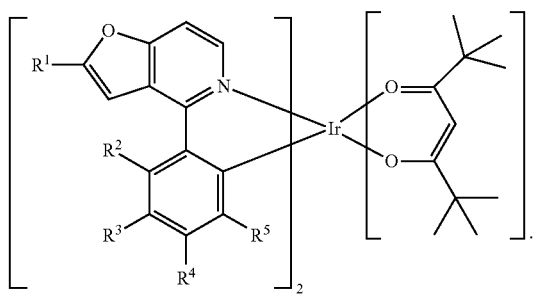

$R^1$ is independent and can be hydrogen, $C_{1-12}$ alkyl group, $C_{1-12}$ alkoxy group, amine, $C_{2-6}$ alkenyl group, $C_{2-6}$ alkynyl group, $C_{5-10}$ cycloalkyl group, $C_{3-12}$ heteroaryl group, or $C_{6-12}$ aryl group; and, $R^2$, $R^3$, $R^4$, and $R^5$ are independent and can be hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group. For example, $R^1$ can be hydrogen, methyl group, ethyl group, propyl group, isopropyl group, n-butyl group, isobutyl group, tert-butyl group, pentyl group, hexyl group, cyclohexyl group, phenyl group, biphenyl group, or naphthyl group. For example, $R^2$, $R^3$, $R^4$, and $R^5$ are independently hydrogen, fluorine, methyl group, ethyl group, propyl group, isopropyl group, n-butyl group, isobutyl group, tert-butyl group, pentyl group, hexyl group, fluoromethyl, fluoroethyl, methoxy, ethoxy, propoxy, or isopropoxy. Furthermore, $R^3$ and $R^4$ can be combined with the carbon atoms which they are attached to, to form a phenyl group. According to embodiments of the disclosure, $R^1$, $R^2$, $R^3$, $R^4$, and $R^5$ cannot be hydrogen.

According to some embodiments of the disclosure, the organic metal compound can be

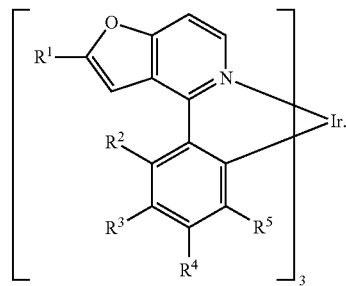

$R^1$ is independent and can be hydrogen, $C_{1-12}$ alkyl group, $C_{1-12}$ alkoxy group, amine, $C_{2-6}$ alkenyl group, $C_{2-6}$ alkynyl group, $C_{5-10}$ cycloalkyl group, $C_{3-12}$ heteroaryl group, or $C_{6-12}$ aryl group; and, $R^2$, $R^3$, $R^4$, and $R^5$ are independent and can be hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group. For example, $R^1$ can be hydrogen, methyl group, ethyl group, propyl group, isopropyl group, n-butyl group, isobutyl group, tert-butyl group, pentyl group, hexyl group, cyclohexyl group, phenyl group, biphenyl group, or naphthyl group. For example, $R^2$, $R^3$, $R^4$, and $R^5$ are independently hydrogen, fluorine, methyl group, ethyl group, propyl group, isopropyl group, n-butyl group, isobutyl group, tert-butyl group, pentyl group, hexyl group, fluoromethyl, fluoroethyl, methoxy, ethoxy, propoxy, or isopropoxy. Furthermore, $R^3$ and $R^4$ can be combined with the carbon atoms which they are attached to, to form a phenyl group. According to embodiments of the disclosure, $R^1$, $R^2$, $R^3$, $R^4$, and $R^5$ cannot be hydrogen.

For example, the organic metal compound having a structure of Formula (I) can be

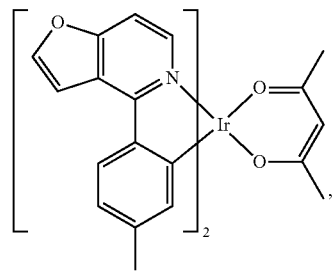

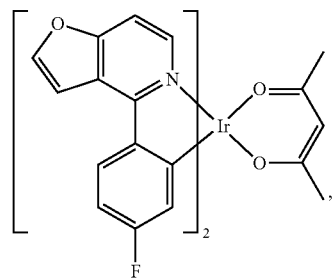

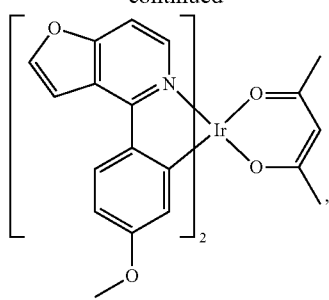
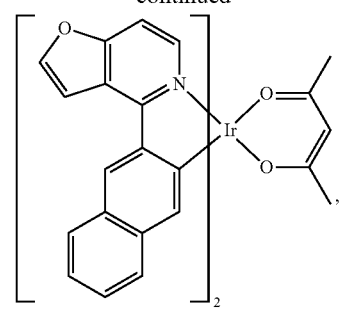
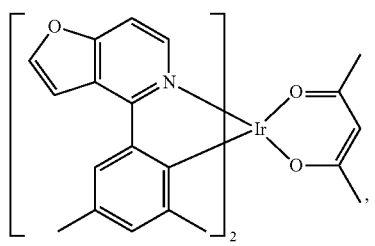
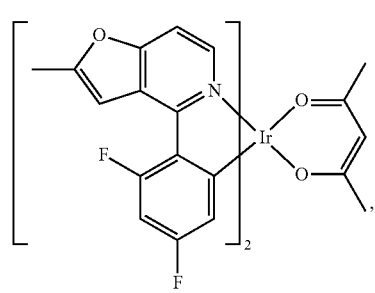
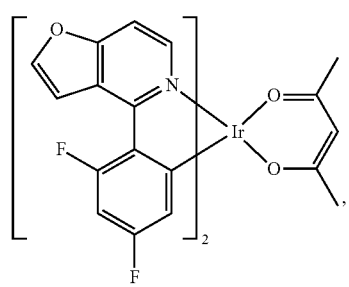
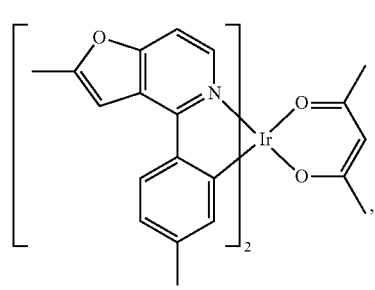
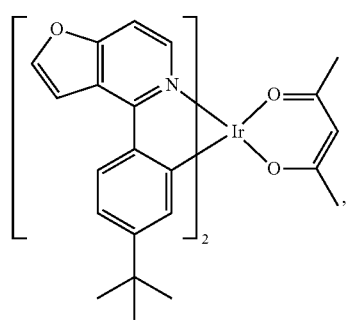
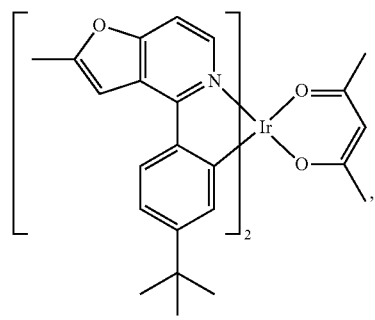
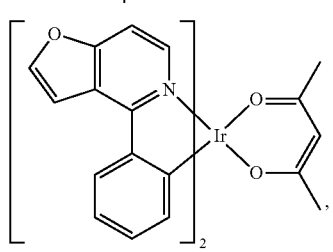
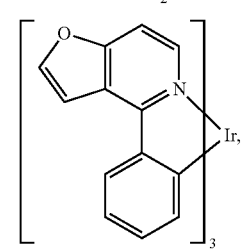
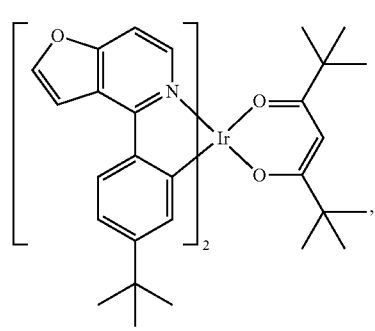

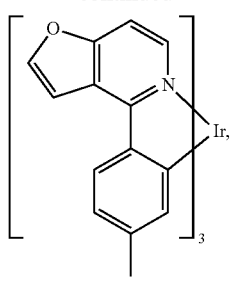

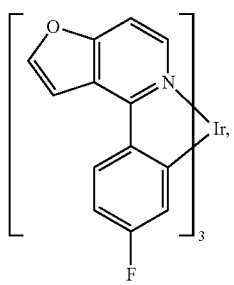

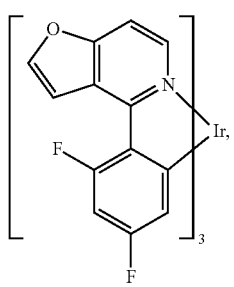

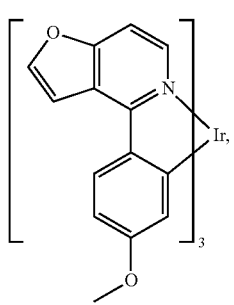

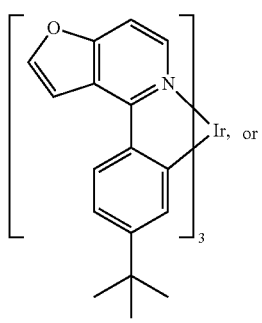

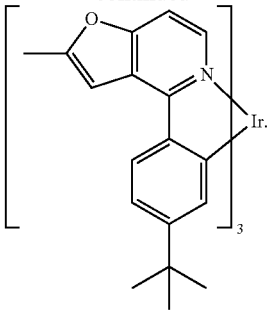

According to some embodiments of the disclosure, the organic metal compound can be

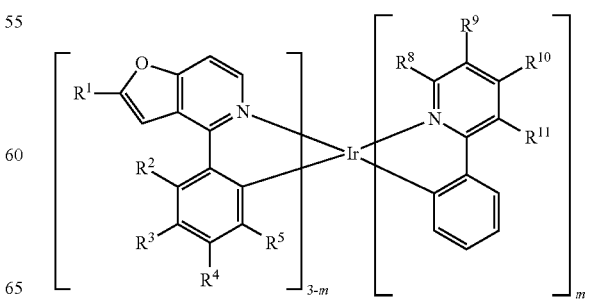

$R^1$ is independent and can be hydrogen, $C_{1-12}$ alkyl group, $C_{1-12}$ alkoxy group, amine, $C_{2-6}$ alkenyl group, $C_{2-6}$ alkynyl group, $C_{5-10}$ cycloalkyl group, $C_{3-12}$ heteroaryl group, or $C_{6-12}$ aryl group; and, $R^2$, $R^3$, $R^4$, and $R^5$ are independent and can be hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group. For example, $R^1$ can be hydrogen, methyl group, ethyl group, propyl group, isopropyl group, n-butyl group, isobutyl group, tert-butyl group, pentyl group, hexyl group, cyclohexyl group, phenyl group, biphenyl group, or naphthyl group. For example, $R^2$, $R^3$, $R^4$, and $R^5$ are independently hydrogen, fluorine, methyl group, ethyl group, propyl group, isopropyl group, n-butyl group, isobutyl group, tert-butyl group, pentyl group, hexyl group, fluoromethyl, fluoroethyl, methoxy, ethoxy, propoxy, or isopropoxy. Furthermore, $R^3$ and $R^4$ can be combined with the carbon atoms which they are attached to, to form a phenyl group. According to embodiments of the disclosure, $R^1$, $R^2$, $R^3$, $R^4$, and $R^5$ cannot be hydrogen, and m can be 1 or 2.

According to some embodiments of the disclosure, the organic metal compound can be $R^1$ is independent and can be hydrogen, $C_{1-12}$ alkyl group, $C_{1-12}$ alkoxy group, amine, $C_{2-6}$ alkenyl group, $C_{2-6}$ alkynyl group, $C_{5-10}$ cycloalkyl group, $C_{3-12}$ heteroaryl group, or $C_{6-12}$ aryl group; and, $R^2$, $R^3$, $R^4$, and $R^5$ are independent and can be hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group. For example, $R^1$ can be hydrogen, methyl group, ethyl group, propyl group, isopropyl group, n-butyl group, isobutyl group, tert-butyl group, pentyl group, hexyl group, cyclohexyl group, phenyl group, biphenyl group, or naphthyl group. For example, $R^2$, $R^3$, $R^4$, and $R^5$ are independently hydrogen, fluorine, methyl group, ethyl group, propyl group, isopropyl group, n-butyl group, isobutyl group, tert-butyl group, pentyl group, hexyl group, fluoromethyl, fluoroethyl, methoxy, ethoxy, propoxy, or isopropoxy. Furthermore, $R^3$ and $R^4$ can be combined with the carbon atoms which they are attached to, to form a phenyl group. According to embodiments of the disclosure, $R^1$, $R^2$, $R^3$, $R^4$, and $R^5$ cannot be hydrogen. $R^8$, $R^9$, $R^{10}$, and $R^{11}$ are independent and can be hydrogen, halogen, $C_{1-12}$ alkyl group, $C_{1-12}$ fluoroalkyl group, or two adjacent groups of $R^8$, $R^9$, $R^{10}$, and $R^{11}$ are optionally combined with the carbon atoms which they are attached to, to form a cycloalkyl group, or aryl group. For example, $R^8$, $R^9$, $R^{10}$, and $R^{11}$ are independent and can be hydrogen, fluorine, methyl group, ethyl group, propyl group, isopropyl group, n-butyl group, isobutyl group, tert-butyl group, pentyl group, hexyl group, fluoromethyl, or fluoroethyl, or $R^9$ and $R^{10}$ are combined with the carbon atoms which they are attached to, to form a phenyl group, and/or $R^{10}$ and $R^{11}$ are combined with the carbon atoms which they are attached to, to form a phenyl group, and m can be 1 or 2.

According to some embodiments of the disclosure, the organic metal compound can be

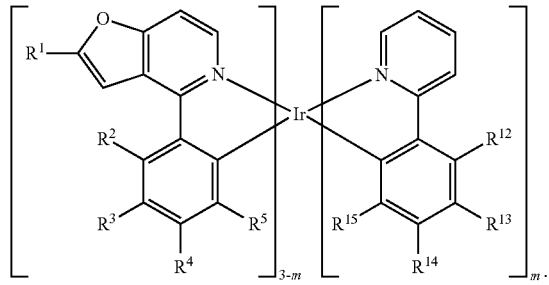

$R^1$ is independent and can be hydrogen, $C_{1-12}$ alkyl group, $C_{1-12}$ alkoxy group, amine, $C_{2-6}$ alkenyl group, $C_{2-6}$ alkynyl group, $C_{5-10}$ cycloalkyl group, $C_{3-12}$ heteroaryl group, or $C_{6-12}$ aryl group; and, $R^2$, $R^3$, $R^4$, and $R^5$ are independent and can be hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group. For example, $R^1$ can be hydrogen, methyl group, ethyl group, propyl group, isopropyl group, n-butyl group, isobutyl group, tert-butyl group, pentyl group, hexyl group, cyclohexyl group, phenyl group, biphenyl group, or naphthyl group. For example, $R^2$, $R^3$, $R^4$, and $R^5$ are independently hydrogen, fluorine, methyl group, ethyl group, propyl group, isopropyl group, n-butyl group, isobutyl group, tert-butyl group, pentyl group, hexyl group, fluoromethyl, fluoroethyl, methoxy, ethoxy, propoxy, or isopropoxy. Furthermore, $R^3$ and $R^4$ can be combined with the carbon atoms which they are attached to, to form a phenyl group. According to embodiments of the disclosure, $R^1$, $R^2$, $R^3$, $R^4$, and $R^5$ cannot be hydrogen. $R^{12}$, $R^{13}$, $R^{14}$, and $R^{15}$ are independent and can be hydrogen, halogen, $C_{1-12}$ alkyl group, $C_{1-12}$ fluoroalkyl group, or two adjacent groups of $R^{12}$, $R^{13}$, $R^{14}$, and $R^{15}$ are optionally combined with the carbon atoms which they are attached to, to form a cycloalkyl group, or aryl group. For example, $R^{12}$, $R^{13}$, $R^{14}$, and $R^{15}$ are independent and can be hydrogen, fluorine, methyl group, ethyl group, propyl group, isopropyl group, n-butyl group, isobutyl group, tert-butyl group, pentyl group, hexyl group, fluoromethyl, or fluoroethyl, or $R^{12}$ and $R^{13}$ are combined with the carbon atoms which they are attached to, to form a phenyl group, and/or $R^{13}$ and $R^{14}$ are combined with the carbon atoms which they are attached to, to form a phenyl group, and m can be 1 or 2.

According to some embodiments of the disclosure, the organic metal compound can be

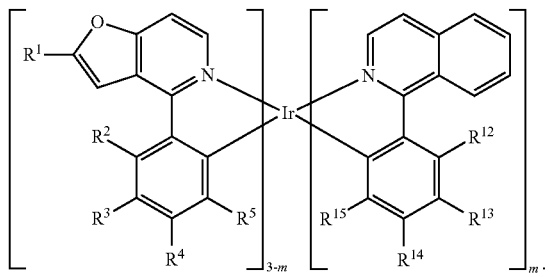

$R^1$ is independent and can be hydrogen, $C_{1-12}$ alkyl group, $C_{1-12}$ alkoxy group, amine, $C_{2-6}$ alkenyl group, $C_{2-6}$ alkynyl group, $C_{5-10}$ cycloalkyl group, $C_{3-12}$ heteroaryl group, or $C_{6-12}$ aryl group; and, $R^2$, $R^3$, $R^4$, and $R^5$ are independent and can be hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group. For example, $R^1$ can be hydrogen, methyl group, ethyl group, propyl group, isopropyl group, n-butyl group, isobutyl group, tert-butyl group, pentyl group, hexyl group, cyclohexyl group, phenyl group, biphenyl group, or naphthyl group. For example, $R^2$, $R^3$, $R^4$, and $R^5$ are independently hydrogen, fluorine, methyl group, ethyl group, propyl group, isopropyl group, n-butyl group, isobutyl group, tert-butyl group, pentyl group, hexyl group, fluoromethyl, fluoroethyl, methoxy, ethoxy, propoxy, or isopropoxy. Furthermore, $R^3$ and $R^4$ can be combined with the carbon atoms which they are attached to, to form a phenyl group. According to embodiments of the disclosure, $R^1$, $R^2$, $R^3$, $R^4$, and $R^5$ cannot be hydrogen. $R^{12}$, $R^3$, $R^{14}$, and $R^{15}$ are independent and can be hydrogen, halogen, $C_{1-12}$ alkyl group, $C_{1-12}$ fluoroalkyl group, or two adjacent groups of $R^{12}$, $R^{13}$, $R^{14}$, and $R^{15}$ are optionally combined with the carbon atoms which they are attached to, to form a cycloalkyl group, or aryl group. For example, $R^{12}$, $R^{13}$, $R^{14}$, and $R^{15}$ are independent and can be hydrogen, fluorine, methyl group, ethyl group, propyl group, isopropyl group, n-butyl group, isobutyl group, tert-butyl group, pentyl group, hexyl group, fluoromethyl, or fluoroethyl, or $R^{12}$ and $R^{13}$ are combined with the carbon atoms which they are attached to, to form a phenyl group, and/or $R^{13}$ and $R^{14}$ are combined with the carbon atoms which they are attached to, to form a phenyl group, and m can be 1 or 2.
For example, the organic metal compound having a structure of Formula (II) can be
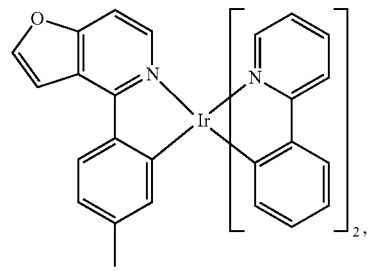
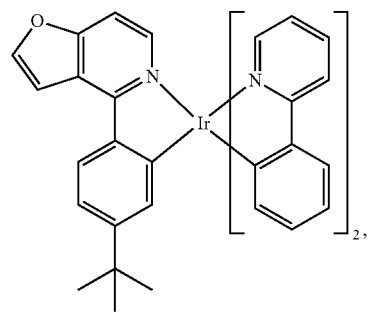
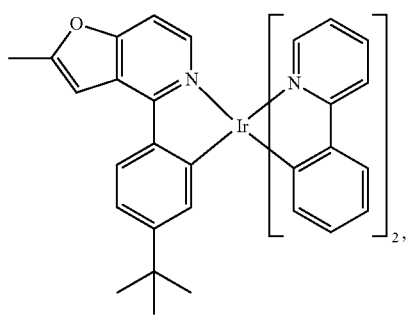
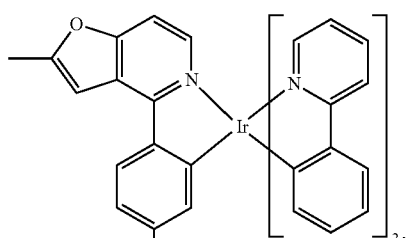
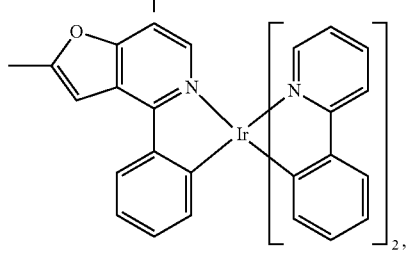
-continued
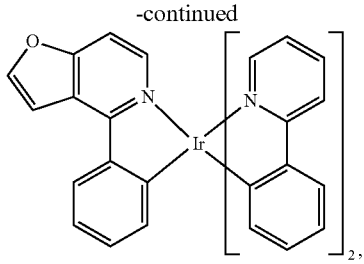
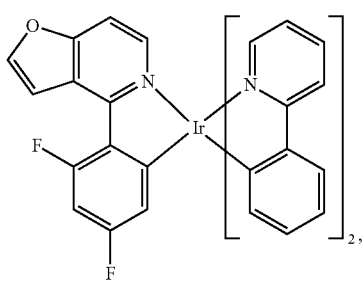
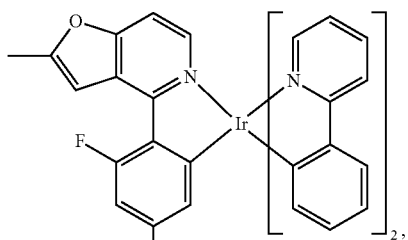
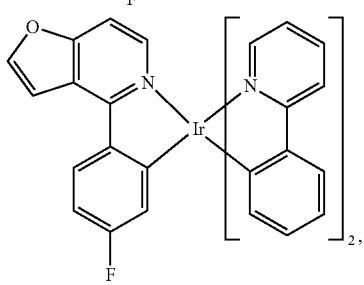
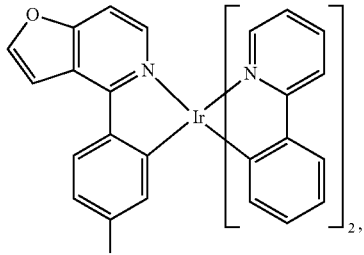
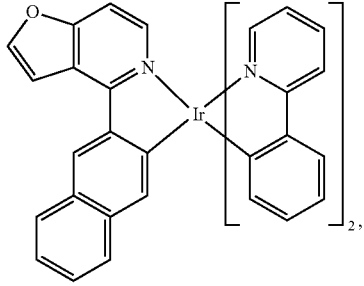

-continued

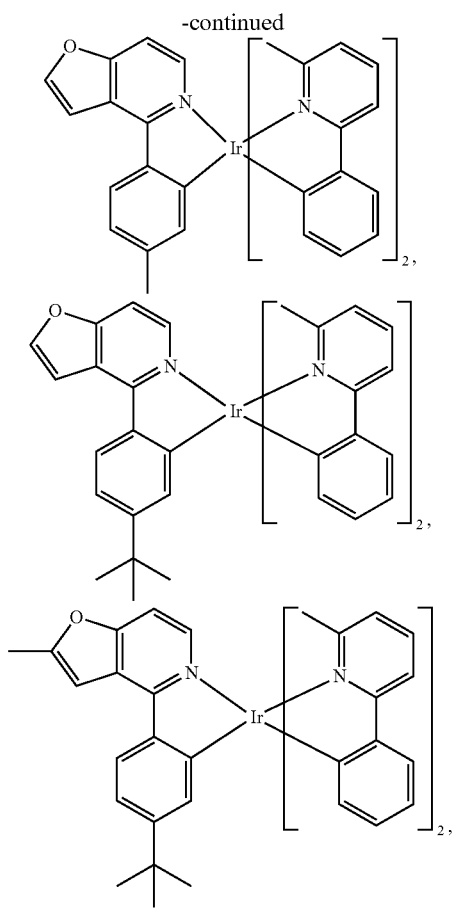

The following examples are intended to illustrate the disclosure more fully without limiting the scope, since numerous modifications and variations will be apparent to those skilled in this art.

Example 1: Preparation of Organic Metal Compound (I)

Organic metal compound (I)

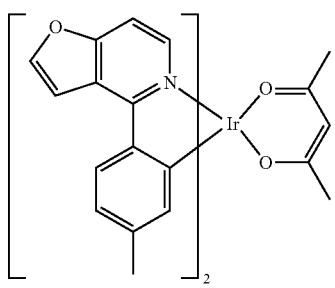

130 mmol of nitromethane, 52 mmol of 2-furfural, and 10 ml of methanol were added into a reaction bottle. Next, 130 mL of sodium hydroxide aqueous solution (1M) were drop-wisely added into the reaction bottle at 0° C. After stirring at 0° C. for 15 min, the mixture was added slowly into a hydrochloric acid aqueous solution (50 ml, 8 M). Next, the reaction was terminated after being checked by thin layer chromatography (TLC), and the result was added into a reaction bottle with CH₂Cl₂ and brine. After extracting, the organic phase was collected. Next, an organic phase was separated and concentrated, and then dried by anhydrous magnesium sulfate. Finally, the result was purified by column chromatography with petroleum ether and ethyl acetate, obtaining Compound (I) with a yield of 93%. The synthesis pathway of the above reaction was as follows:

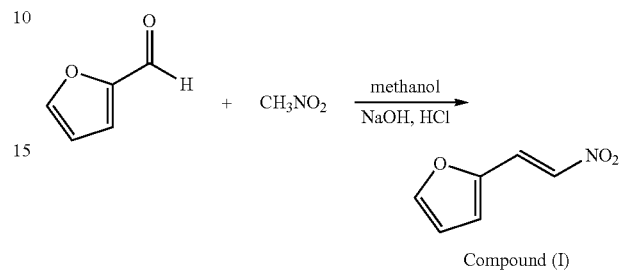

Compound (I)

The physical measurement of the compound (I) is listed below: $^1$H-NMR (200 MHz, CDCl$_3$, δ): 7.77 (d, 1H), 7.59 (s, 1H), 7.53 (d, 1H), 6.89 (d, 1H), 6.57 (dd, 1H).

Next, 30 ml of ethyl ether and 81 mmol of lithium aluminium hydride were added into a reaction bottle. After stirring at 0° C., 27 mmol of compound (I) and 50 ml of ethyl ether was added slowly into the reaction bottle at 0° C. After stirring for 10 min, the reaction bottle was heated to room temperature and then heated to reflux for 8 hr. Next, the reaction bottle was cooled to 0° C., and then water was added slowly to quench reaction. Next, sodium hydroxide aqueous solution (10 wt %) was added into the reaction bottle. After diluting with ethyl ether, filtrating, and concentrating, compound (II) is obtained. The synthesis pathway of the above reaction was as follows:

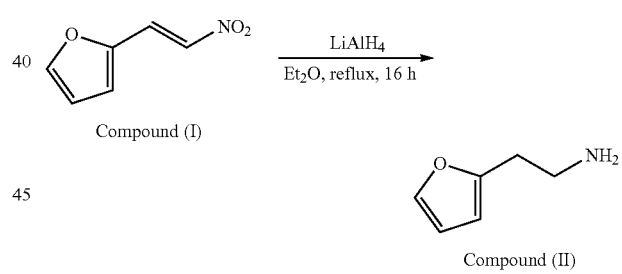

Compound (II)

Next, 55.1 mmol of compound (II), and 200 ml of water were added into a reaction bottle. Next, 82.5 mmol of 4-methylbenzoyl chloride was added into the reaction bottle at 0° C. After the addition was complete, sodium hydroxide aqueous solution (20 wt %) was added into the reaction bottle. After stirring for 8 hr and filtrating, compound (III) was obtained. The synthesis pathway of the above reaction was as follows:

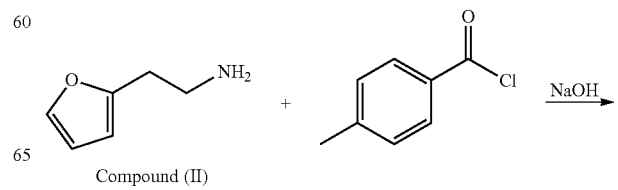

Compound (II)

-continued

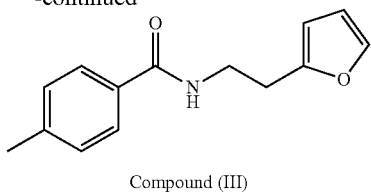

Compound (III)

Next, 10 mmol of compound (III), 20 ml of toluene, and 3 mmol of phosphorus oxychloride ($POCl_3$) were added into the reaction bottle. After heating the reaction bottle for 2 hr, the mixture was neutralized by saturated sodium bicarbonate aqueous solution, and extracted with toluene. After concentrating, Compound (IV) was obtained. The synthesis pathway of the above reaction was as follows:

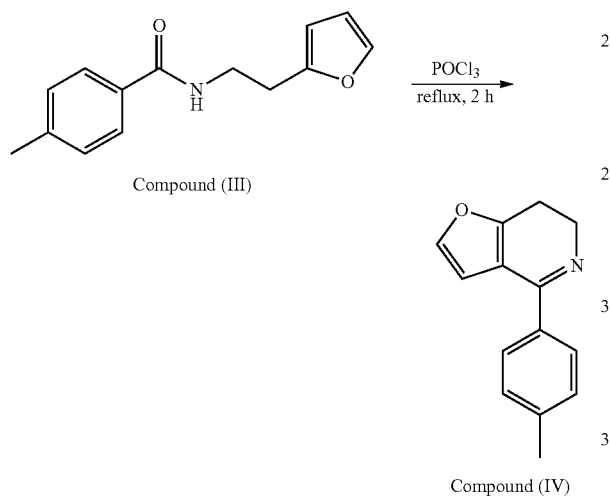

Compound (III)

Compound (IV)

Next, 10 mmol of Compound (IV), 0.5 g of palladium 10% on carbon (Pd/C catalyst), and 100 ml of toluene were added into a reaction bottle. Next, the reaction bottle was heated to reflux for 18 hr. Next, after removing Pd/C catalyst by filtration, the filtrate was extracted three times using ethyl acetate (EA) and water as the extraction solvent, and an organic phase was separated and concentrated, and then purified by column chromatography, obtaining Compound (V) with a yield of 92%. The synthesis pathway of the above reaction was as follows:

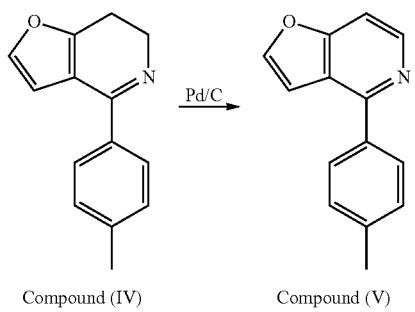

Compound (IV)    Compound (V)

The physical measurement of the Compound (V) is listed below: $^1$H-NMR (200 MHz, $CDCl_3$, δ): 8.56-8.53 (d, 1H), 7.86-7.82 (d, 2H), 7.66-7.65 (m, 1H), 7.39-7.36 (d, 1H), 7.33-7.29 (d, 2H), 7.05-7.04 (m, 1H), 2.42 (s, 3H).

Next, 1.54 mmol of Compound (V), iridium trichloride ($IrCl_3$) (0.7 mmol), 15 ml of 2-methoxyethanol, and 5 ml of water were added into the reaction bottle. Next, after removing moisture and purging nitrogen gas several times, the reaction bottle was heated to reflux. After reacting for 24 hr and cooling down to room temperature, the result was filtrated. The filter cake was collected, washed with water and methanol, and dried, obtaining Compound (VI). The synthesis pathway of the above reaction was as follows:

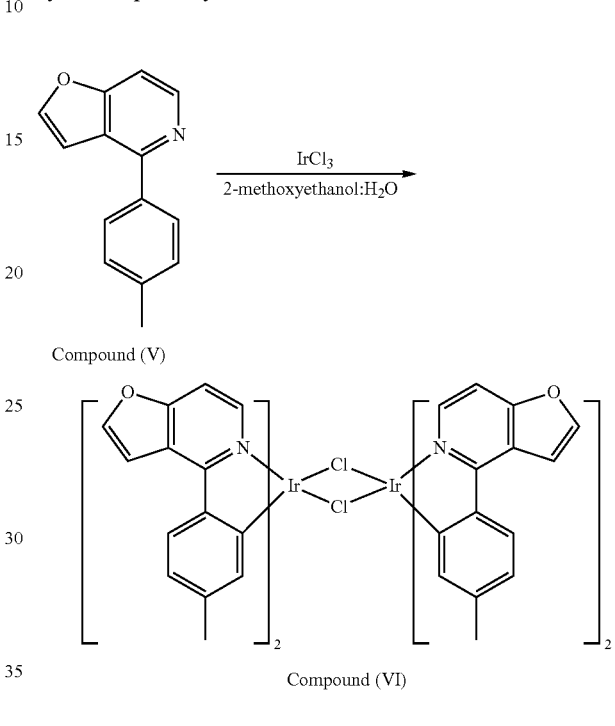

Compound (V)

Compound (VI)

Next, 1 mmol of Compound (VI), 3 mmol of acetylacetone, 2 mmol of sodium carbonate, and 10 ml of 2-methoxyethanol were added into a reaction bottle. Next, after removing moisture and purging nitrogen gas several times, the reaction bottle was heated to 120° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (I) with a yield of 50%. The synthesis pathway of the above reaction was as follows:

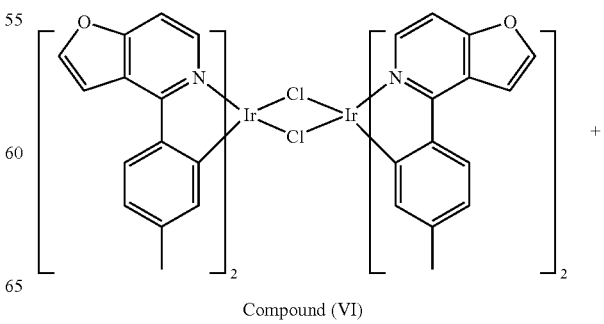

Compound (VI)

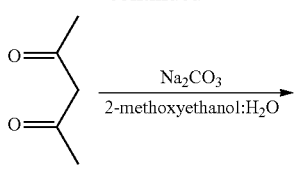

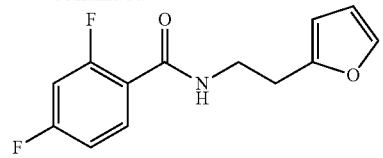

Compound (VII)

Next, 10 mmol of Compound (VII), 20 ml of toluene, and 3 mmol of phosphorus oxychloride ($POCl_3$) were added into the reaction bottle. After heating the reaction bottle for 2 hr, the mixture was neutralized by saturated sodium bicarbonate aqueous solution, and extracted with toluene. After concentrating, Compound (VIII) was obtained. The synthesis pathway of the above reaction was as follows:

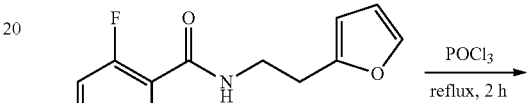

Compound (VII)

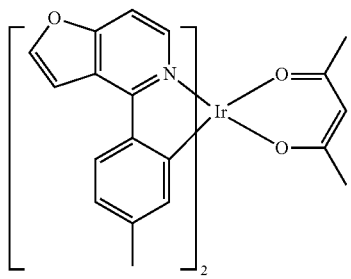

Organic metal compound (I)

The physical measurement of Organic metal compound (I) is listed below: $^1$H-NMR (200 MHz, $CDCl_3$, δ): 8.40-8.37 (d, 2H), 7.83-7.79 (m, 4H), 7.51-7.50 (s, 2H), 7.32-7.28 (d, 2H), 6.70-6.66 (d, 2H), 6.09 (s, 2H), 5.19 (s, 1H), 2.03 (s, 6H), 1.75 (s, 6H).

Example 2: Preparation of Organic Metal Compound (II) of the Above Reaction

Organic metal compound (II)

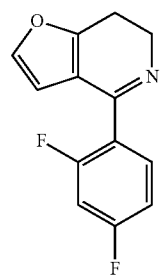

Compound (VIII)

Next, 10 mmol of Compound (VIII), 0.5 g of palladium 10% on carbon (Pd/C catalyst), and 100 ml of toluene were added into the reaction bottle. Next, the reaction bottle was heated to reflux for 18 hr. Next, after removing Pd/C catalyst by filtration, the filtrate was extracted three times using ethyl acetate (EA) and water as the extraction solvent, and an organic phase was separated and concentrated, and then purified by column chromatography, obtaining Compound (IX) with a yield of 95%. The synthesis pathway of the above reaction was as follows:

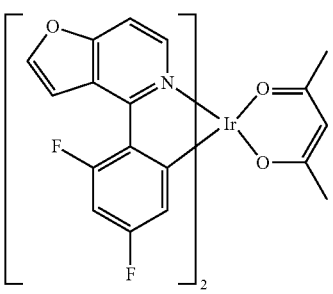

First, 55.1 mmol of Compound (II), and 200 ml of water were added into a reaction bottle. Next, 82.5 mmol of 2,4-difluorobenzoyl chloride was added into the reaction bottle at 0° C. After the addition was complete, sodium hydroxide aqueous solution (20 wt %) was added into the reaction bottle. After stirring for 8 hr, the mixture was filtered, obtaining Compound (VII). The synthesis pathway of the above reaction was as follows:

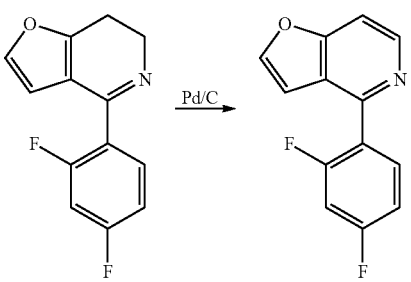

Compound (VIII)  Compound (IX)

The physical measurement of Compound (IX) is listed below: $^1$H-NMR (200 MHz, $CDCl_3$, δ): 8.61-8.58 (d, 1H), 7.84-7.72 (m, 1H), 7.70-7.68 (d, 1H), 7.49-7.46 (d, 1H), 7.09-6.92 (m, 2H), 6.83-6.80 (m, 1H)

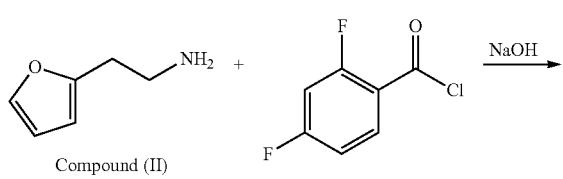

Compound (II)

Next, Compound (IX) (1.54 mmol), and 0.7 mmol of iridium trichloride (IrCl₃), 15 ml of 2-methoxyethanol, and 5 ml of water were added into the reaction bottle. Next, after removing moisture and purging nitrogen gas several times, the reaction bottle was heated to reflux. After reacting for 24 hr and cooling down to room temperature, the result was filtrated. The filter cake was collected, washed with water and methanol, and dried, obtaining (X). The synthesis pathway of the above reaction was as follows:

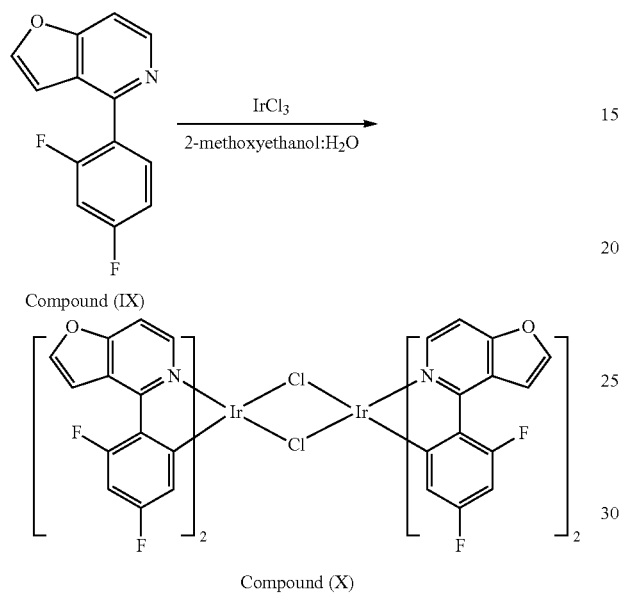

Next, 1 mmol of Compound (X), 3 mmol of acetylacetone, 2 mmol of sodium carbonate (Na₂CO₃), and 10 ml of 2-methoxyethanol were added into a reaction bottle. Next, after removing moisture and purging nitrogen gas several times, the reaction bottle was heated to 120° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (II) with a yield of 45%. The synthesis pathway of the above reaction was as follows:

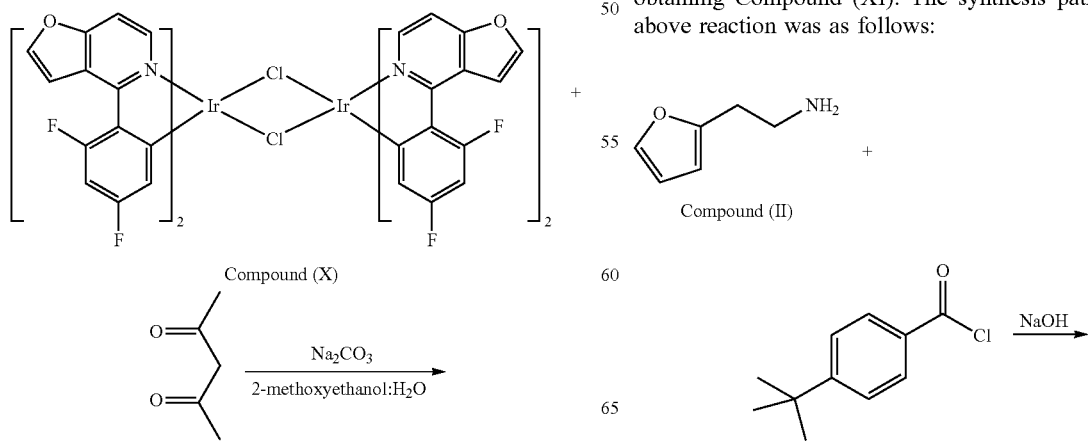

Organic metal compound (II)

The physical measurement of Organic metal compound (II) is listed below: $^1$H-NMR (200 MHz, CDCl₃, δ): 8.40-8.37 (d, 2H), 7.76-7.75 (m, 2H), 7.55 (m, 2H), 7.43-7.40 (d, 2H), 6.41-6.31 (m, 2H), 5.67-5.61 (m, 2H), 5.24 (s, 1H), 1.78 (s, 6H).

Example 3: Preparation of Organic Metal Compound (III)

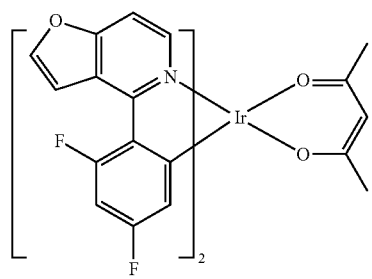

Organic metal compound (III)

55.1 mmol of Compound (II), and 200 ml of water were added into the reaction bottle. Next, 82.5 mmol of 4-tert-Butylbenzoyl chloride was added into the reaction bottle at 0° C. After the addition was complete, sodium hydroxide aqueous solution (20 wt %) was added into the reaction bottle. After stirring for 8 hr, the mixture was filtrated, obtaining Compound (XI). The synthesis pathway of the above reaction was as follows:

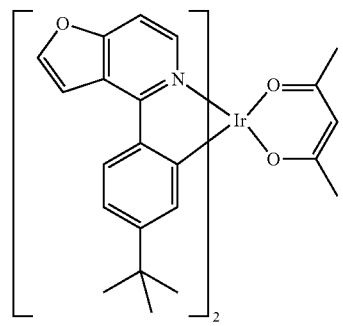

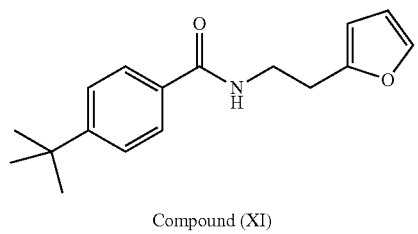

Compound (XI)

Next, 10 mmol of Compound (XI), 20 ml of toluene, and 3 mmol of phosphorus oxychloride (POCl$_3$) were added into the reaction bottle. After heating the reaction bottle for 2 hr, the mixture was neutralized by saturated sodium bicarbonate aqueous solution, and extracted with toluene. After concentrating, Compound (XII) was obtained. The synthesis pathway of the above reaction was as follows:

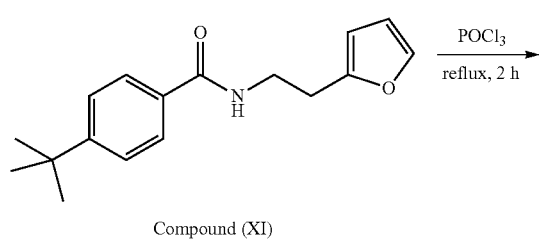

Compound (XI)

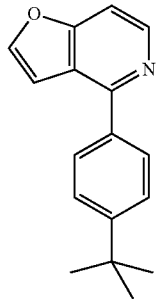

Compound (XII)

Next, 10 mmol of Compound (XII), 0.5 g of palladium 10% on carbon (Pd/C catalyst), and 100 ml of toluene were added into the reaction bottle. Next, the reaction bottle was heated to reflux for 18 hr. Next, after removing Pd/C catalyst by filtration, the filtrate was extracted three times using ethyl acetate (EA) and water as the extraction solvent, and an organic phase was separated and concentrated, and then purified by column chromatography, obtaining Compound (XIII) with a yield of 75%. The synthesis pathway of the above reaction was as follows:

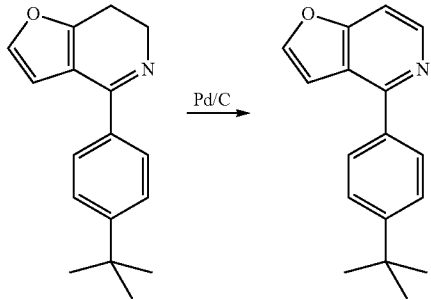

Compound (XII)   Compound (XIII)

The physical measurement of Compound (XIII) is listed below: $^1$H-NMR (200 MHz, CDCl$_3$, δ): 8.58-8.55 (d, 1H), 7.92-7.88 (d, 2H), 7.70-7.69 (m, 1H), 7.68 (m, 1H), 7.57-7.53 (d, 2H), 7.42-7.38 (d, 1H), 7.10-7.09 (s, 1H), 1.38 (s, 9H).

Next, 1.54 mmol of Compound (XIII), and 0.7 mmol of iridium trichloride (IrCl$_3$), 15 ml of 2-methoxyethanol, and 5 ml of water were added into the reaction bottle. Next, after removing moisture and purging nitrogen gas several times, the reaction bottle was heated to reflux. After reacting for 24 hr and cooling down to room temperature, the result was filtrated. The filter cake was collected, washed with water and methanol, and dried, obtaining Compound (XIV). The synthesis pathway of the above reaction was as follows:

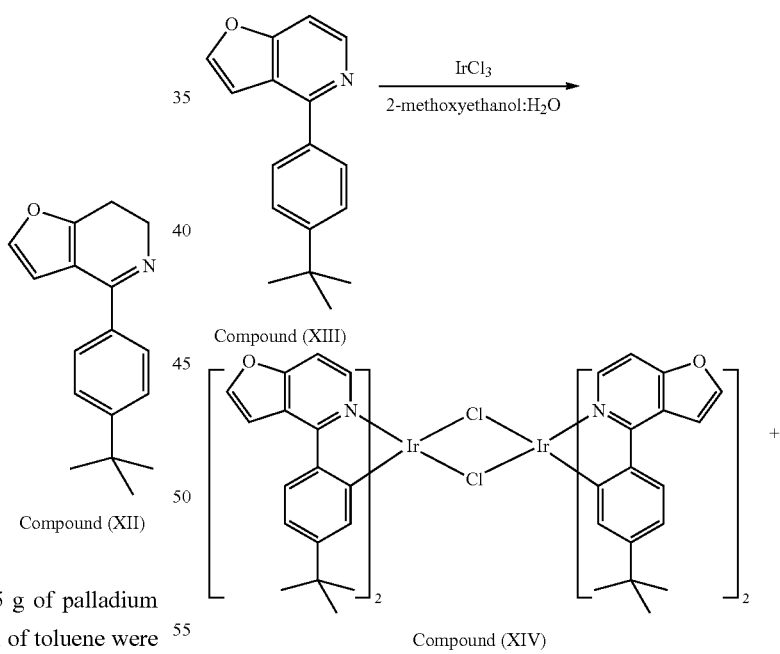

Next, 1 mmol of Compound (XIV), 3 mmol of acetylacetone, 2 mmol of sodium carbonate (Na$_2$CO$_3$), and 10 ml of 2-methoxyethanol were added into a reaction bottle. Next, after removing moisture and purging nitrogen gas several times, the reaction bottle was heated to 120° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (III) with a yield of 54%. The synthesis pathway of the above reaction was as follows:

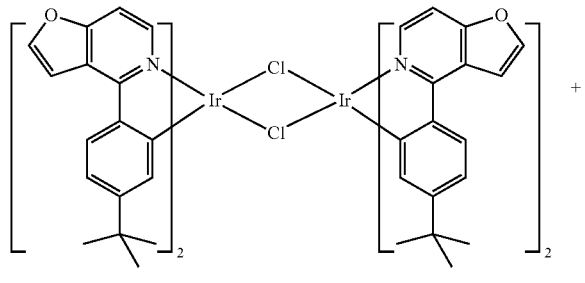

Compound (XIV)

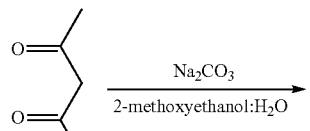

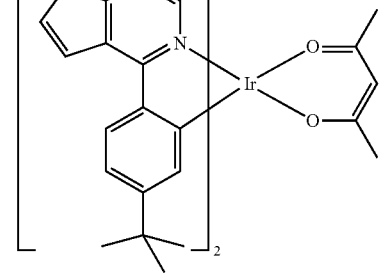

Organic metal compound (III)

The physical measurement of Organic metal compound (III) is listed below $^1$H-NMR (200 MHz, CDCl$_3$, δ): 8.44-8.41 (d, 2H), 7.83-7.78 (m, 4H), 7.50-7.49 (m, 2H), 7.35-7.32 (d, 2H), 6.92-6.87 (m, 2H), 6.22-6.21 (m, 2H), 5.29 (s, 1H), 1.77 (s, 6H), 0.99 (s, 9H).

Example 4: Preparation of Organic Metal Compound (IV)

Organic metal compound (IV)

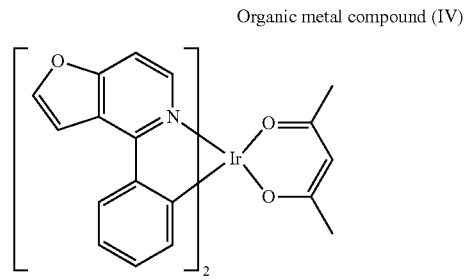

55.1 mmol of Compound (II), and 200 ml of water were added into the reaction bottle. Next, 82.5 mmol of benzoyl chloride was added into the reaction bottle at 0° C. After the addition was complete, sodium hydroxide aqueous solution (20 wt %) was added into the reaction bottle. After stirring for 8 hr, the mixture was filtrated, obtaining Compound (XV). The synthesis pathway of the above reaction was as follows:

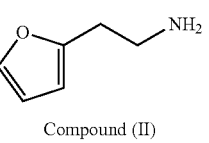 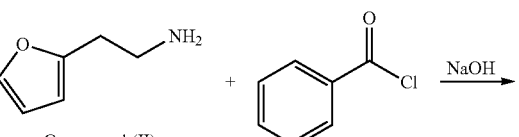

Compound (II)

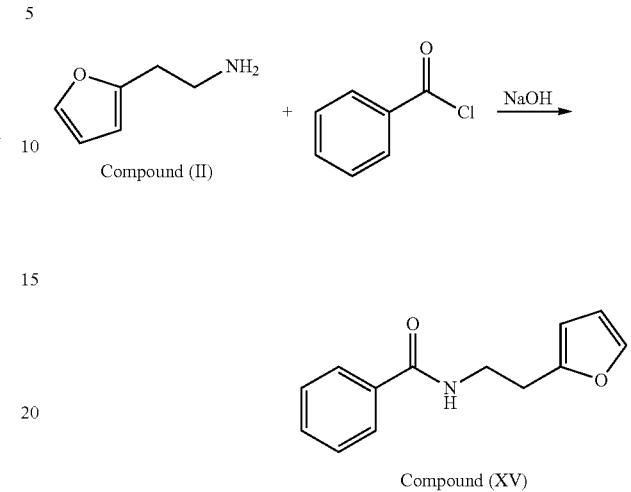

Compound (XV)

Next, 10 mmol Compound (XV), 20 ml of toluene, and 3 mmol of phosphorus oxychloride (POCl$_3$) were added into the reaction bottle. After heating the reaction bottle for 2 hr, the mixture was neutralized by saturated sodium bicarbonate aqueous solution, and extracted with toluene. After concentrating, Compound (XVI) was obtained. The synthesis pathway of the above reaction was as follows:

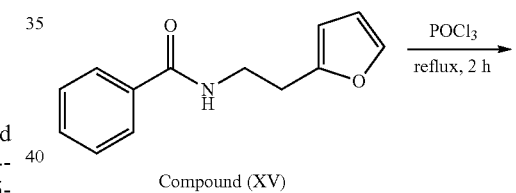

Compound (XV)

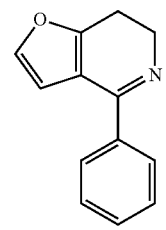

Compound (XVI)

Next, Compound (XVI) (10 mmol), 0.5 g of palladium 10% on carbon (Pd/C catalyst), and 100 ml of toluene were added into the reaction bottle. Next, the reaction bottle was heated to reflux for 18 hr. Next, after removing Pd/C catalyst by filtration, the filtrate was extracted three times using ethyl acetate (EA) and water as the extraction solvent, and an organic phase was separated and concentrated, and then purified by column chromatography, obtaining Compound (XVII) with a yield of 96%. The synthesis pathway of the above reaction was as follows:

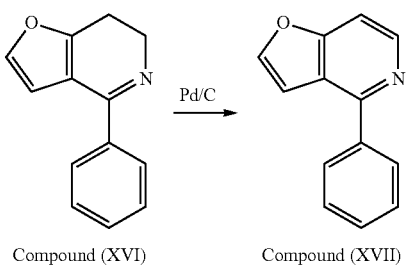 [SMILES: c1ccc(C2=NCCc3occc32)cc1 ; c1ccc(-c2nccc3occc23)cc1]

Compound (XVI)    Compound (XVII)

The physical measurement of Compound (XVII) is listed below: ¹H-NMR (200 MHz, CDCl$_3$, δ): 8.61 (d, 1H), 7.98-7.94 (d, 2H), 7.71-7.70 (s, 1H), 7.58-7.42 (m, 5H), 7.09 (s, 1H).

Next, 1.54 mmol of Compound (XVII), and 0.7 mmol of iridium trichloride (IrCl$_3$), 15 ml of 2-methoxyethanol, and 5 ml of water were added into the reaction bottle. Next, after removing moisture and purging nitrogen gas several times, the reaction bottle was heated to reflux. After reacting for 24 hr and cooling down to room temperature, the result was filtrated. The filter cake was collected, washed with water and methanol, and dried, obtaining Compound (XVIII). The synthesis pathway of the above reaction was as follows:

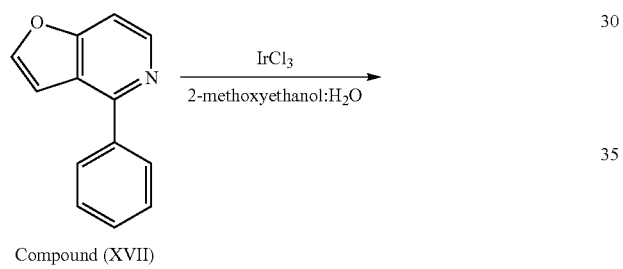

Compound (XVII)

Compound (XVIII)

Next, 1 mmol of Compound (XVIII), 3 mmol of acetylacetone, 2 mmol of sodium carbonate (Na$_2$CO$_3$), and 10 ml of 2-methoxyethanol were added into a reaction bottle. Next, after removing moisture and purging nitrogen gas several times, the reaction bottle was heated to 120° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (IV) with a yield of 46%. The synthesis pathway of the above reaction was as follows:

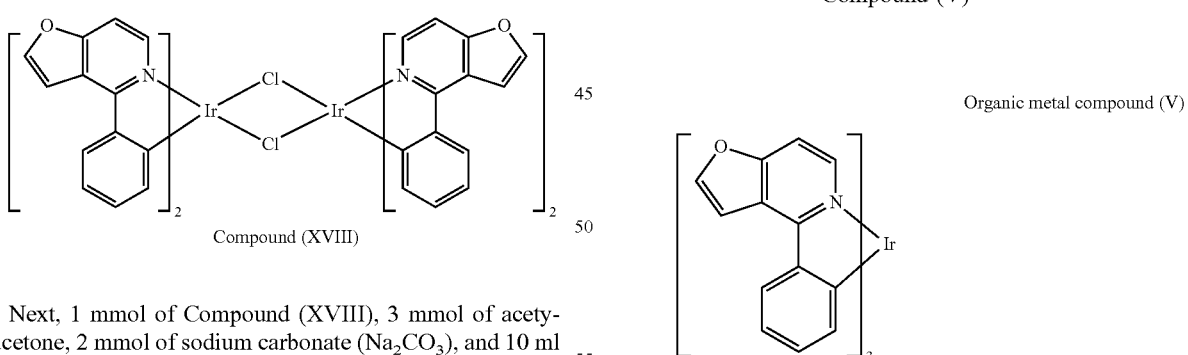

Compound (XVIII)

Organic metal compound (IV)

The physical measurement of Organic metal compound (IV) is listed below ¹H-NMR (200 MHz, CDCl$_3$, δ): 8.45-8.42 (d, 2H), 7.94-7.90 (d, 2H), 7.80 (m, 2H), 7.52 (m, 2H), 7.37-7.33 (d, 2H), 6.89-6.82 (t, 2H), 6.68-6.61 (t, 2H), 6.29-6.25 (d, 2H), 5.22 (s, 1H), 1.77 (s, 3H).

Example 5: Preparation of Organic Metal Compound (V)

Organic metal compound (V)

1 mmol of Organic metal compound (IV), 2 mmol of Compound (XVII), and 15 mL of glycerol were added into a reaction bottle. Next, after removing moisture and purging nitrogen gas several times, the reaction bottle was heated to 200° C. After reacting for 48 hr and cooling down to room temperature, the result was filtrated. The filter cake was collected and washed with water and dichloromethane, and then purified by column chromatography, obtaining Organic metal compound (V) with a yield of 47%. The synthesis pathway of the above reaction was as follows:

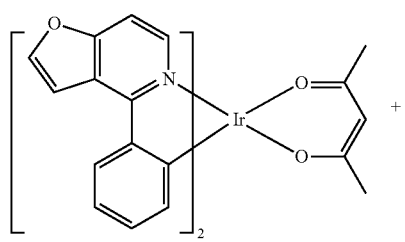

Organic metal compound (IV)

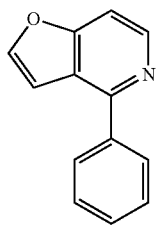

Compound (XVII)

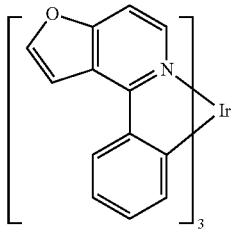

Organic metal compound (V)

The physical measurement of Organic metal compound (V) is listed below $^1$H-NMR (200 MHz, CDCl$_3$, δ): 8.05-8.02 (d, 3H), 7.73-7.72 (m, 3H), 7.54-7.40 (m, 3H), 7.40-7.37 (d, 3H), 7.05-6.82 (m, 12H).

Example 6: Preparation of Organic Metal Compound (VI)

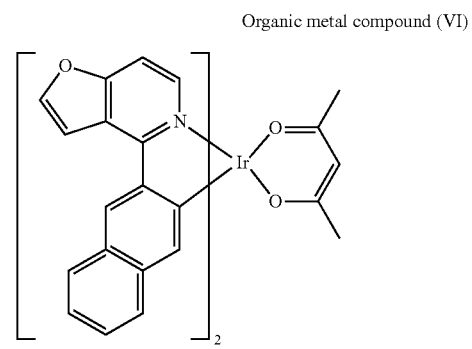

Organic metal compound (VI)

55.1 mmol of Compound (II), and 200 ml of water were added into the reaction bottle. Next, 82.5 mmol of 2-naphthoyl chloride were added into the reaction bottle at 0° C. After the addition was complete, sodium hydroxide aqueous solution (20 wt %) was added into the reaction bottle. After stirring for 8 hr, the mixture was filtrated, obtaining Compound (XIX). The synthesis pathway of the above reaction was as follows:

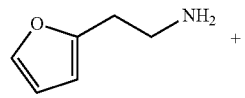

Compound (II)

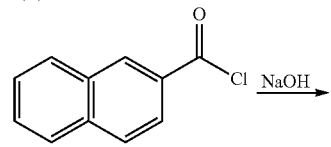

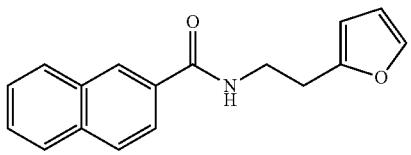

Compound (XIX)

Next, 10 mmol of Compound (XIX), 20 ml of toluene, and 3 mmol of phosphorus oxychloride (POCl$_3$) were added into the reaction bottle. After heating the reaction bottle for 2 hr, the mixture was neutralized by saturated sodium bicarbonate aqueous solution, and extracted with toluene. After concentrating, Compound (XX) is obtained. The synthesis pathway of the above reaction was as follows:

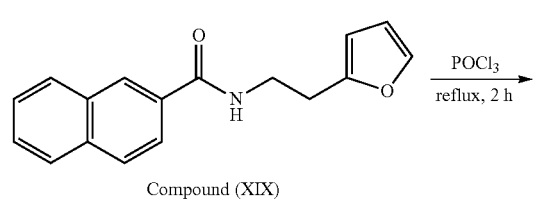

Compound (XIX)

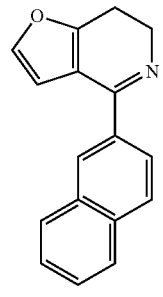

Compound (XX)

Next, 10 mmol of Compound (XX), 0.5 g of palladium 10% on carbon (Pd/C catalyst), and 100 ml of toluene were added into the reaction bottle. Next, the reaction bottle was heated to reflux for 18 hr. Next, after removing Pd/C catalyst by filtration, the filtrate was extracted three times using ethyl acetate (EA) and water as the extraction solvent, and an organic phase was separated and concentrated, and then purified by column chromatography, obtaining Compound (XXI) with a yield of 72%. The synthesis pathway of the above reaction was as follows:

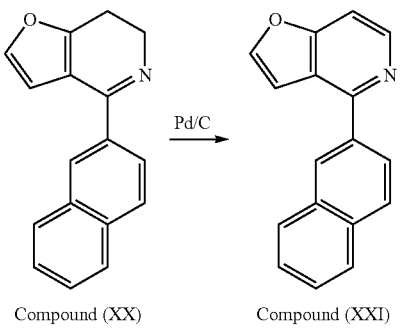

Compound (XX)   Compound (XXI)

The physical measurement of Compound (XXI) is listed below: $^1$H-NMR (200 MHz, CDCl$_3$, δ): 8.66-8.63 (d, 1H), 8.42 (s, 1H), 8.14-7.89 (m, 4H), 7.74-7.72 (d, 1H), 7.56-7.44 (m, 3H), 7.17 (s, 1H).

Next, Compound (XXI) (1.54 mmol), and 0.7 mmol of iridium trichloride (IrCl$_3$), 15 ml of 2-methoxyethanol, and 5 ml of water were added into the reaction bottle. Next, after removing moisture and purging nitrogen gas several times, the reaction bottle was heated to reflux. After reacting for 24 hr and cooling down to room temperature, the result was filtrated. The filter cake was collected, washed with water and methanol, and dried, obtaining Compound (XXII). The synthesis pathway of the above reaction was as follows:

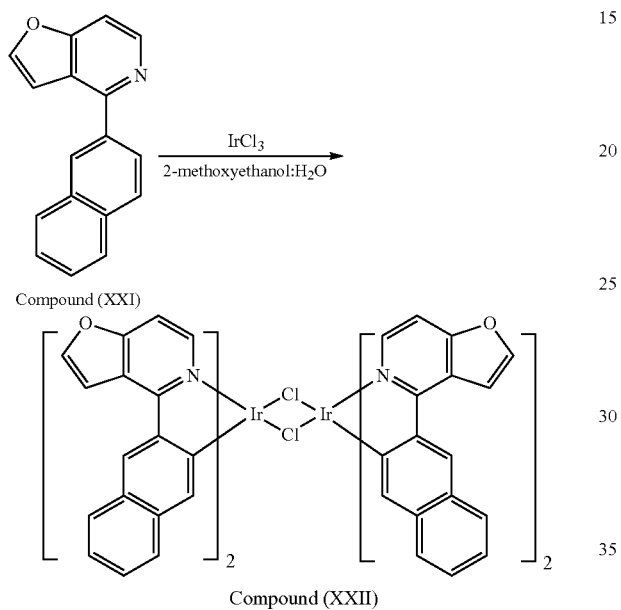

Compound (XXI)

Compound (XXII)

Next, 1 mmol of Compound (XXII), 3 mmol of acetylacetone, 2 mmol of sodium carbonate (Na$_2$CO$_3$), and 10 ml of 2-methoxyethanol were added into a reaction bottle. Next, after removing moisture and purging nitrogen gas several times, the reaction bottle was heated to 120° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (VI) with a yield of 48%. The synthesis pathway of the above reaction was as follows:

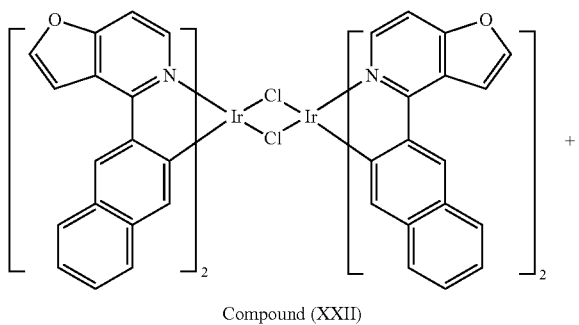

+

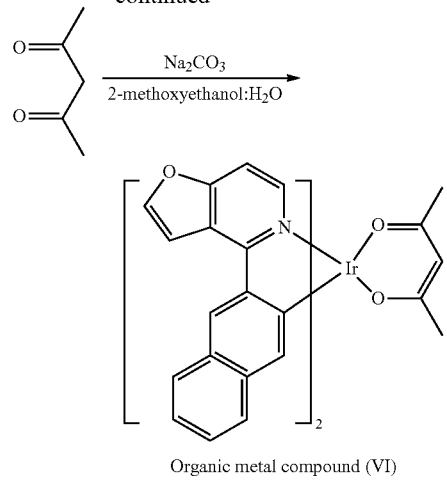

Organic metal compound (VI)

The physical measurement of Organic metal compound (VI) is listed below $^1$H-NMR (200 MHz, CDCl$_3$, δ): 8.60-8.57 (d, 2H), 8.42 (s, 2H), 7.92 (m, 2H), 7.91 (m, 2H), 7.77-7.65 (m, 2H), 7.48-7.45 (d, 2H), 7.16-6.60 (m, 6H), 6.60 (s, 2H), 5.25 (s, 1H), 1.77 (s, 6H).

Example 7: Preparation of Organic Metal Compound (VII)

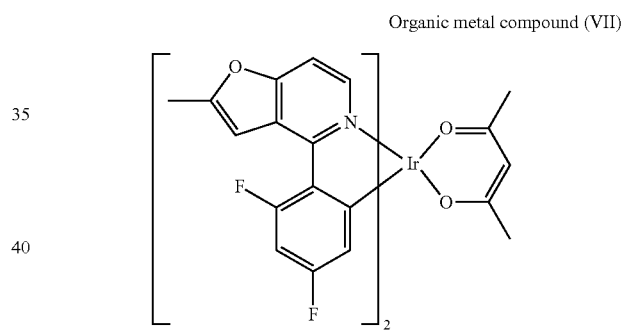

Organic metal compound (VII)

130 mmol of nitromethane, 52 mmol of 5-methyl-2-furaldehyde, and 10 ml methanol were added into a reaction bottle. Next, 130 mL of sodium hydroxide aqueous solution (1 M) were dropwisely added into the reaction bottle at 0° C. After stirring at 0° C. for 15 min, the mixture was added slowly into a hydrochloric acid aqueous solution (50 ml, 8 M). Next, the reaction was terminated after being checked by thin layer chromatography (TLC), and the result was added into a reaction bottle with CH$_2$Cl$_2$ and brine. After extracting, the organic phase was collected. Next, an organic phase was separated and concentrated, and then dried by anhydrous magnesium sulfate. Finally, the result was purified by column chromatography with petroleum ether and ethyl acetate, obtaining Compound (XXIII) with a yield of 70%.

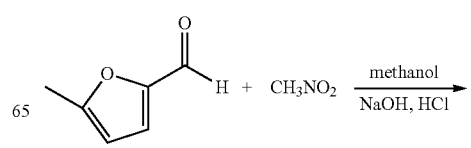

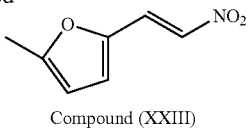

Compound (XXIII)

55.1 mmol of Compound (XXIII), and 200 ml of water were added into the reaction bottle. Next, 82.5 mmol of 2,4-difluorobenzoyl chloride was added into the reaction bottle at 0° C. After the addition was complete, sodium hydroxide aqueous solution (20 wt %) was added into the reaction bottle. After stirring for 8 hr, the mixture was filtrated, obtaining Compound (XXIV). The synthesis pathway of the above reaction was as follows:

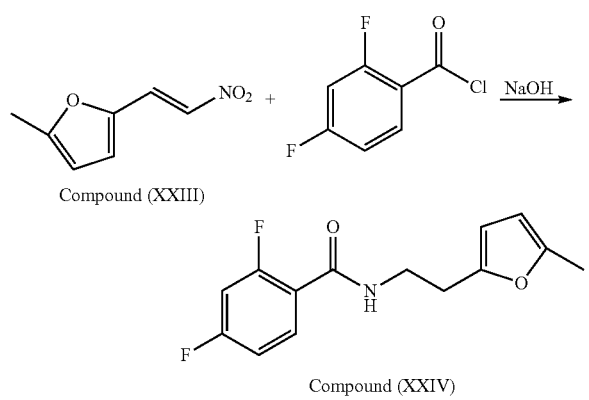

Next, 10 mmol of Compound (XXIV), 20 ml of toluene, and 3 mmol of phosphorus oxychloride (POCl$_3$) were added into the reaction bottle. After heating the reaction bottle for 2 hr, the mixture was neutralized by saturated sodium bicarbonate aqueous solution, and extracted with toluene. After concentrating, Compound (XXV) was obtained. The synthesis pathway of the above reaction was as follows:

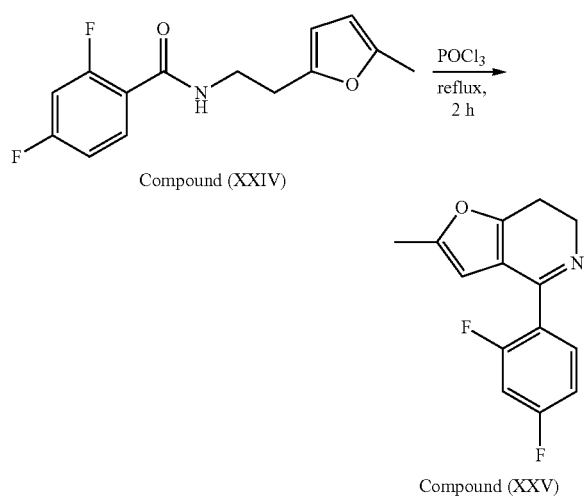

Next, 10 mmol of Compound (XXV), 0.5 g of palladium 10% on carbon (Pd/C catalyst), and 100 ml of toluene were added into the reaction bottle. Next, the reaction bottle was heated to reflux for 18 hr. Next, after removing Pd/C catalyst by filtration, the filtrate was extracted three times using ethyl acetate (EA) and water as the extraction solvent, and an organic phase was separated and concentrated, and then purified by column chromatography, obtaining Compound (XXVI) with a yield of 71%. The synthesis pathway of the above reaction was as follows:

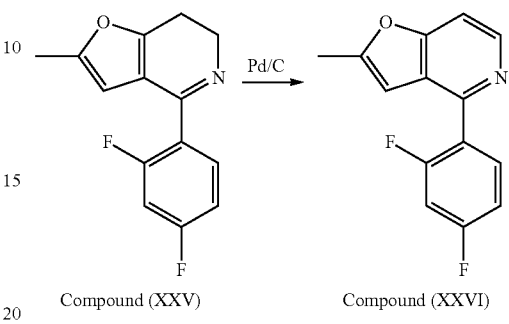

The physical measurement of Compound (XXVI) is listed below: $^1$H-NMR (200 MHz, CDCl$_3$, δ): 8.54-8.51 (d, 1H), 7.82-7.73 (q, 1H), 7.38-7.36 (d, 1H), 7.09-6.91 (m, 2H), 6.43-6.40 (d, 1H), 2.50 (s, 3H).

Next, 1.54 mmol of Compound (XXVI), and 0.7 mmol of iridium trichloride (IrCl$_3$), 15 ml of 2-methoxyethanol, and 5 ml of water were added into the reaction bottle. Next, after removing moisture and purging nitrogen gas several times, the reaction bottle was heated to reflux. After reacting for 24 hr and cooling down to room temperature, the result was filtrated. The filter cake was collected, washed with water and methanol, and dried, obtaining Compound (XXVII). The synthesis pathway of the above reaction was as follows:

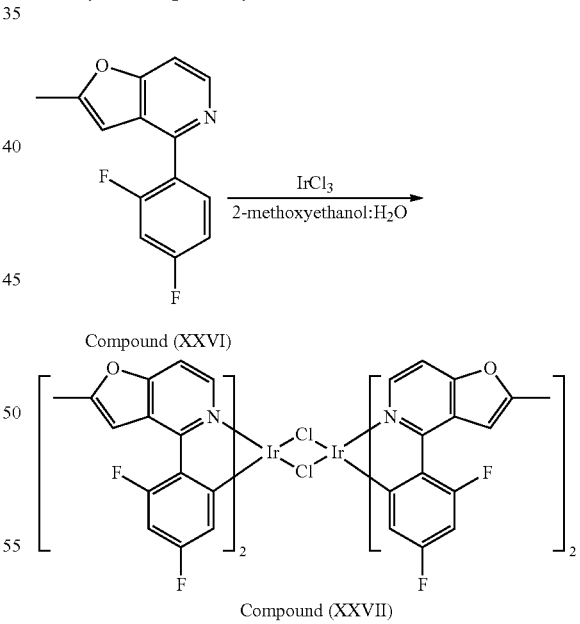

Next, 1 mmol of Compound (XXVII), 3 mmol of acetylacetone, 2 mmol of sodium carbonate (Na$_2$CO$_3$), and 10 ml of 2-methoxyethanol were added into a reaction bottle. Next, after removing moisture and purging nitrogen gas several times, the reaction bottle was heated to 120° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (VII) with a yield of 50%. The synthesis pathway of the above reaction was as follows:

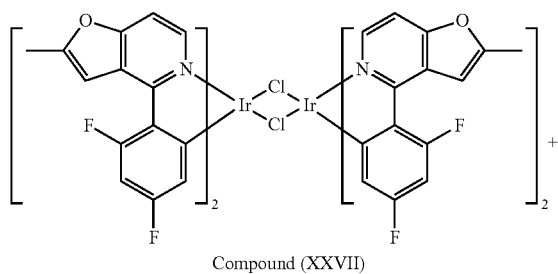

Compound (XXVII)

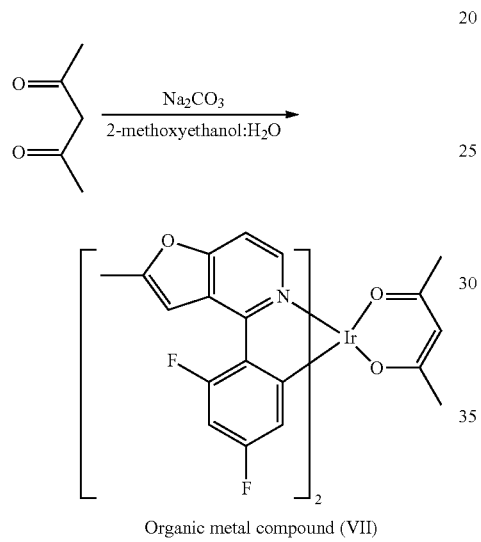

Organic metal compound (VII)

The physical measurement of Organic metal compound (VII) is listed below: $^1$H-NMR (200 MHz, CDCl$_3$, δ): 8.33-8.30 (d, 2H), 7.32-7.28 (d, 2H), 7.14-7.12 (m, 2H), 6.39-6.26 (m, 2H), 5.64-5.59 (m, 2H), 5.23 (s, 1H), 2.58 (s, 6H), 1.77 (s, 6H).

Example 8: Preparation of Organic Metal Compound (VIII)

Organic metal compound (VIII)

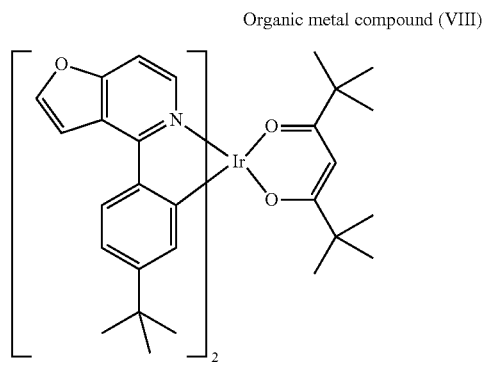

Next, 1 mmol of Compound (XIV), 3 mmol of 2,2,6,6-tetramethylheptane-3,5-dione, 2 mmol of sodium carbonate (Na$_2$CO$_3$), and 10 ml of 2-methoxyethanol were added into a reaction bottle. Next, after removing moisture and purging nitrogen gas several times, the reaction bottle was heated to 120° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (VIII) with a yield of 56%. The synthesis pathway of the above reaction was as follows:

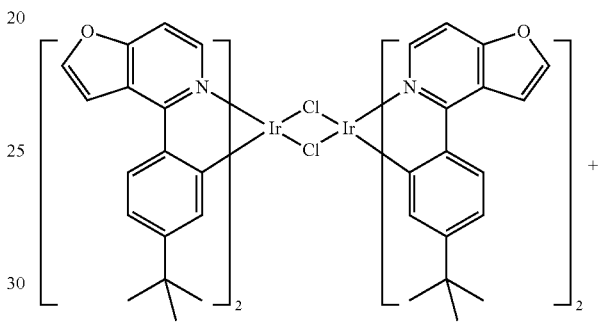

Compound (XIV)

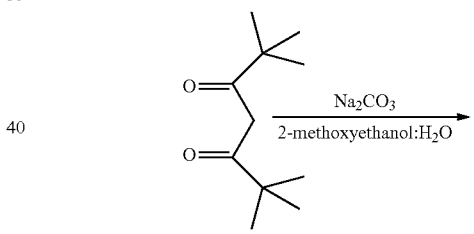

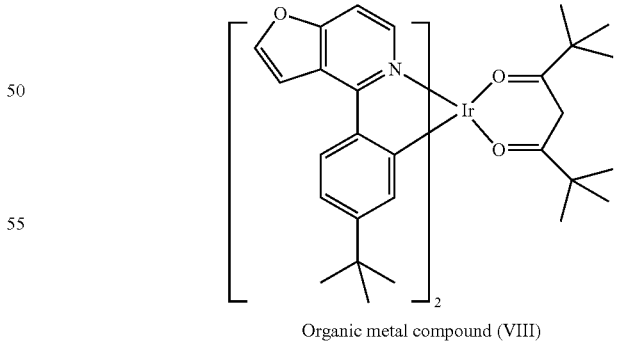

Organic metal compound (VIII)

The physical measurement of Organic metal compound (VIII) is listed below $^1$H-NMR (200 MHz, CDCl$_3$, δ): 8.34-8.31 (d, 2H), 7.83-7.75 (m, 4H), 7.50-7.49 (m, 2H), 7.26-7.23 (d, 2H), 6.91-6.86 (d, 2H), 6.36 (m, 2H), 5.44 (s, 1H), 1.52 (s, 9H), 1.02 (s, 9H), 0.95 (s, 9H).

Example 9: Preparation of Organic Metal Compound (IX)

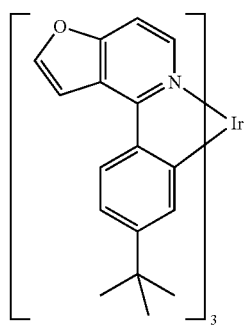

Organic metal compound (IX)

1 mmol of Organic metal compound (III), 1 mmol of Compound (XIII), and 15 mL of glycerol were added into a reaction bottle. Next, after removing moisture and purging nitrogen gas several times, the reaction bottle was heated to 200° C. After reacting for 48 hr and cooling down to room temperature, the result was filtrated. The filter cake was collected and washed with water and dichloromethane, and then purified by column chromatography, obtaining Organic metal compound (IX) with a yield of 35%. The synthesis pathway of the above reaction was as follows:

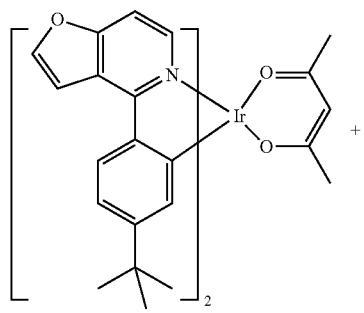

Organic metal compound (III)

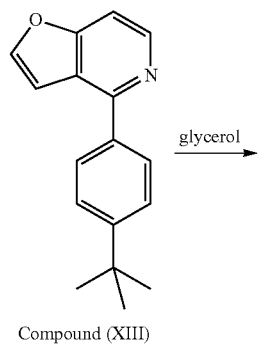

Compound (XIII)

glycerol →

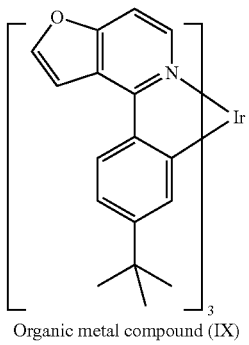

Organic metal compound (IX)

The physical measurement of Organic metal compound (IX) is listed below $^1$H-NMR (200 MHz, CDCl$_3$, δ): 7.94-7.90 (d, 3H), 7.68 (d, 3H), 7.49 (d, 3H), 7.38-7.35 (d, 3H), 7.02-6.95 (m, 9H), 1.10 (s, 27H).

Example 10: Preparation of Organic Metal Compound (X)

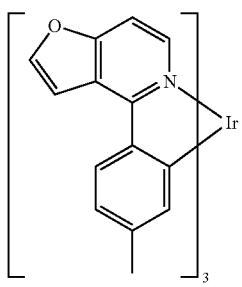

Organic metal compound (X)

1 mmol of Organic metal compound (I), 2 mmol of Compound (V), and 15 mL of glycerol were added into a reaction bottle. Next, after removing moisture and purging nitrogen gas several times, the reaction bottle was heated to 200° C. After reacting for 48 hr and cooling down to room temperature, the result was filtrated. The filter cake was collected and washed with water and ethyl acetate (EA), and then purified by column chromatography, obtaining Organic metal compound (X). The synthesis pathway of the above reaction was as follows:

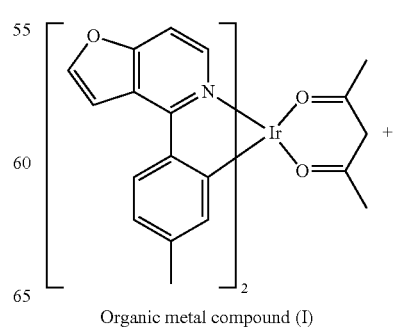

Organic metal compound (I)

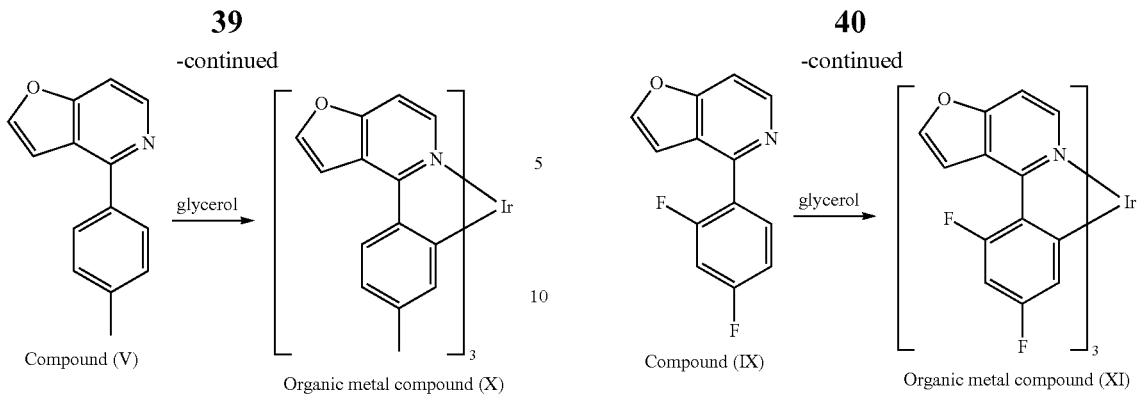

The physical measurement of Organic metal compound (X) is listed below $^1$H NMR (200 MHz, CDCl$_3$, 294 K): 7.92 (d, 3H), 7.70 (d, 3H), 7.52 (d, 3H), 7.32 (d, 3H), 6.97 (d, 3H), 6.77~6.74 (m, 6H), 2.14 (s, 9H).

The physical measurement of Organic metal compound (XI) is listed below $^1$H NMR (200 MHz, CDCl$_3$, 294 K): 7.70 (d, 3H), 7.49 (s, 3H), 7.34 (d, 3H), 7.11 (d, 3H), 6.48~6.28 (m, 6H).

Example 11: Preparation of Organic Metal Compound (XI)

Example 12: Preparation of Organic Metal Compound XII)

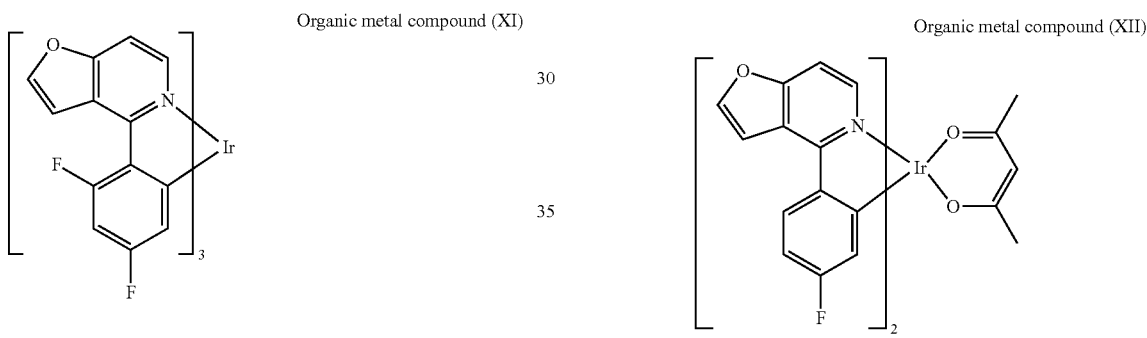

1 mmol of Organic metal compound (II), 2 mmol of Compound (IX), and 15 mL of glycerol were added into a reaction bottle. Next, after removing moisture and purging nitrogen gas several times, the reaction bottle was heated to 200° C. After reacting for 48 hr and cooling down to room temperature, the result was filtrated. The filter cake was collected and washed with water and ethyl acetate (EA), and then purified by column chromatography, obtaining Organic metal compound (XI). The synthesis pathway of the above reaction was as follows:

4.2 mmol of Compound (XXX), 2 mmol of iridium trichloride (IrCl$_3$), 15 ml of 2-methoxyethanol, and 5 ml of water were added into the reaction bottle. Next, after removing moisture and purging nitrogen gas several times, the reaction bottle was heated to reflux. After reacting for 24 hr and cooling down to room temperature, the result was filtrated. The filter cake was collected, washed with water and methanol, and dried, obtaining Compound (XXXI). The synthesis pathway of the above reaction was as follows:

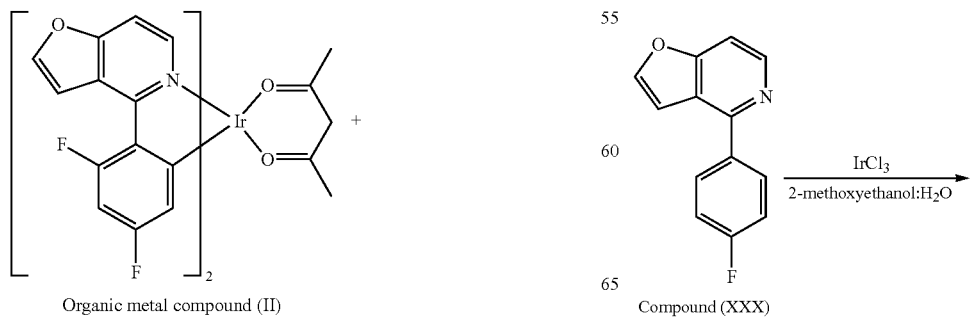

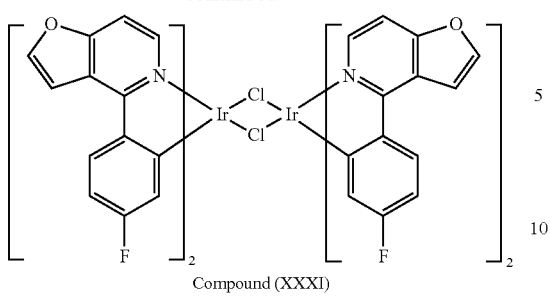

Compound (XXXI)

Next, 1 mmol of Compound (XXXI), 3 mmol of acetylacetone, 2 mmol of sodium carbonate ($Na_2CO_3$), and 10 ml of 2-methoxyethanol were added into a reaction bottle. Next, after removing moisture and purging nitrogen gas several times, the reaction bottle was heated to 120° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XII). The synthesis pathway of the above reaction was as follows:

Example 13: Preparation of Organic Metal Compound (XIII)

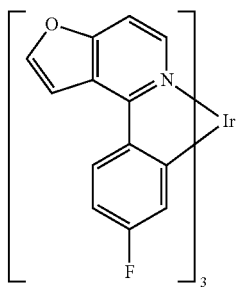

Organic metal compound (XIII)

1 mmol of Organic metal compound (XII), 2 mmol of Compound (XXX), and 15 mL of glycerol were added into a reaction bottle. Next, after removing moisture and purging nitrogen gas several times, the reaction bottle was heated to 200° C. After reacting for 48 hr and cooling down to room temperature, the result was filtrated. The filter cake was collected and washed with water and ethyl acetate (EA), and then purified by column chromatography, obtaining Organic metal compound (XIII). The synthesis pathway of the above reaction was as follows:

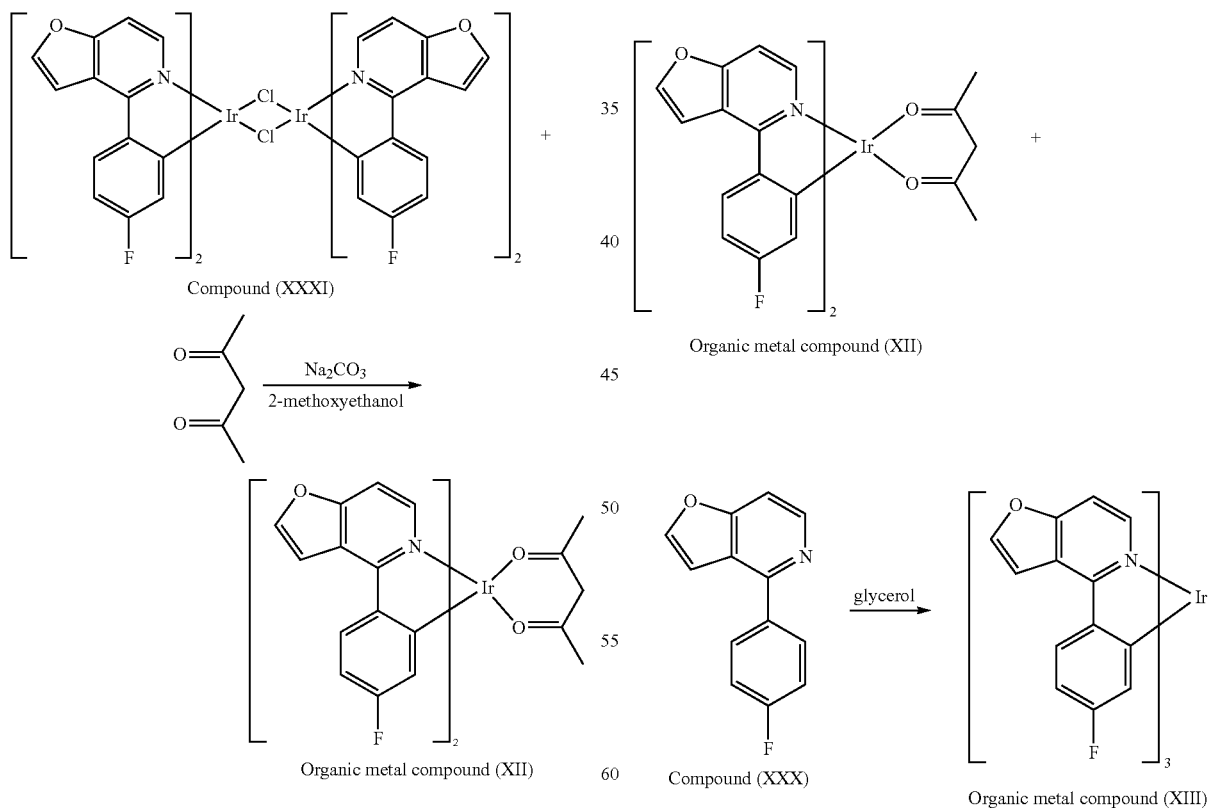

The physical measurement of Organic metal compound (XII) is listed below $^1$H NMR (500 MHz, $CDCl_3$, 294 K): 8.37 (d, 2H), 7.90 (dd, 2H), 7.83 (s, 2H), 7.47 (s, 2H), 7.37 (d, 2H), 6.60 (dd, 2H), 5.87 (d, 2H), 5.25 (s, 1H), 1.80 (d, 6H).

The physical measurement of Organic metal compound (XIII) is listed below $^1$H NMR (500 MHz, $CDCl_3$, 294 K): 8.00 (dd, 3H), 7.77 (d, 3H), 7.49 (d, 3H), 7.34 (d, 3H), 7.06 (d, 3H), 6.67 (dd, 3H), 6.53 (dd, 3H).

Example 14: Preparation of Organic Metal Compound (XIV)

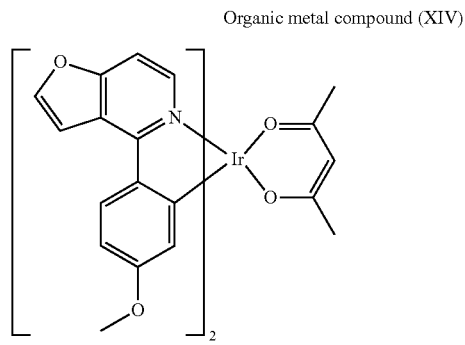

Organic metal compound (XIV)

4.2 mmol of Compound (XXXII), 2 mmol of iridium trichloride (IrCl$_3$), 15 ml of 2-methoxyethanol, and 5 ml of water were added into the reaction bottle. Next, after removing moisture and purging nitrogen gas several times, the reaction bottle was heated to reflux. After reacting for 24 hr and cooling down to room temperature, the result was filtrated. The filter cake was collected, washed with water and methanol, and dried, obtaining Compound (XXXIII). The synthesis pathway of the above reaction was as follows:

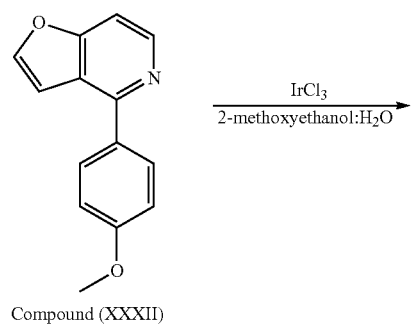

Compound (XXXII)

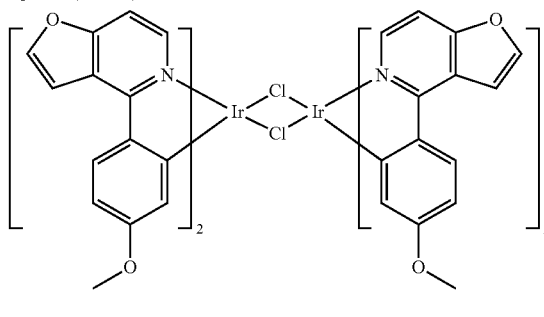

Compound (XXXIII)

Next, 1 mmol of Compound (XXXIII), 3 mmol of acetylacetone, 2 mmol of sodium carbonate (Na$_2$CO$_3$), and 10 ml of 2-methoxyethanol were added into a reaction bottle. Next, after removing moisture and purging nitrogen gas several times, the reaction bottle was heated to 120° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XIV). The synthesis pathway of the above reaction was as follows:

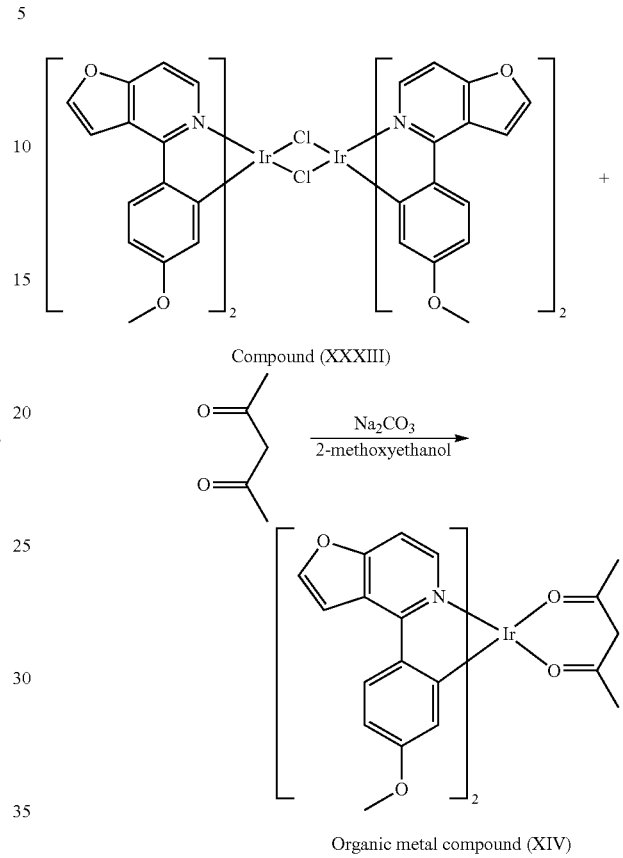

Organic metal compound (XIV)

The physical measurement of Organic metal compound (XIII) is listed below $^1$H NMR (500 MHz, CDCl$_3$, 294 K): 8.37 (d, 2H), 7.86 (d, 2H), 7.77 (s, 2H), 7.45 (s, 2H), 7.26 (d, 2H), 6.45 (d, 2H), 5.78 (s, 2H), 5.21 (s, 1H), 3.51 (s, 6H), 1.77 (s, 6H).

Example 15: Preparation of Organic Metal Compound (XV)

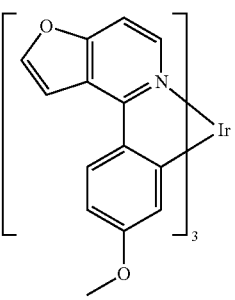

Organic metal compound (XV)

1 mmol of Organic metal compound (XIV), 2 mmol of Compound (XXXII), and 15 mL of glycerol were added into a reaction bottle. Next, after removing moisture and purging nitrogen gas several times, the reaction bottle was heated to 200° C. After reacting for 48 hr and cooling down to room temperature, the result was filtrated. The filter cake was collected and washed with water and ethyl acetate (EA), and then purified by column chromatography, obtaining Organic metal compound (XV). The synthesis pathway of the above reaction was as follows:

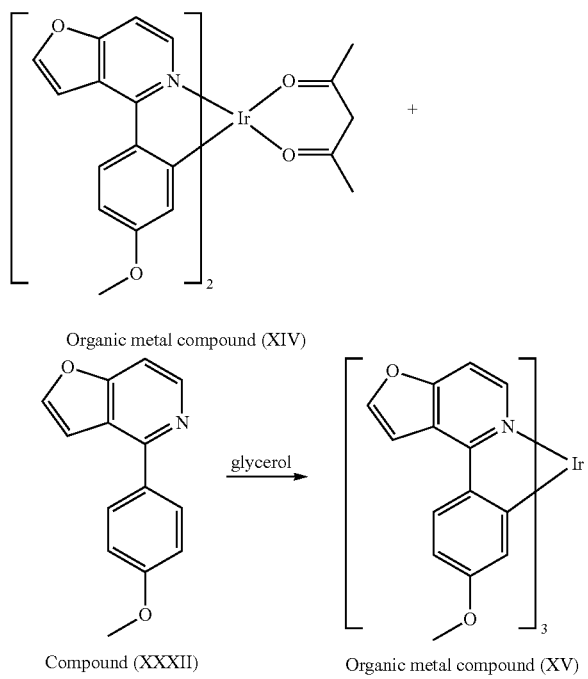

Compound (XXXII)  Organic metal compound (XV)

The physical measurement of Organic metal compound (XV) is listed below $^1$H NMR (500 MHz, CDCl$_3$, 294 K): 7.94 (d, 3H), 7.70 (s, 3H), 7.46 (s, 3H), 7.33 (d, 3H), 6.97 (d, 3H), 6.51 (d, 6H), 3.55 (s, 9H).

Example 16: Preparation of Organic Metal Compound (XVI)

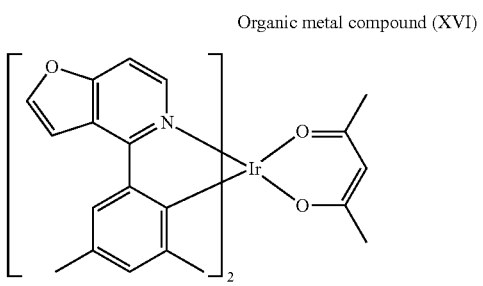

Organic metal compound (XVI)

4.2 mmol of Compound (XXXIV), 2 mmol of iridium trichloride (IrCl$_3$), 15 ml of 2-methoxyethanol, and 5 ml of water were added into the reaction bottle. Next, after removing moisture and purging nitrogen gas several times, the reaction bottle was heated to reflux. After reacting for 24 hr and cooling down to room temperature, the result was filtrated. The filter cake was collected, washed with water and methanol, and dried, obtaining Compound (XXXV). The synthesis pathway of the above reaction was as follows:

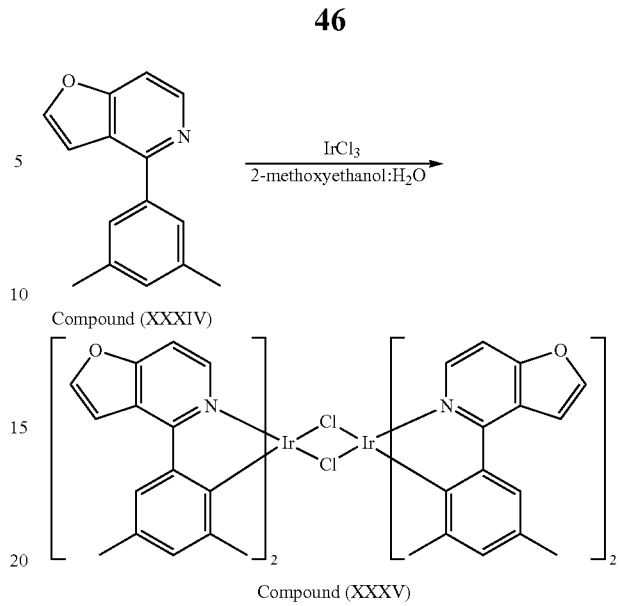

Next, 1 mmol of Compound (XXXV), 3 mmol of acetylacetone, 2 mmol of sodium carbonate (Na$_2$CO$_3$), and 10 ml of 2-methoxyethanol were added into a reaction bottle. Next, after removing moisture and purging nitrogen gas several times, the reaction bottle was heated to 120° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XVI). The synthesis pathway of the above reaction was as follows:

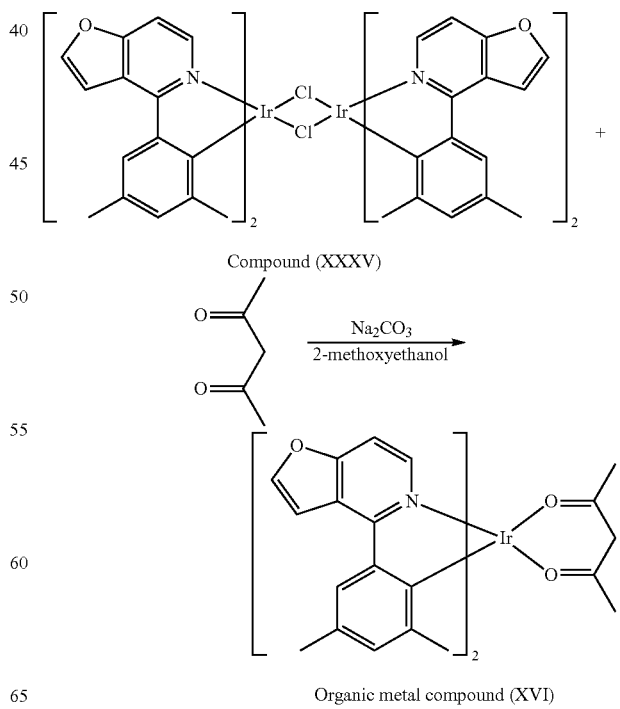

Organic metal compound (XVI)

The physical measurement of Organic metal compound (XVI) is listed below $^1$H NMR (500 MHz, CDCl$_3$, 294 K): 8.30 (d, 2H), 7.77 (d, 2H), 7.75 (s, 2H), 7.60 (d, 2H), 7.17 (d, 2H), 6.50 (s, 2H), 5.03 (s, 1H), 2.30 (s, 6H), 1.62 (s, 6H), 1.32 (s, 6H).

Example 17: Preparation of Organic Metal Compound (XVII)

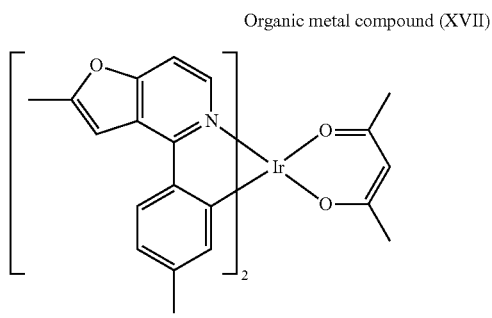

Organic metal compound (XVII)

4.2 mmol of Compound (XXXVI), 2 mmol of iridium trichloride (IrCl$_3$), 15 ml of 2-methoxyethanol, and 5 ml of water were added into the reaction bottle. Next, after removing moisture and purging nitrogen gas several times, the reaction bottle was heated to reflux. After reacting for 24 hr and cooling down to room temperature, the result was filtrated. The filter cake was collected, washed with water and methanol, and dried, obtaining Compound (XXXVII). The synthesis pathway of the above reaction was as follows:

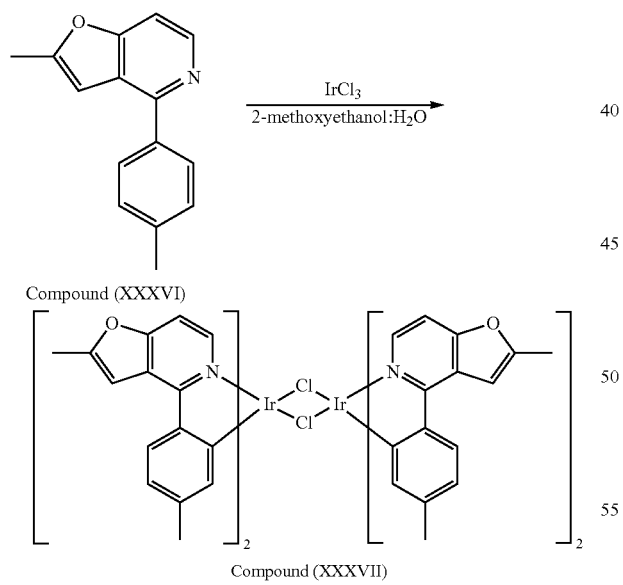

Next, 1 mmol of Compound (XXXVII), 3 mmol of acetylacetone, 2 mmol of sodium carbonate (Na$_2$CO$_3$), and 10 ml of 2-methoxyethanol were added into a reaction bottle. Next, after removing moisture and purging nitrogen gas several times, the reaction bottle was heated to 120° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XVII). The synthesis pathway of the above reaction was as follows:

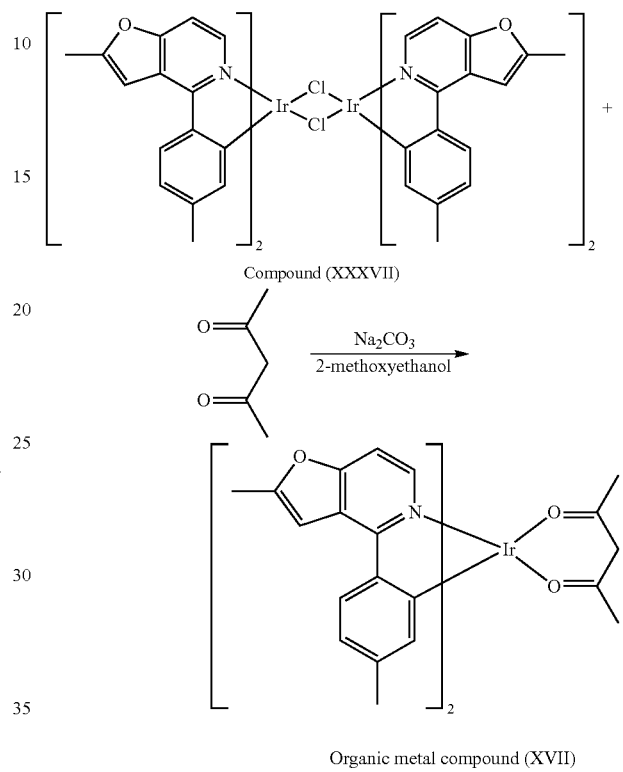

The physical measurement of Organic metal compound (XVII) is listed below: $^1$H NMR (500 MHz, CDCl$_3$, 294 K): 8.32 (d, 2H), 7.74 (d, 2H), 7.21 (d, 2H), 7.19 (s, 2H), 6.64 (d, 2H), 6.08 (s, 2H), 5.18 (s, 1H), 2.60 (s, 6H), 2.03 (s, 6H), 1.74 (s, 6H).

Example 18: Preparation of Organic Metal Compound (XVIII)

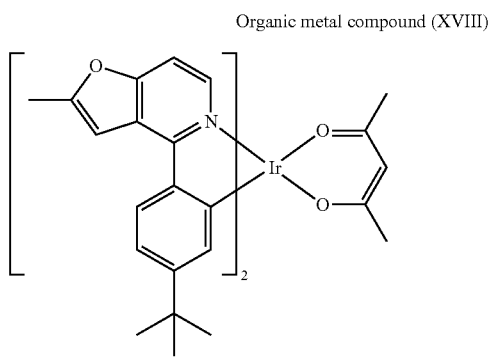

Organic metal compound (XVIII)

4.2 mmol of Compound (XXXVIII), 2 mmol of iridium trichloride (IrCl$_3$), 15 ml of 2-methoxyethanol, and 5 ml of water were added into the reaction bottle. Next, after removing moisture and purging nitrogen gas several times, the reaction bottle was heated to reflux. After reacting for 24 hr and cooling down to room temperature, the result was filtrated. The filter cake was collected, washed with water and methanol, and dried, obtaining Compound (XXXIX). The synthesis pathway of the above reaction was as follows:

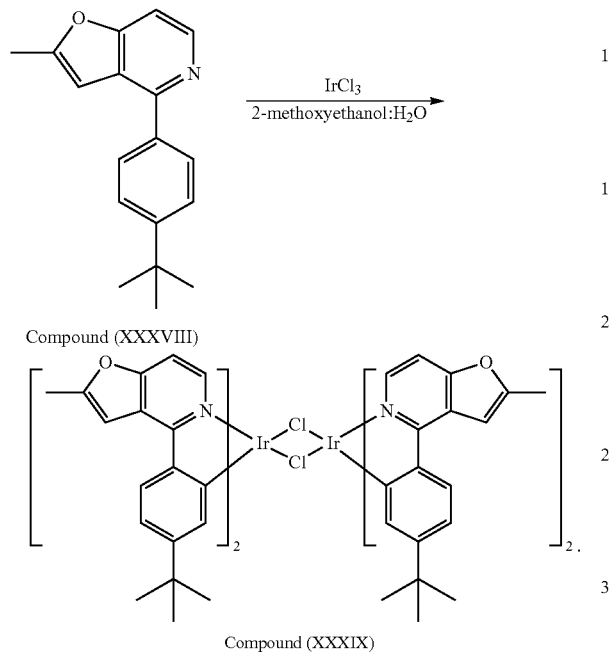

Compound (XXXVIII)

Compound (XXXIX)

Next, 1 mmol of Compound (XXXIX), 3 mmol of acetylacetone, 2 mmol of sodium carbonate ($Na_2CO_3$), and 10 ml of 2-methoxyethanol were added into a reaction bottle. Next, after removing moisture and purging nitrogen gas several times, the reaction bottle was heated to 120° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XVIII). The synthesis pathway of the above reaction was as follows:

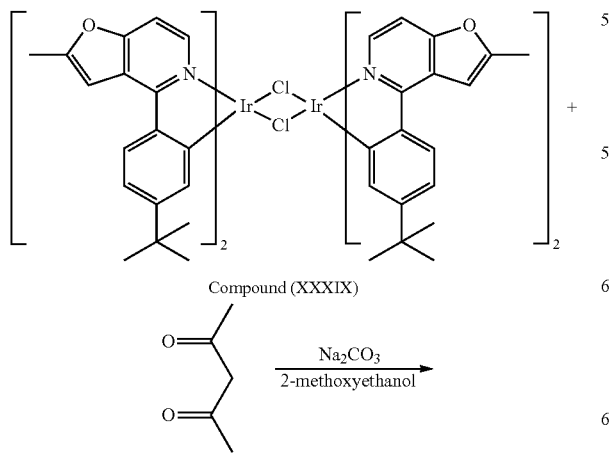

Compound (XXXIX)

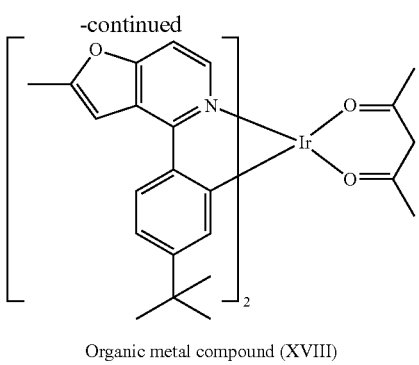

Organic metal compound (XVIII)

The physical measurement of Organic metal compound (XVIII) is listed below: $^1$H NMR (500 MHz, $CDCl_3$, 294 K): 8.36 (d, 2H), 7.75 (d, 2H), 7.23 (d, 2H), 7.09 (s, 2H), 6.86 (d, 2H), 6.23 (s, 2H), 5.19 (s, 1H), 2.61 (s, 6H), 1.76 (s, 6H), 1.00 (s, 18H).

Example 19: Preparation of Organic Metal Compound (XIX)

Organic metal compound (XIX)

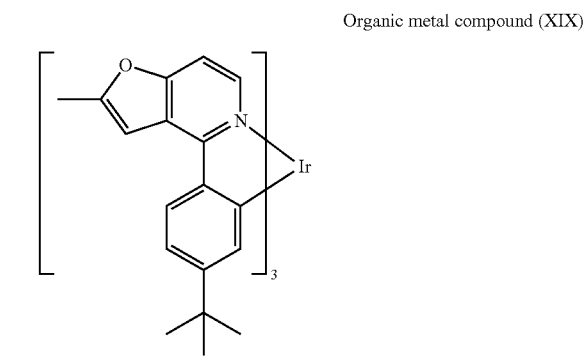

1 mmol of Organic metal compound (XVIII), 2 mmol of Compound (XXXVIII), and 15 mL of glycerol were added into a reaction bottle. Next, after removing moisture and purging nitrogen gas several times, the reaction bottle was heated to 200° C. After reacting for 48 hr and cooling down to room temperature, the result was filtrated. The filter cake was collected and washed with water and ethyl acetate (EA), and then purified by column chromatography, obtaining Organic metal compound (XIX). The synthesis pathway of the above reaction was as follows:

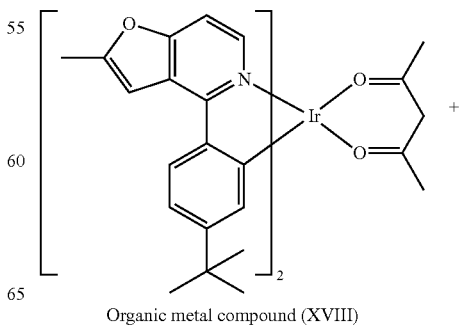

Organic metal compound (XVIII)

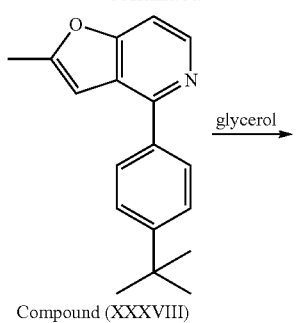

Compound (XXXVIII)

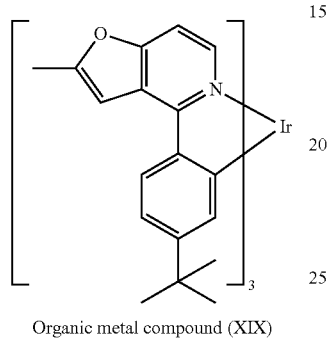

Organic metal compound (XIX)

The physical measurement of Organic metal compound (XIX) is listed below: $^1$H NMR (500 MHz, CDCl$_3$, 294 K): 7.93 (d, 3H), 7.20 (s, 3H), 7.08 (s, 3H), 6.82 (d, 3H), 6.77 (s, 3H), 6.57 (s, 3H), 2.55 (s, 9H), 1.10 (s, 27H).

Example 20: Preparation of Organic Metal Compound (XX)

Organic metal compound (XX)

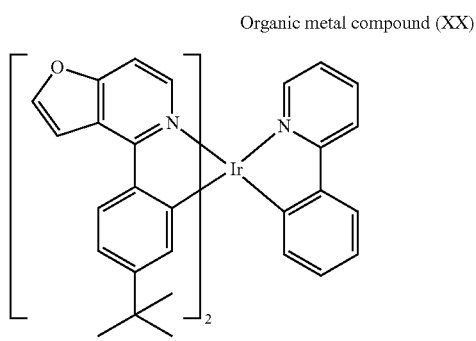

1 mmol of Compound (XIV) and 10 mL of dichloromethane were added into a first reaction bottle. 2.2 mmol of silver trifluoromethanesulfonate (AgOTf) and 5 mL of methanol were added into a second reaction bottle, obtaining a methanol solution. Next, the methanol solution was added into the first reaction bottle, and the mixture was stirred for 18 hr. Next, after filtrating for removing sliver chloride and concentrating, Compound (XL) is obtained. The synthesis pathway of the above reaction was as follows:

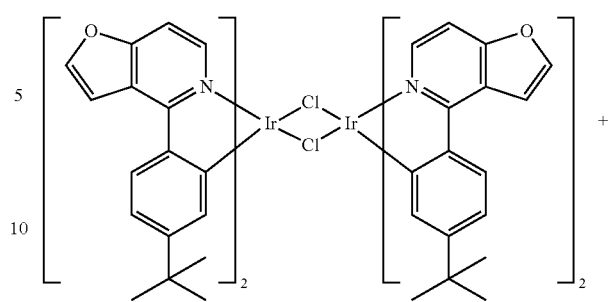

Compound (XIV)

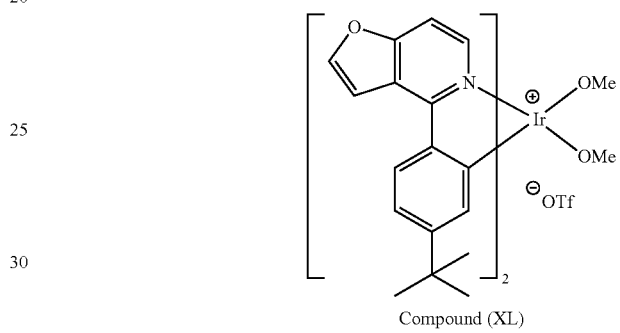

Compound (XL)

Next, 1 mmol of Compound (XL), 2.5 mmol of Compound (XLI), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XX). The synthesis pathway of the above reaction was as follows:

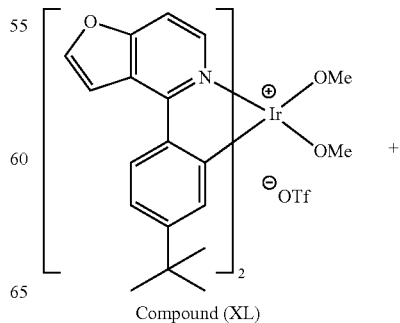

Compound (XL)

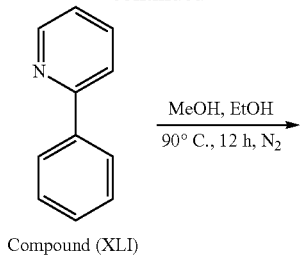

Compound (XLI)

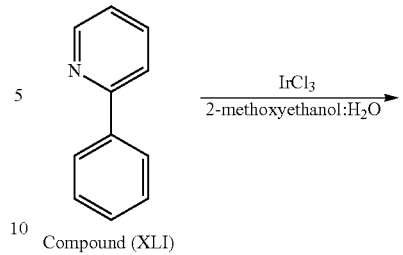

Compound (XLI)

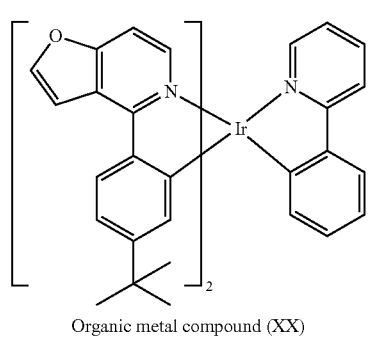

Organic metal compound (XX)

The physical measurement of Organic metal compound (XX) is listed below: $^1$H NMR (500 MHz, CDCl$_3$, 294 K): 7.94 (t, 2H), 7.87 (d, 1H), 7.68~7.65 (m, 3H), 7.56 (t, 1H), 7.54~7.46 (m, 3H), 7.41 (d, 1H), 7.35 (d, 1H), 7.02 (d, 1H), 6.98~6.83 (m, 7H), 6.82 (s, 1H), 1.12 (s, 9H), 1.08 (s, 9H).

Example 21: Preparation of Organic Metal Compound (XXI)

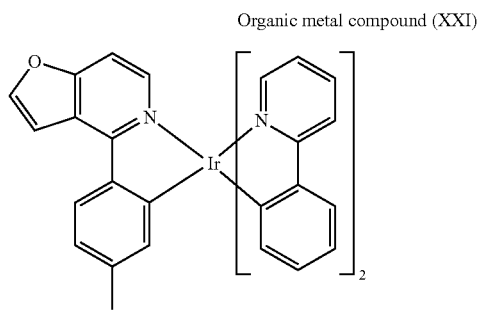

Organic metal compound (XXI)

4.2 mmol of Compound (XLI), 2 mmol of iridium trichloride (IrCl$_3$), 15 ml of 2-methoxyethanol, and 5 ml of water were added into the reaction bottle. Next, after removing moisture and purging nitrogen gas several times, the reaction bottle was heated to reflux. After reacting for 24 hr and cooling down to room temperature, the result was filtrated. The filter cake was collected, washed with water and methanol, and dried, obtaining Compound (XLII). The synthesis pathway of the above reaction was as follows:

Compound (XLII)

1 mmol of Compound (XLII) and 10 mL of dichloromethane were added into a first reaction bottle. 2.2 mmol of silver trifluoromethanesulfonate (AgOTf) and 5 mL of methanol were added into a second reaction bottle, obtaining a methanol solution. Next, the methanol solution was added into the first reaction bottle, and the mixture was stirred for 18 hr. Next, after filtrating for removing sliver chloride and concentrating, Compound (XLIII) is obtained. The synthesis pathway of the above reaction was as follows:

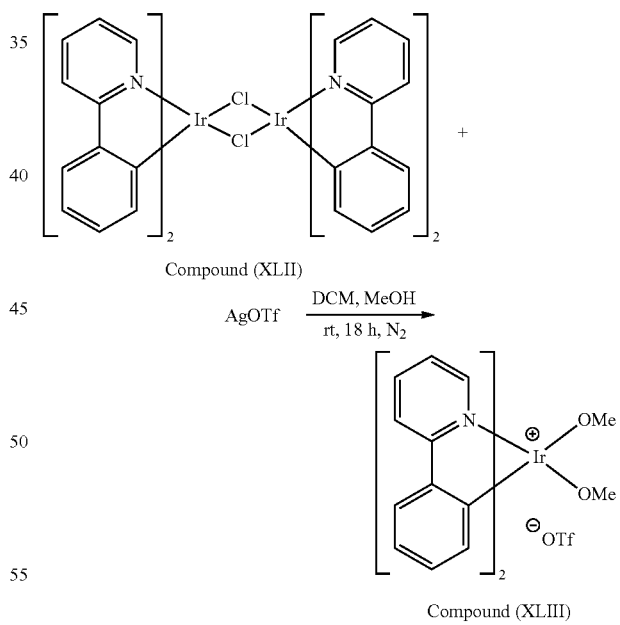

Compound (XLIII)

Next, 1 mmol of Compound (XLIII), 2.5 mmol of Compound (V), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water.

Next, an organic phase was separated and concentrated, and then purified by column chromatography, obtaining Organic metal compound (XXI). The synthesis pathway of the above reaction was as follows:

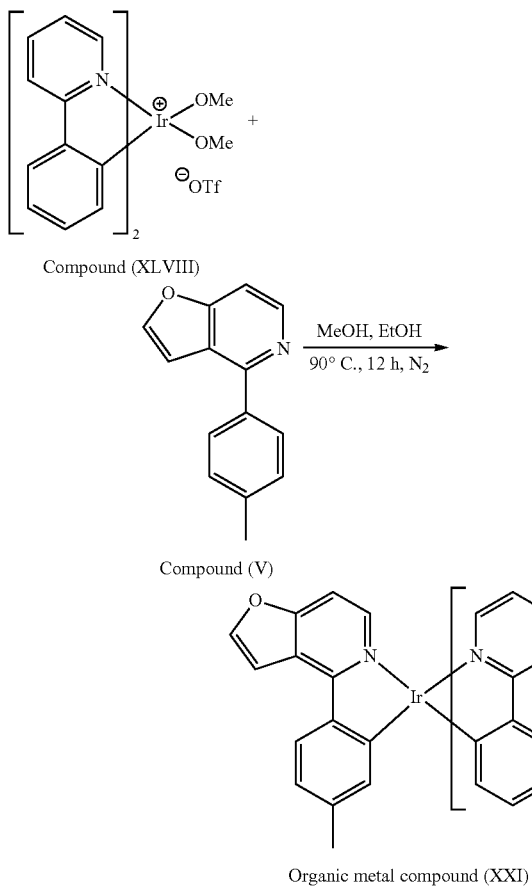

Compound (XLVIII)

Compound (V)

Organic metal compound (XXI)

The physical measurement of Organic metal compound (XXI) is listed below: $^1$H NMR (500 MHz, CDCl$_3$, 294 K): 7.92 (d, 1H), 7.86 (d, 2H), 7.69 (s, 1H), 7.66 (d, 2H), 7.58~7.56 (m, 2H), 7.50 (m, 2H), 7.45 (d, 1H), 7.38 (d, 1H), 7.01 (d, 1H), 6.90~6.80 (m, 8H), 6.77 (d, 1H), 6.72 (s, 1H), 2.15 (s, 3H).

Example 22: Preparation of Organic Metal Compound (XXII)

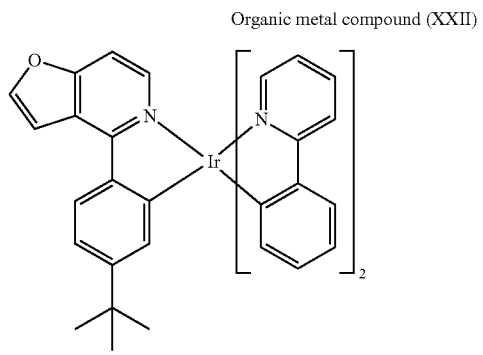

Organic metal compound (XXII)

1 mmol of Compound (XLIII), 2.5 mmol of Compound (XIII), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXII). The synthesis pathway of the above reaction was as follows:

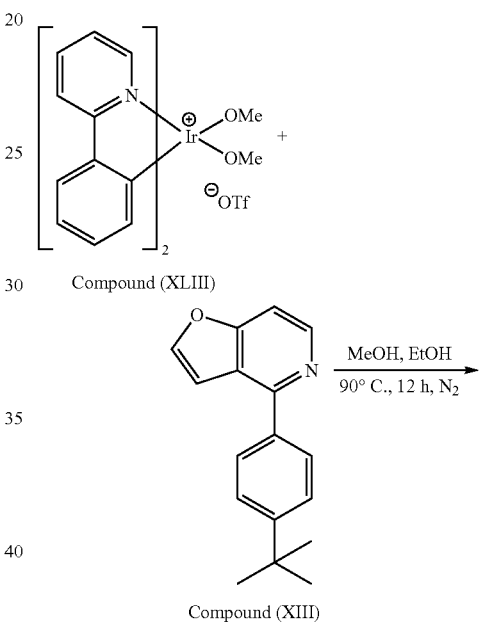

Compound (XLIII)

Compound (XIII)

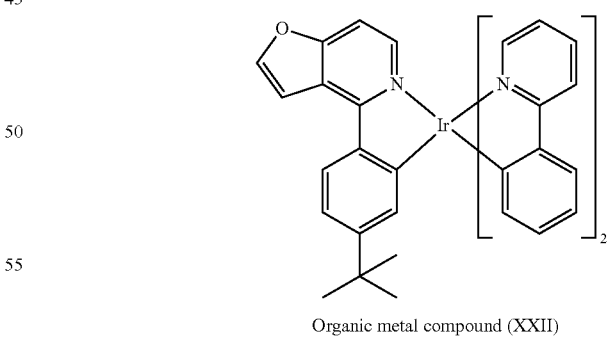

Organic metal compound (XXII)

The physical measurement of Organic metal compound (XXII) is listed below: $^1$H NMR (500 MHz, Acetone-d$_6$, 294 K): 8.09~8.02 (m, 4H), 7.78~7.71 (m, 5H), 7.67 (d, 1H), 7.64 (d, 1H), 7.55 (d, 1H), 7.27 (d, 1H), 7.06 (t, 1H), 7.00 (t, 1H), 6.97 (d, 1H), 6.92 (dd, 1H), 6.87 (d, 1H), 6.83~6.80 (m, 2H), 6.77 (t, 1H), 6.72 (t, 1H), 6.66 (t, 1H), 1.03 (s, 9H).

Example 23: Preparation of Organic Metal Compound (XXIII)

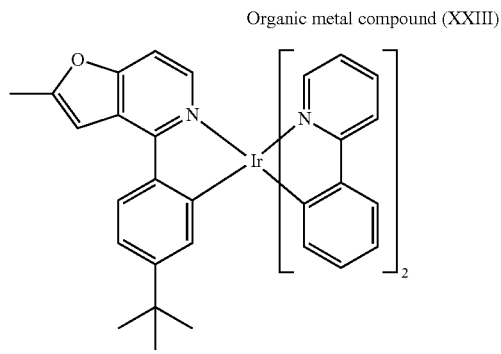

Organic metal compound (XXIII)

1 mmol of Compound (XLIII), 2.5 mmol of Compound (XXXVIII), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXIII). The synthesis pathway of the above reaction was as follows:

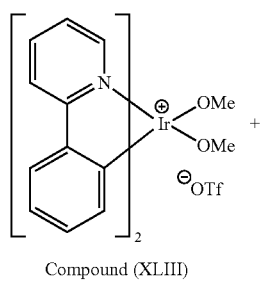

Compound (XLIII)

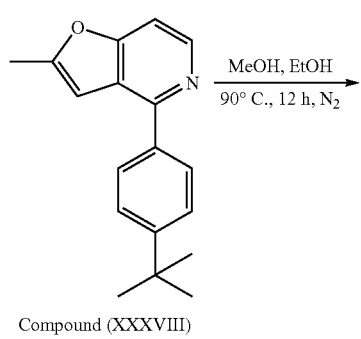

Compound (XXXVIII)

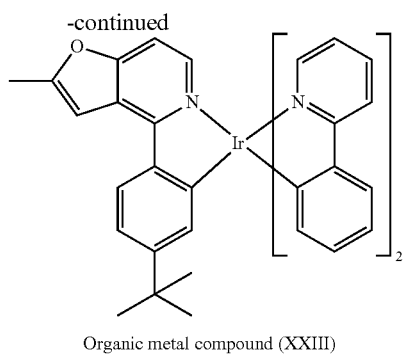

Organic metal compound (XXIII)

The physical measurement of Organic metal compound (XXIII) is listed below: $^1$H NMR (500 MHz, CDCl$_3$, 294 K): 7.92~7.85 (m, 3H), 7.67 (t, 2H), 7.59~7.50 (m, 3H), 7.43 (s, 1H), 7.28 (s, 1H), 7.09 (s, 1H), 6.88~6.62 (m, 11H), 2.54 (s, 3H), 1.09 (s, 9H).

Example 24: Preparation of Organic Metal Compound (XXIV)

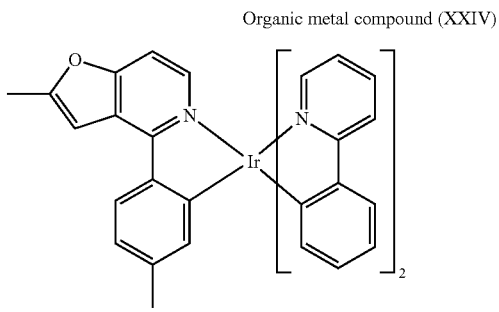

Organic metal compound (XXIV)

1 mmol of Compound (XLIII), 2.5 mmol of Compound (XXXVI), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXIV). The synthesis pathway of the above reaction was as follows:

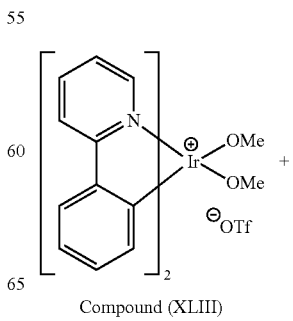

Compound (XLIII)

-continued

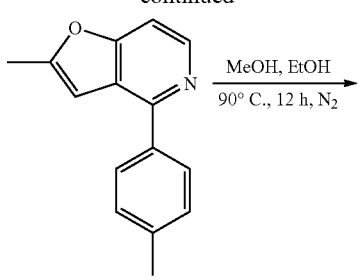

Compound (XXXVI)

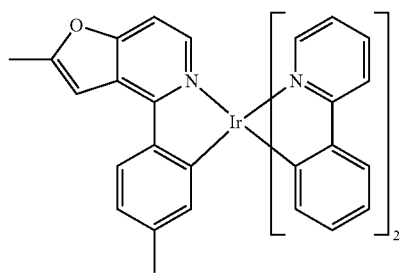

Organic metal compound (XXIV)

The physical measurement of Organic metal compound (XXIV) is listed below: $^1$H NMR (500 MHz, Acetone-d$_6$, 294 K): 8.07 (d, 2H), 7.95 (d, 1H), 7.76~7.70 (m, 4H), 7.61 (d, 1H), 7.58 (d, 1H), 7.45 (d, 1H), 7.37 (s, 1H), 7.16 (d, 1H), 7.08 (dd, 1H), 7.00 (dd, 1H), 6.86~6.76 (m, 4H), 6.73 (s, 1H), 6.70~6.65 (m, 3H), 2.56 (s, 3H), 2.02 (s, 3H.

Example 25: Preparation of Organic Metal Compound (XXV)

Organic metal compound (XXV)

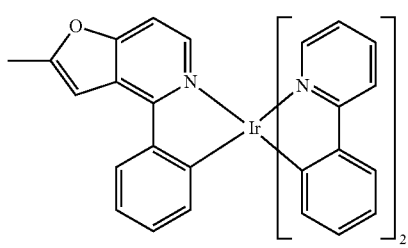

1 mmol of Compound (XLIII), 2.5 mmol of Compound (XLII), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXV). The synthesis pathway of the above reaction was as follows:

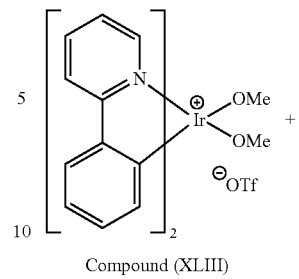

Compound (XLIII)

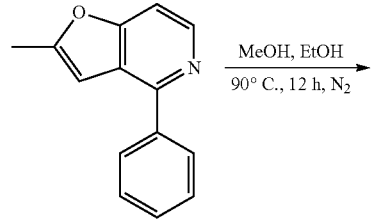

Compound (XLII)

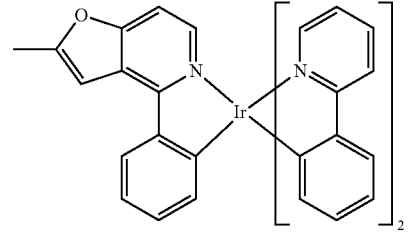

Organic metal compound (XXV)

The physical measurement of Organic metal compound (XXV) is listed below: $^1$H NMR (500 MHz, Acetone-d$_6$, 294 K): 8.08~8.05 (m, 3H), 7.77~7.71 (m, 4H), 7.65 (d, 1H), 7.59 (d, 1H), 7.50 (d, 1H), 7.42 (s, 1H), 7.20 (d, 1H), 7.66 (dd, 1H), 7.00 (dd, 1H), 6.89~6.76 (m, 6H), 6.71~6.65 (m, 3H).

Example 26: Preparation of Organic Metal Compound (XXVI)

Organic metal compound (XXVI)

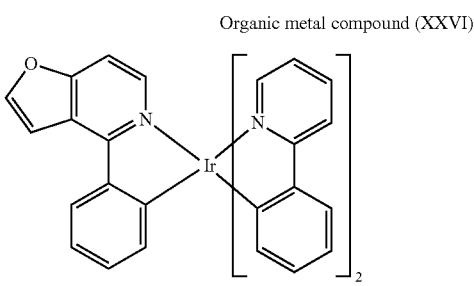

1 mmol of Compound (XLIII), 2.5 mmol of Compound (XVII), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXVI). The synthesis pathway of the above reaction was as follows:

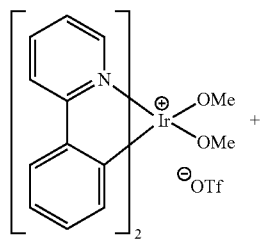

Compound (XLIII)

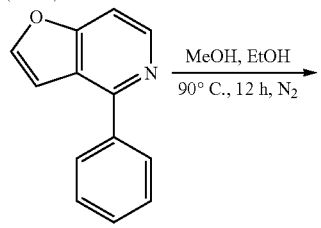

Compopund (XVII)

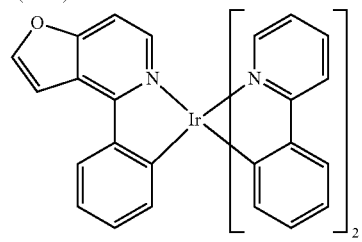

Organic metal compound (XXVI)

The physical measurement of Organic metal compound (XXVI) is listed below: $^1$H NMR (500 MHz, Acetone-$d_6$, 294 K): 8.15 (d, 1H), 8.09~8.07 (m, 3H), 7.80 (s, 1H), 7.76~7.71 (m, 4H), 7.65 (d, 1H), 7.60 (d, 1H), 7.58 (d, 1H), 7.32 (d, 1H), 7.06 (dd, 1H), 7.00 (dd, 1H), 6.91~6.87 (m, 2H), 6.82~6.77 (m, 4H), 6.72~6.66 (m, 3H).

Example 27: Preparation of Organic Metal Compound (XXVII)

Organic metal compound (XXVII)

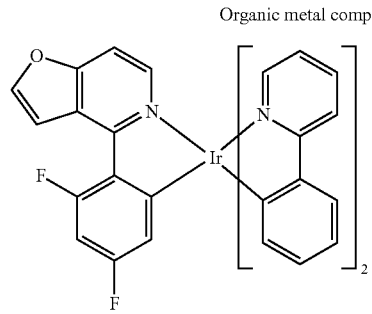

1 mmol of Compound (XLIII), 2.5 mmol of Compound (IX), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXVII). The synthesis pathway of the above reaction was as follows:

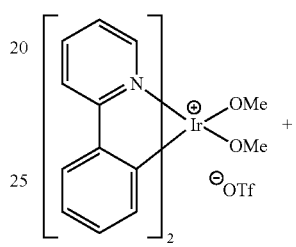

Compound (XLIII)

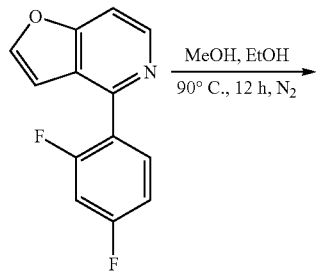

Compound (IX)

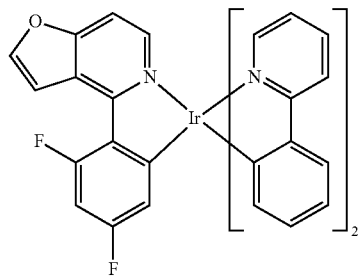

Organic metal compound (XXVII)

The physical measurement of Organic metal compound (XXVII) is listed below: $^1$H NMR (500 MHz, Acetone-$d_6$, 294 K): 8.11 (t, 2H), 8.01 (d, 1H), 7.82~7.73 (m, 4H), 7.68 (d, 1H), 7.60 (d, 1H), 7.56 (d, 1H), 7.47~7.46 (m, 1H), 7.39 (d, 1H), 7.08~7.04 (m, 2H), 6.86~6.81 (m, 2H), 6.76~6.71 (m, 4H), 6.48~6.41 (m, 2H).

Example 28: Preparation of Organic Metal Compound (XXVIII)

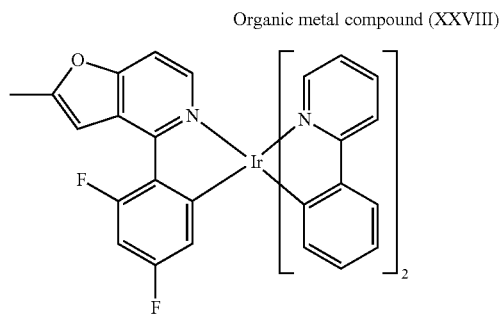

Organic metal compound (XXVIII)

1 mmol of Compound (XLIII), 2.5 mmol of Compound (XXVI), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXVIII). The synthesis pathway of the above reaction was as follows:

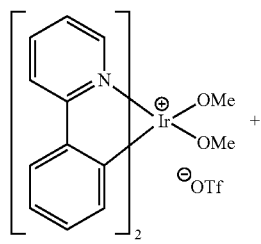

Compound (XLIII)

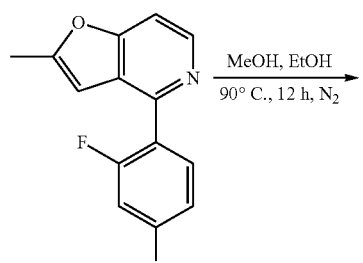

Compound (XXVI)

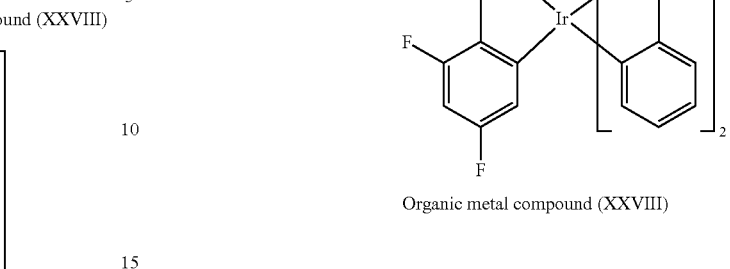

Organic metal compound (XXVIII)

The physical measurement of Organic metal compound (XXVIII) is listed below: $^1$H NMR (500 MHz, Acetone-$d_6$, 294 K): 8.11 (t, 2H), 7.82~7.73 (m, 4H), 7.60 (d, 2H), 7.54 (d, 1H), 7.29 (d, 1H), 7.09~7.04 (m, 3H), 6.86~6.81 (m, 2H), 6.76~6.71 (m, 4H), 6.46~6.40 (m, 2H), 2.54 (s, 3H).

Example 29: Preparation of Organic Metal Compound (XXIX)

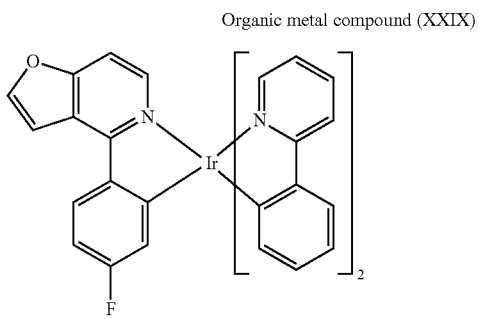

Organic metal compound (XXIX)

1 mmol of Compound (XLIII), 2.5 mmol of Compound (XXX), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXIX). The synthesis pathway of the above reaction was as follows:

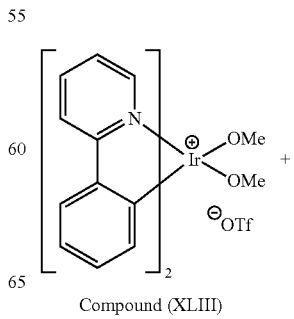

Compound (XLIII)

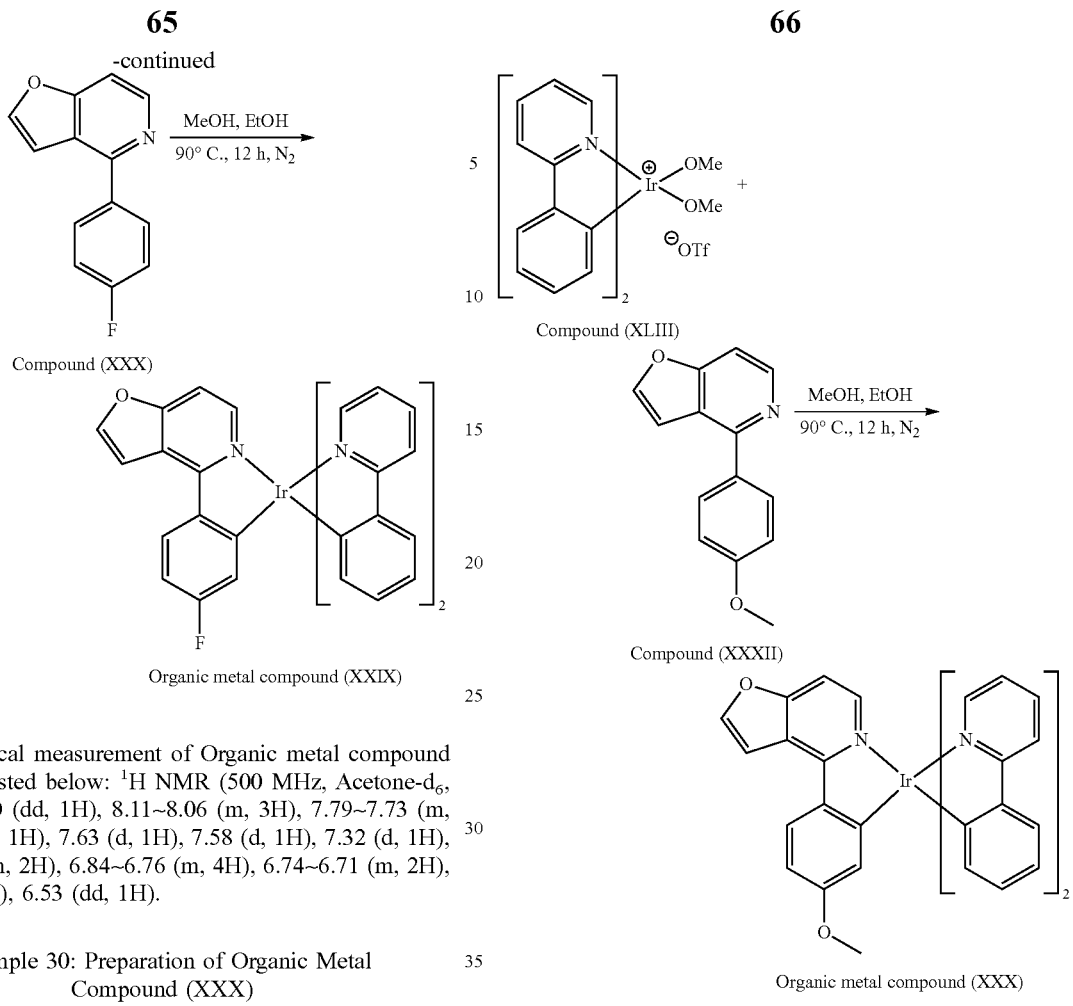

The physical measurement of Organic metal compound (XXIX) is listed below: $^1$H NMR (500 MHz, Acetone-d$_6$, 294 K): 8.20 (dd, 1H), 8.11~8.06 (m, 3H), 7.79~7.73 (m, 5H), 7.65 (d, 1H), 7.63 (d, 1H), 7.58 (d, 1H), 7.32 (d, 1H), 7.09~7.02 (m, 2H), 6.84~6.76 (m, 4H), 6.74~6.71 (m, 2H), 6.62 (dd, 1H), 6.53 (dd, 1H).

Example 30: Preparation of Organic Metal Compound (XXX)

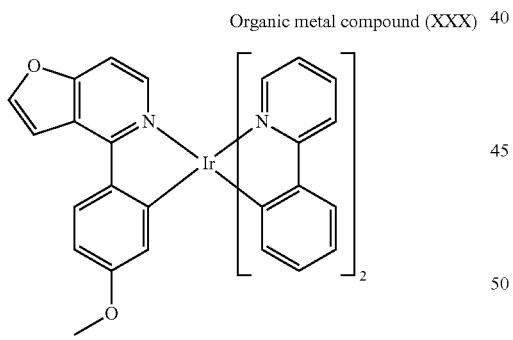

1 mmol of Compound (XLIII), 2.5 mmol of Compound (XXXII), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXX). The synthesis pathway of the above reaction was as follows:

The physical measurement of Organic metal compound (XXX) is listed below: $^1$H NMR (500 MHz, Acetone-d$_6$, 294 K): 8.10~8.07 (m, 3H), 8.05 (d, 1H), 7.78~7.71 (m, 5H), 7.66~7.63 (m, 2H), 7.51 (d, 1H), 7.21 (d, 1H), 7.07~7.00 (m, 2H), 6.88 (d, 1H), 6.84~6.77 (m, 3H), 6.72~6.68 (m, 2H), 6.49 (dd, 1H), 6.43 (d, 1H), 3.48 (s, 3H).

Example 31: Preparation of Organic Metal Compound (XXXI)

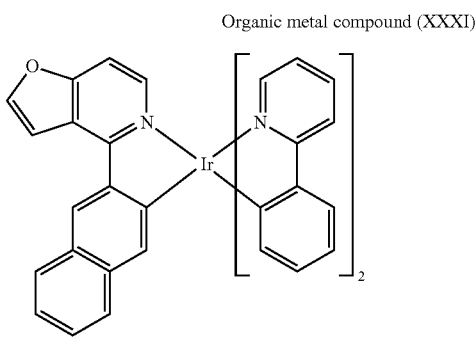

1 mmol of Compound (XLIII), 2.5 mmol of Compound (XXI), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXXI). The synthesis pathway of the above reaction was as follows:

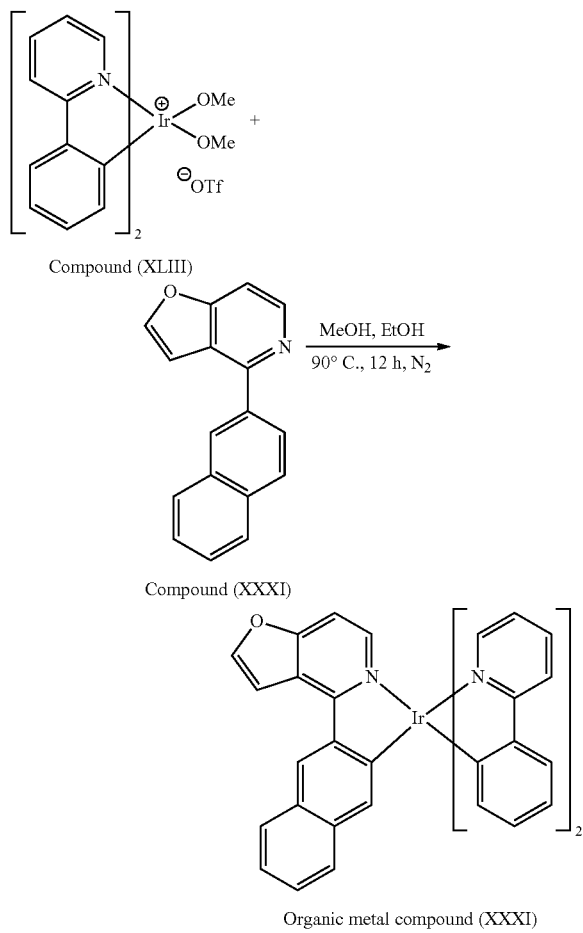

Compound (XLIII)

Compound (XXXI)

Organic metal compound (XXXI)

The physical measurement of Organic metal compound (XXXI) is listed below: $^1$H NMR (500 MHz, Acetone-d$_6$, 294 K): 8.75 (s, 1H), 8.18 (d, 1H), 8.11~8.07 (m, 3H), 7.90 (d, 1H), 7.79~7.67 (m, 7H), 7.40 (d, 1H), 7.20~7.14 (m, 4H), 7.07 (dd, 1H), 6.97 (dd, 1H), 6.88~6.73 (m, 5H), 6.61 (dd, 1H).

Example 32: Preparation of Organic Metal Compound (XXXII)

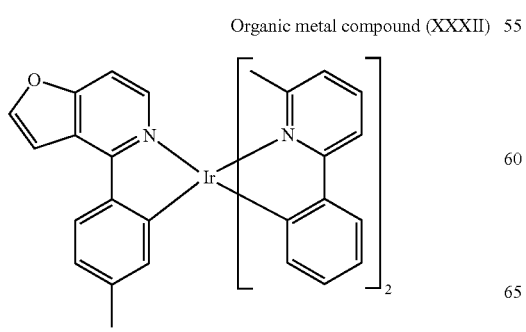

Organic metal compound (XXXII)

4.2 mmol of Compound (XLIV), 2 mmol of iridium trichloride (IrCl$_3$), 15 ml of 2-methoxyethanol, and 5 ml of water were added into the reaction bottle. Next, after removing moisture and purging nitrogen gas several times, the reaction bottle was heated to reflux. After reacting for 24 hr and cooling down to room temperature, the result was filtrated. The filter cake was collected, washed with water and methanol, and dried, obtaining Compound (XLV). The synthesis pathway of the above reaction was as follows:

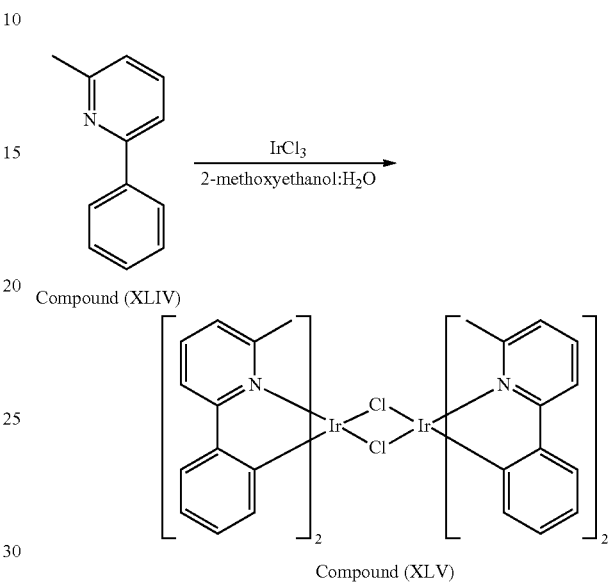

Compound (XLIV)

Compound (XLV)

1 mmol of Compound (XLV) and 10 mL of dichloromethane were added into a first reaction bottle. 2.2 mmol of silver trifluoromethanesulfonate (AgOTf) and 5 mL of methanol were added into a second reaction bottle, obtaining a methanol solution. Next, the methanol solution was added into the first reaction bottle, and the mixture was stirred for 18 hr. Next, after filtrating for removing sliver chloride and concentrating, Compound (XLVI) is obtained. The synthesis pathway of the above reaction was as follows:

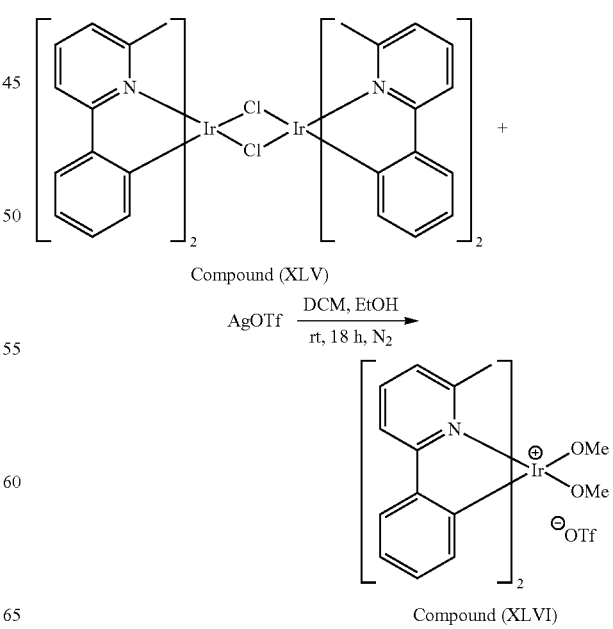

Compound (XLV)

Compound (XLVI)

Next, 1 mmol of Compound (XLVI), 2.5 mmol of Compound (V), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXXII). The synthesis pathway of the above reaction was as follows:

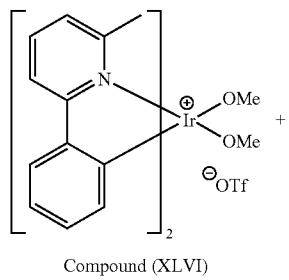

Compound (XLVI)

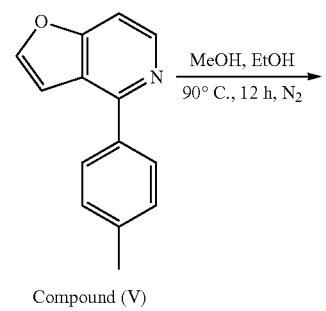

Compound (V)

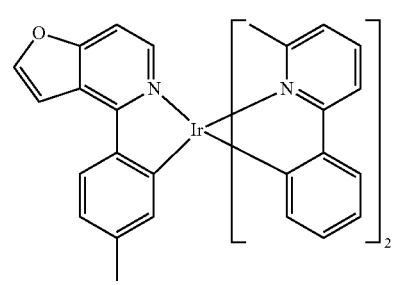

Organic metal compound (XXXII)

The physical measurement of Organic metal compound (XXXII) is listed below: $^1$H NMR (500 MHz, CDCl$_3$, 294 K): 7.87 (d, 1H), 7.83 (d, 1H), 7.80 (d, 1H), 7.71 (d, 1H), 7.66 (d, 1H), 7.62 (d, 1H), 7.58 (d, 1H), 7.53 (t, 1H), 7.46~7.42 (m, 2H), 6.95 (d, 1H), 6.91~6.86 (m, 2H), 6.81~6.63 (m, 5H), 6.55 (d, 1H), 6.48~6.45 (m, 2H), 2.07 (s, 3H), 2.00 (s, 3H), 1.87 (s, 3H).

Example 33: Preparation of Organic Metal Compound (XXXIII)

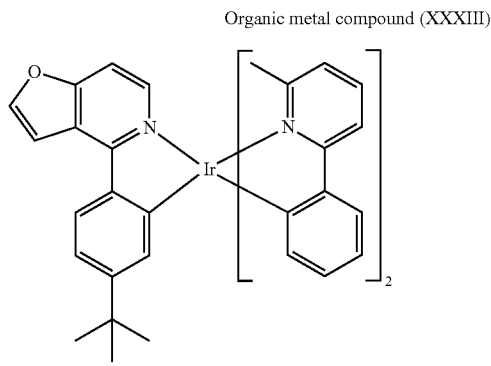

Organic metal compound (XXXIII)

Next, 1 mmol of Compound (XLVI), 2.5 mmol of Compound (XIII), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXXIII). The synthesis pathway of the above reaction was as follows:

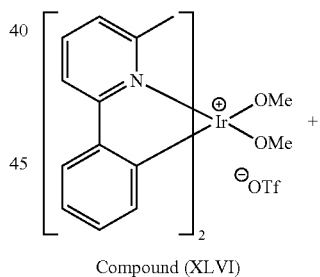

Compound (XLVI)

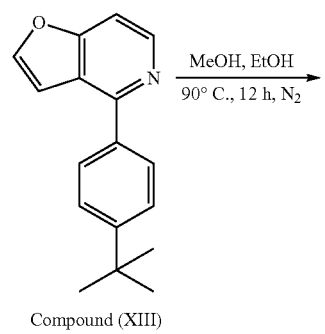

Compound (XIII)

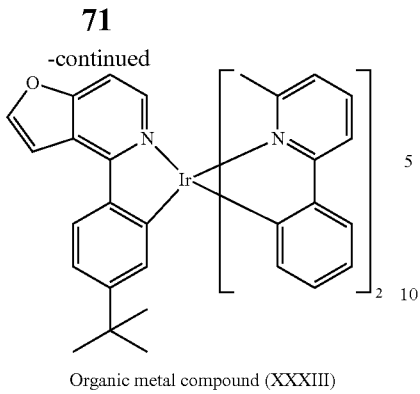

Organic metal compound (XXXIII)

The physical measurement of Organic metal compound (XXXIII) is listed below: $^1$H NMR (500 MHz, CDCl$_3$, 294 K): 7.86~7.81 (m, 3H), 7.73 (d, 1H), 7.65 (d, 1H), 7.60~7.54 (m, 3H), 7.44~7.38 (m, 2H), 6.95~6.88 (m, 4H), 6.80 (t, 1H), 6.73 (t, 1H), 6.68~6.59 (m, 4H), 6.47 (d, 1H), 2.04 (s, 3H), 1.86 (s, 3H), 1.02 (s, 9H).

Example 34: Preparation of Organic Metal Compound (XXXIV)

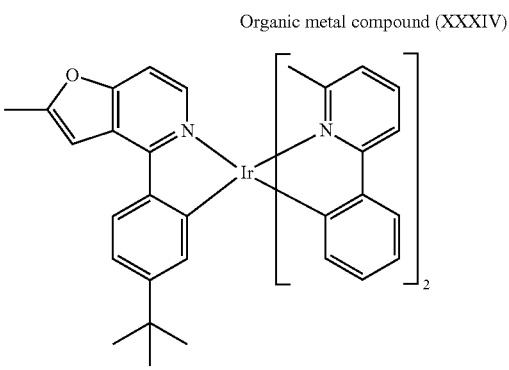

Organic metal compound (XXXIV)

Next, 1 mmol of Compound (XLVI), 2.5 mmol of Compound (XXXVIII), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXXIV) The synthesis pathway of the above reaction was as follows:

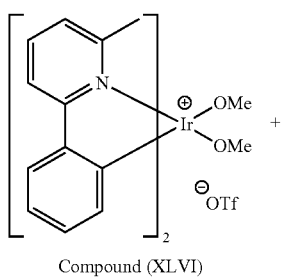

Compound (XLVI)

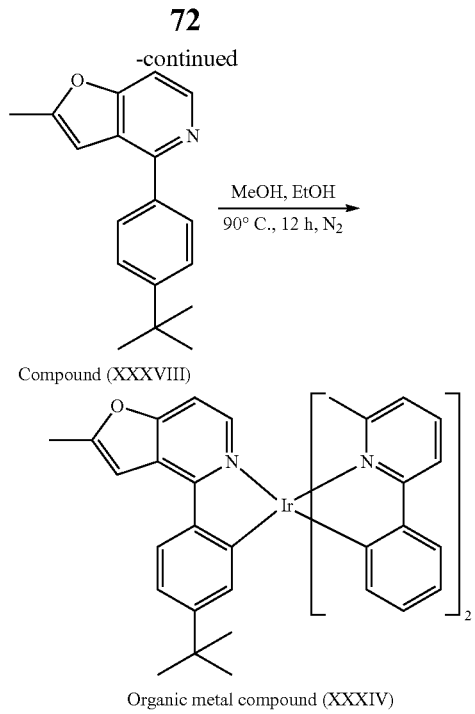

Compound (XXXVIII)

Organic metal compound (XXXIV)

The physical measurement of Organic metal compound (XXXIV) is listed below: $^1$H NMR (500 MHz, CDCl$_3$, 294 K): 8.00 (dd, 2H), 7.90 (d, 1H), 7.80 (d, 1H), 7.73~7.65 (m, 3H), 7.56 (t, 1H), 7.32 (s, 1H), 7.08~7.05 (m, 2H), 6.88 (dd, 1H), 6.84~6.81 (m, 2H), 6.73~6.69 (m, 2H), 6.60~6.59 (m, 2H), 6.50~6.45 (m, 2H), 2.53 (s, 3H), 2.05 (s, 3H), 1.93 (s, 3H), 0.99 (s, 9H).

Example 35: Preparation of Organic Metal Compound (XXXV)

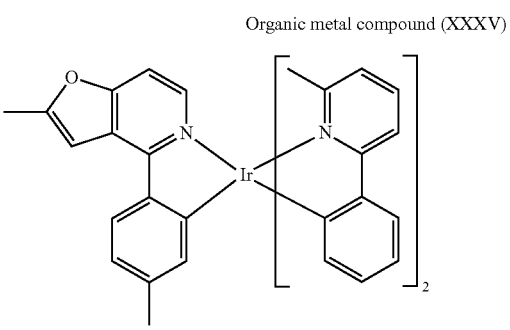

Organic metal compound (XXXV)

Next, 1 mmol of Compound (XLVI), 2.5 mmol of Compound (XXXVI), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXXV). The synthesis pathway of the above reaction was as follows:

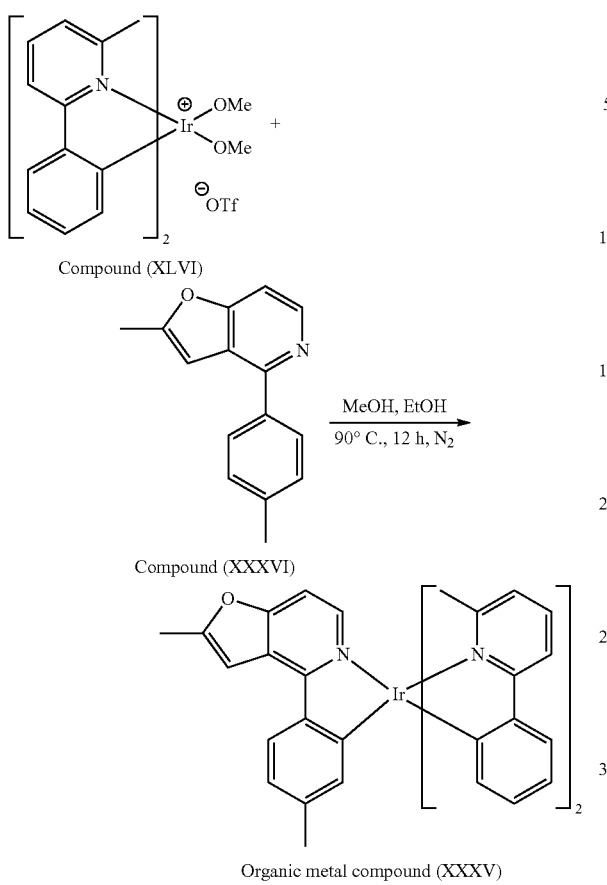

The physical measurement of Organic metal compound (XXXV) is listed below: $^1$H NMR (500 MHz, CDCl$_3$, 294 K): 7.85~7.79 (m, 3H), 7.76 (d, 1H), 7.60 (d, 1H), 7.52 (dd, 2H), 7.44 (dd, 1H), 7.07 (s, 1H), 6.83~6.63 (m, 8H), 6.43 (s, 1H), 6.36 (s, 2H), 2.50 (s, 3H), 2.05 (s, 3H), 1.96 (s, 3H), 1.86 (s, 3H).

Example 36: Preparation of Organic Metal Compound (XXXVI)

Organic metal compound (XXXVI)

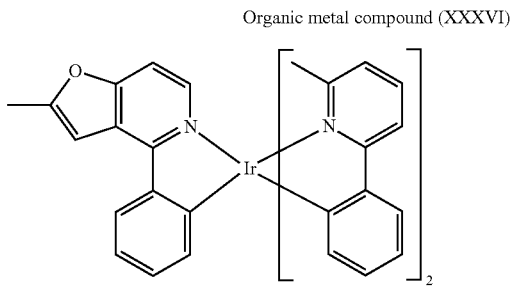

Next, 1 mmol of Compound (XLVI), 2.5 mmol of Compound (XLII), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXXVI). The synthesis pathway of the above reaction was as follows:

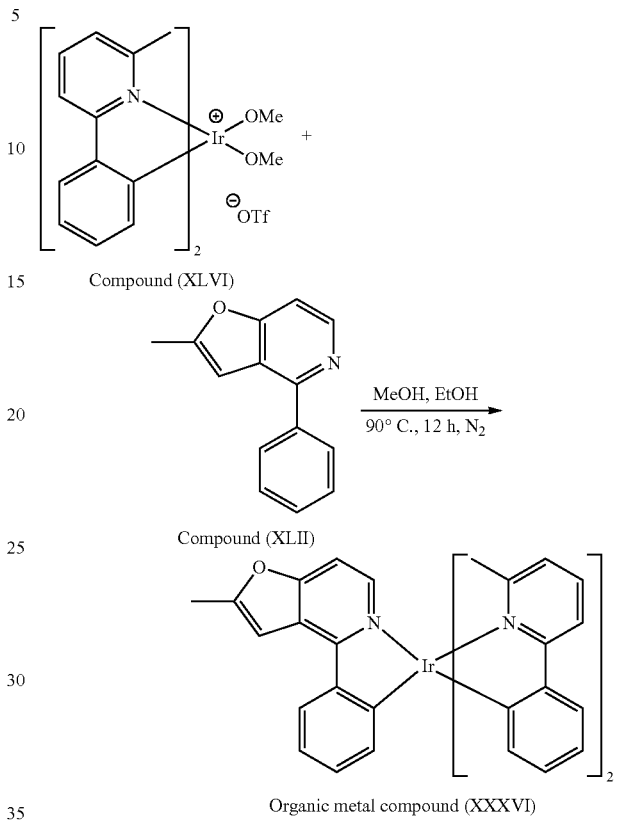

The physical measurement of Organic metal compound (XXXVI) is listed below: $^1$H NMR (500 MHz, CDCl$_3$, 294 K): 7.94 (d, 1H), 7.81 (dd, 2H), 7.74 (s, 1H), 7.59~7.52 (m, 3H), 7.44 (dd, 1H), 7.09 (s, 1H), 6.93~6.77 (m, 7H), 6.67 (d, 1H), 6.63 (dd, 1H), 6.60 (s, 1H), 6.49 (s, 1H), 6.35 (s, 1H), 2.51 (s, 3H), 1.99 (s, 3H), 1.86 (s, 3H).

Example 37: Preparation of Organic Metal Compound (XXXVII)

Organic metal compound (XXXVII)

Next, 1 mmol of Compound (XLVI), 2.5 mmol of Compound (XVII), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water.

Next, an organic phase was separated and concentrated, and then purified by column chromatography, obtaining Organic metal compound (XXXVII). The synthesis pathway of the above reaction was as follows:

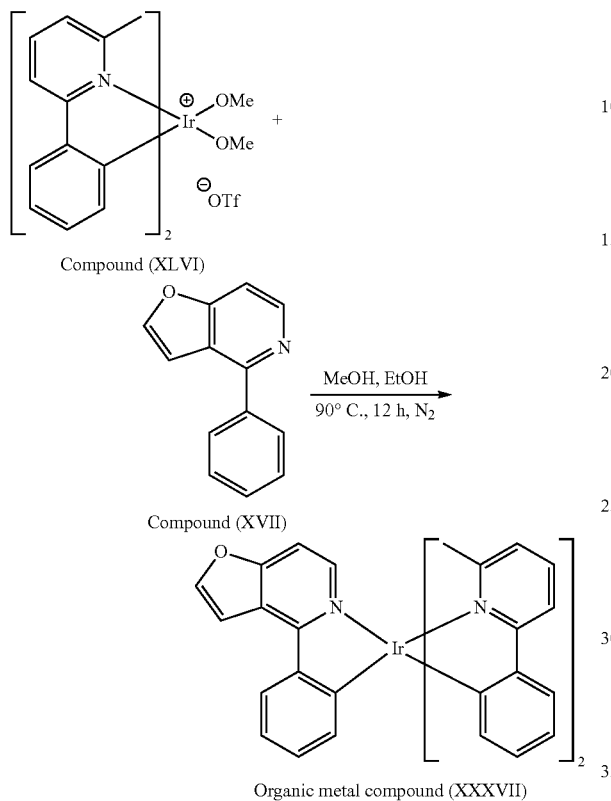

Compound (XLVI)

Compound (XVII)

Organic metal compound (XXXVII)

The physical measurement of Organic metal compound (XXXVII) is listed below: $^1$H NMR (500 MHz, CDCl$_3$, 294 K): 7.99 (d, 1H), 7.82 (dd, 2H), 7.74 (d, 1H), 7.69 (s, 1H), 7.65 (s, 1H), 7.59 (s, 1H), 7.54 (dd, 1H), 7.49 (s, 1H), 7.44 (dd, 1H), 6.99 (d, 1H), 6.94 (dd, 1H), 6.87~6.85 (m, 2H), 6.80~6.74 (m, 3H), 6.68 (d, 1H), 6.63 (dd, 2H), 6.49 (s, 1H), 6.37 (s, 1H), 2.00 (s, 3H), 1.86 (s, 3H).

Example 38: Preparation of Organic Metal Compound (XXXVIII)

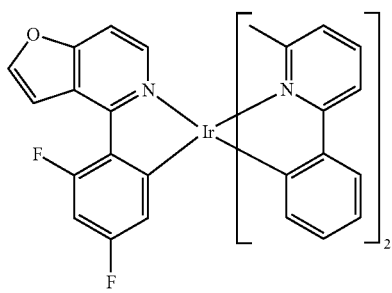

Organic metal compound (XXXVIII)

Next, 1 mmol of Compound (XLVI), 2.5 mmol of Compound (IX), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXXVIII). The synthesis pathway of the above reaction was as follows:

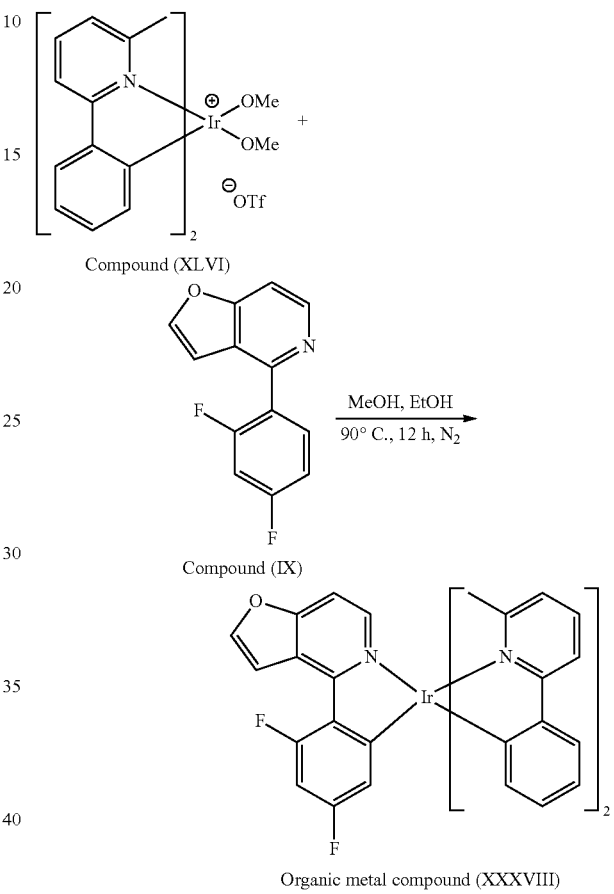

Compound (XLVI)

Compound (IX)

Organic metal compound (XXXVIII)

The physical measurement of Organic metal compound (XXXVIII) is listed below: $^1$H NMR (500 MHz, CDCl$_3$, 294 K): 7.85 (d, 1H), 7.80 (d, 1H), 7.73 (d, 1H), 7.71 (d, 1H), 7.60 (d, 1H), 7.56~7.47 (m, 3H), 7.40 (s, 1H), 7.02 (d, 1H), 6.90~6.87 (m, 2H), 6.82 (t, 1H), 6.75 (d, 1H), 6.72 (t, 1H), 6.66 (t, 1H), 6.47 (d, 2H), 6.38 (ddd, 1H), 6.15 (dd, 1H), 1.99 (s, 3H), 1.94 (s, 3H).

Example 39: Preparation of Organic Metal Compound (XXXIX)

Organic metal compound (XXXIX)

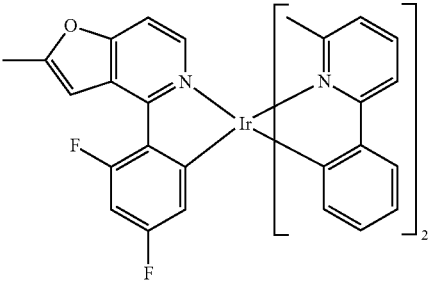

Next, 1 mmol of Compound (XLVI), 2.5 mmol of Compound (XXVI), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XXXIX). The synthesis pathway of the above reaction was as follows:

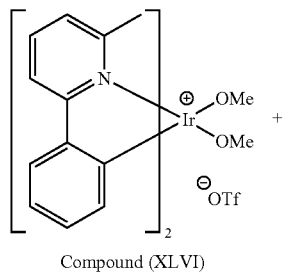

Compound (XLVI)

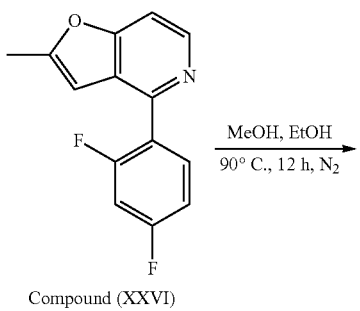

Compound (XXVI)

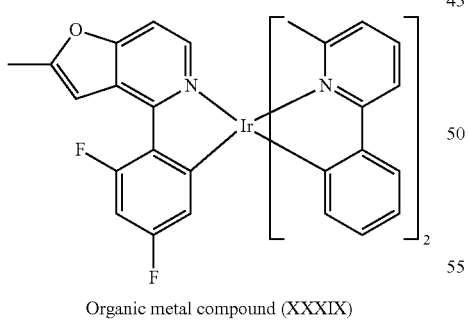

Organic metal compound (XXXIX)

The physical measurement of Organic metal compound (XXXIX) is listed below: $^1$H NMR (500 MHz, CDCl$_3$, 294 K): 7.85 (d, 1H), 7.79 (d, 1H), 7.70 (d, 1H), 7.66 (d, 1H), 7.56~7.47 (m, 3H), 6.99 (d, 1H), 6.92~6.86 (m, 3H), 6.813 (t, 1H), 6.76~6.70 (m, 2H), 6.66 (t, 1H), 6.48 (d, 2H), 6.36 (ddd, 1H), 6.13 (dd, 1H), 2.54 (s, 3H), 1.99 (s, 3H), 1.94 (s, 3H).

Example 40: Preparation of Organic Metal Compound (XL)

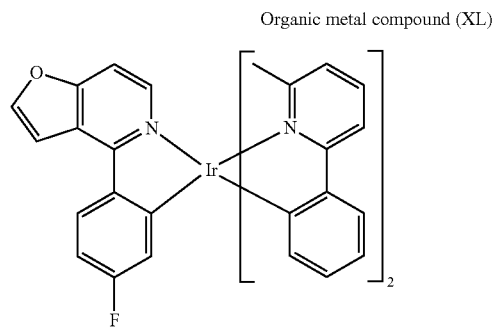

Organic metal compound (XL)

Next, 1 mmol of Compound (XLVI), 2.5 mmol of Compound (XXX), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XL). The synthesis pathway of the above reaction was as follows:

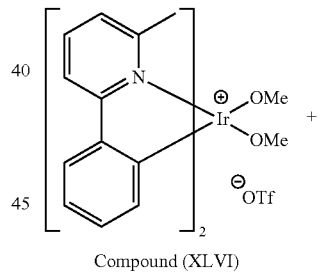

Compound (XLVI)

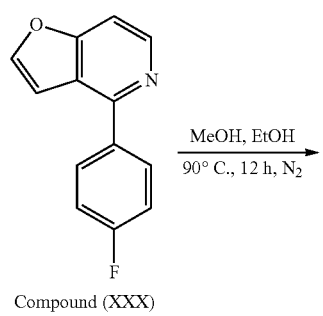

Compound (XXX)

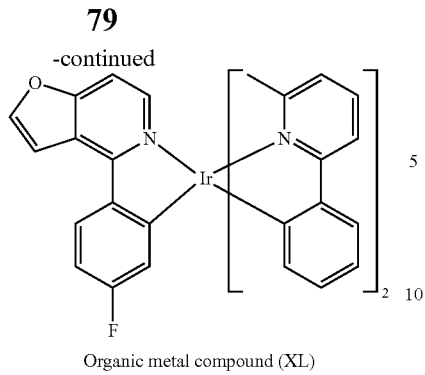

Organic metal compound (XL)

The physical measurement of Organic metal compound (XL) is listed below: $^1$H NMR (500 MHz, CDCl$_3$, 294 K): 7.95 (dd, 1H), 7.86 (d, 1H), 7.81 (d, 1H), 7.72 (d, 1H), 7.69 (s, 1H), 7.62 (d, 1H), 7.58~7.53 (m, 2H), 7.47 (dd, 1H), 7.42 (s, 1H), 7.00 (d, 1H), 6.92~6.88 (m, 2H), 6.81 (dd, 1H), 6.75~6.71 (m, 2H), 6.67~6.62 (m, 2H), 6.53 (d, 1H), 6.43 (d, 1H), 6.31 (dd, 1H), 2.00 (s, 3H), 1.85 (s, 3H).

Example 41: Preparation of Organic Metal Compound (XLI)

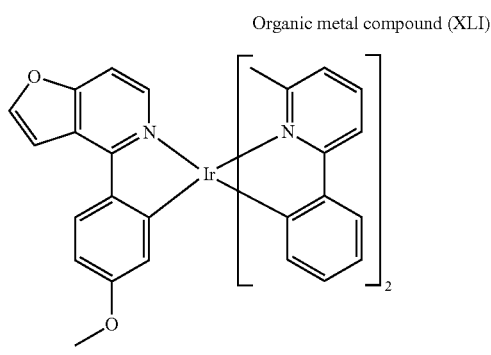

Organic metal compound (XLI)

Next, 1 mmol of Compound (XLVI), 2.5 mmol of Compound (XXXII), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XLI). The synthesis pathway of the above reaction was as follows:

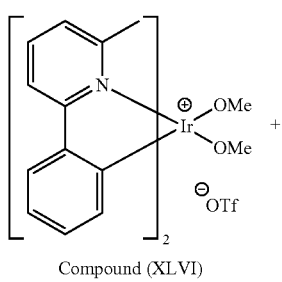

Compound (XLVI)

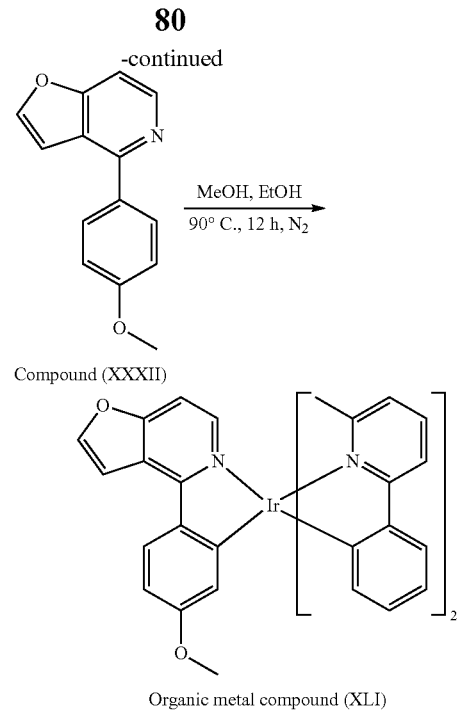

Compound (XXXII)

MeOH, EtOH
90° C., 12 h, N$_2$

Organic metal compound (XLI)

The physical measurement of Organic metal compound (XLI) is listed below: $^1$H NMR (500 MHz, CDCl$_3$, 294 K): 7.90 (d, 1H), 7.83 (d, 1H), 7.81 (d, 1H), 7.70 (d, 1H), 7.65 (s, 1H), 7.59~7.52 (m, 3H), 7.46~7.41 (m, 2H), 6.92 (d, 1H), 6.89~6.86 (m, 2H), 6.81 (dd, 1H), 6.73~6.70 (m, 2H), 6.65 (dd, 1H), 6.57 (d, 1H), 6.52~6.47 (m, 2H), 6.19 (d, 1H), 3.47 (s, 3H), 2.00 (s, 3H), 1.88 (s, 3H).

Example 42: Preparation of Organic Metal Compound (XLII)

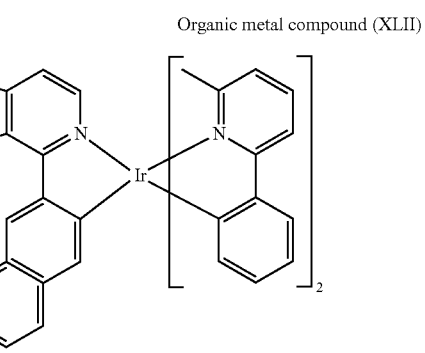

Organic metal compound (XLII)

Next, 1 mmol of Compound (XLVI), 2.5 mmol of Compound (XXI), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XLII). The synthesis pathway of the above reaction was as follows:

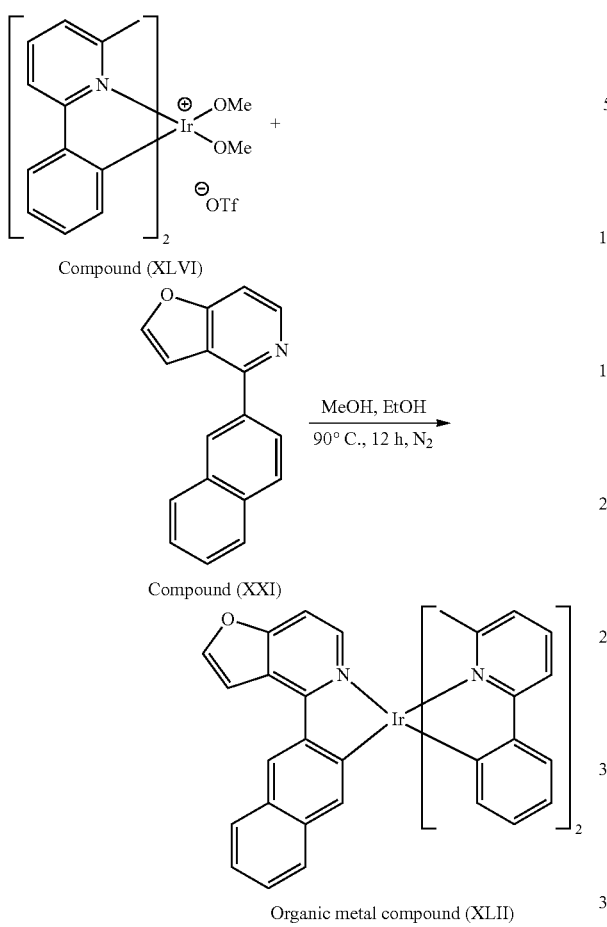

The physical measurement of Organic metal compound (XLII) is listed below: $^1$H NMR (500 MHz, CDCl$_3$, 294 K): 8.48 (s, 1H), 7.84 (d, 1H), 7.82 (d, 1H), 7.77~7.73 (m, 4H), 7.70 (s, 1H), 7.58 (d, 1H), 7.55 (dd, 1H), 7.39 (dd, 1H), 7.32 (d, 1H), 7.21~7.18 (m, 2H), 7.05 (d, 1H), 6.97 (s, 1H), 6.94 (dd, 1H), 6.89 (d, 1H), 6.80~6.75 (m, 2H), 6.64 (d, 1H), 6.60 (d, 1H), 6.55 (dd, 1H), 6.47 (d, 1H), 2.03 (s, 3H), 1.88 (s, 3H).

Example 43: Preparation of Organic Metal Compound (XLIII)

Organic metal compound (XLIII)

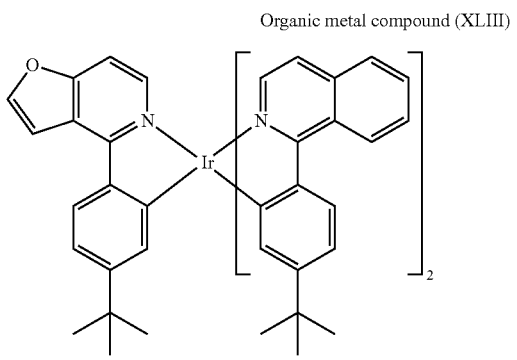

Next, 1 mmol of Compound (XLVII), 2.5 mmol of Compound (XIII), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XLIII). The synthesis pathway of the above reaction was as follows:

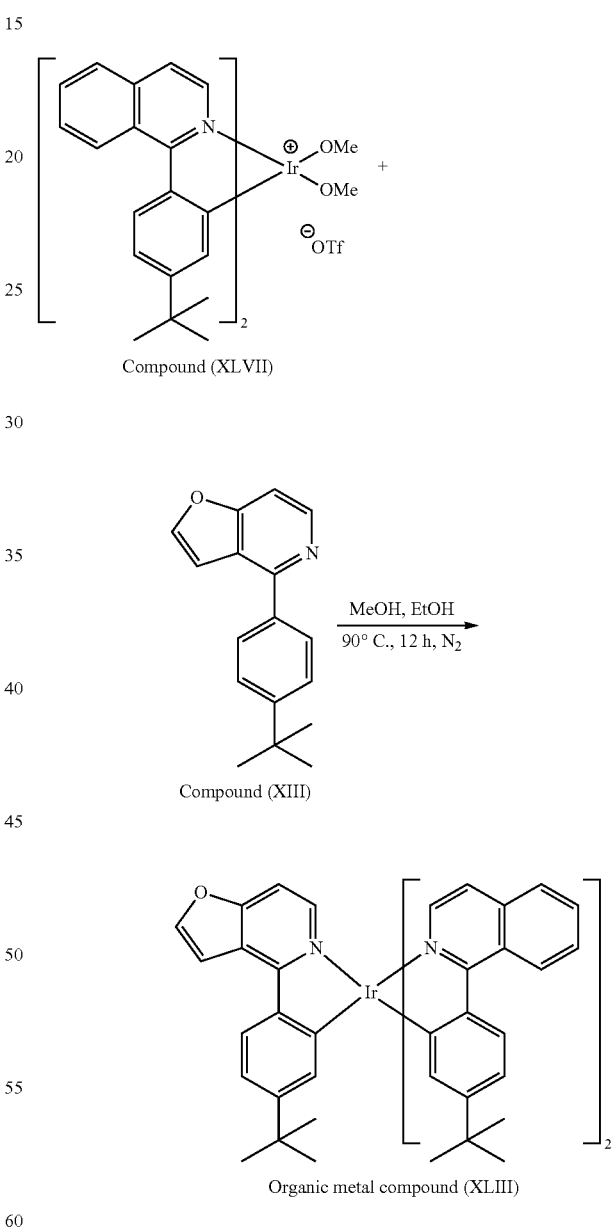

The physical measurement of Organic metal compound (XLIII) is listed below: $^1$H-NMR (500 MHz, CDCl$_3$, 294 K): 8.99~8.93 (m, 2H), 8.11 (t, 2H), 7.95 (d, 1H), 7.74~7.69 (m, 3H), 7.63~7.59 (m, 4H), 7.51 (s, 1H), 7.35 (d, 1H), 7.24 (d, 1H), 7.20 (d, 1H), 7.12~7.07 (m, 3H), 7.03~6.95 (m, 5H), 6.82 (s, 1H), 1.14 (s, 9H), 1.12 (s, 9H), 1.09 (s, 9H).

Example 44: Preparation of Organic Metal Compound (XLIV)

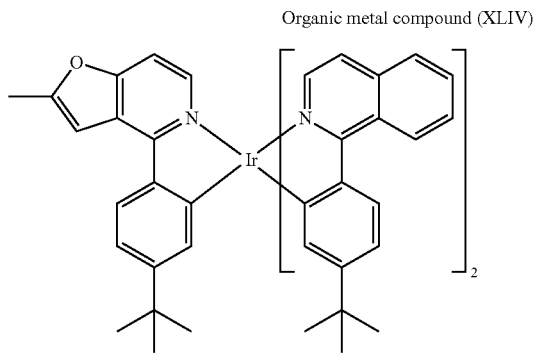
Organic metal compound (XLIV)

Next, 1 mmol of Compound (XLVII), 2.5 mmol of Compound (XXXVIII), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XLIV). The synthesis pathway of the above reaction was as follows:

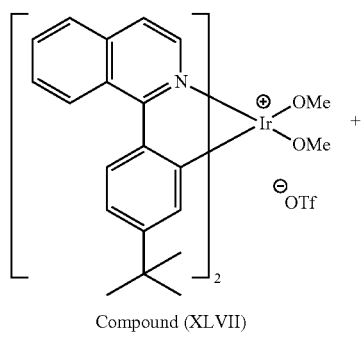
Compound (XLVII)

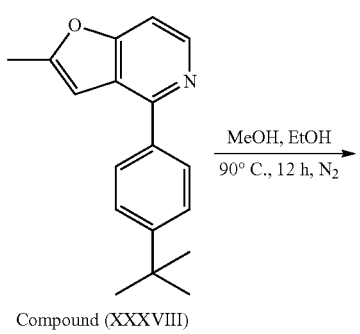
Compound (XXXVIII)

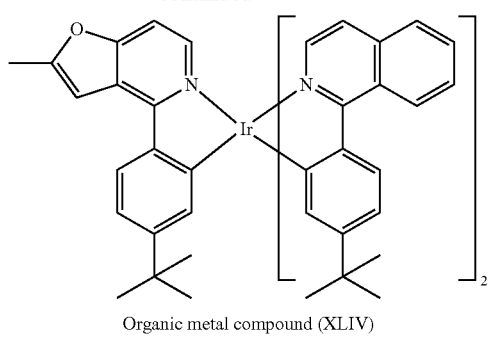
Organic metal compound (XLIV)

The physical measurement of Organic metal compound (XLIV) is listed below: $^1$H NMR (500 MHz, CDCl$_3$, 294 K): 8.98~8.93 (m, 2H), 8.12~8.08 (t, 2H), 7.88 (d, 1H), 7.73~6.69 (m, 2H), 7.63~7.57 (m, 4H), 7.34 (d, 1H), 7.24 (d, 1H), 7.13~6.92 (m, 9H), 6.84 (d, 1H), 6.80 (s, 1H), 2.52 (s, 3H), 1.14 (s, 9H), 1.12 (s, 9H), 1.08 (s, 9H).

Example 45: Preparation of Organic Metal Compound (XLV)

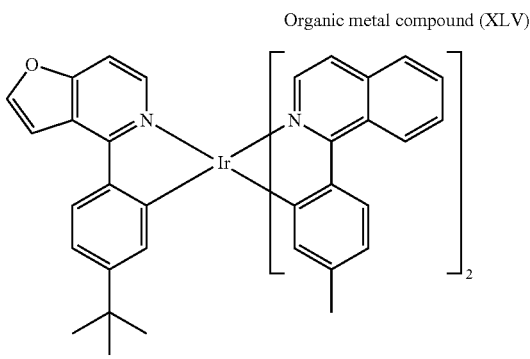
Organic metal compound (XLV)

Next, 1 mmol of Compound (XLVIII), 2.5 mmol of Compound (XIII), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XLV). The synthesis pathway of the above reaction was as follows:

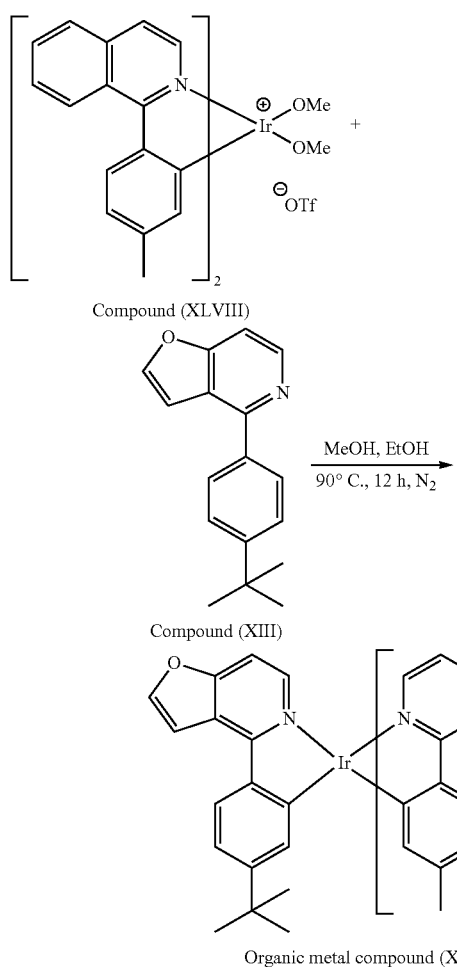

Compound (XLVIII)

Compound (XIII)

MeOH, EtOH
90° C., 12 h, N₂

Organic metal compound (XLV)

The physical measurement of Organic metal compound (XLV) is listed below: ¹H NMR (500 MHz, CDCl₃, 294 K): 8.91 (m, 2H), 8.04 (m, 2H), 7.92 (d, 2H), 7.69 (d, 2H), 7.60 (m, 2H), 7.49 (m, 2H), 7.38~7.30 (m, 2H), 7.23~7.16 (m, 3H), 7.08~6.78 (m, 8H), 2.20 (s, 3H), 2.16 (s, 3H), 1.11 (s, 9H).

Example 46: Preparation of Organic Metal Compound (XLVI)

Organic metal compound (XLVI)

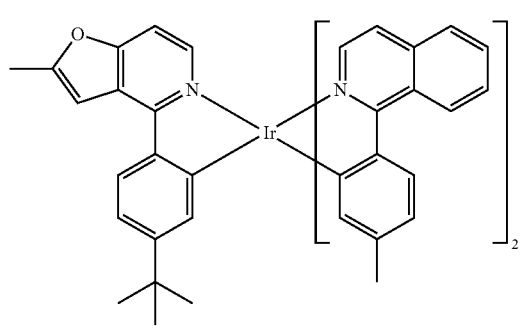

Next, 1 mmol of Compound (XLVIII), 2.5 mmol of Compound (XXXVIII), 5 ml of methanol, and 5 ml of ethanol were added into a reaction bottle. Next, after removing moisture and purging nitrogen gas several times, the reaction bottle was heated to 90° C. After reacting for 12 hr and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Organic metal compound (XLVI). The synthesis pathway of the above reaction was as follows:

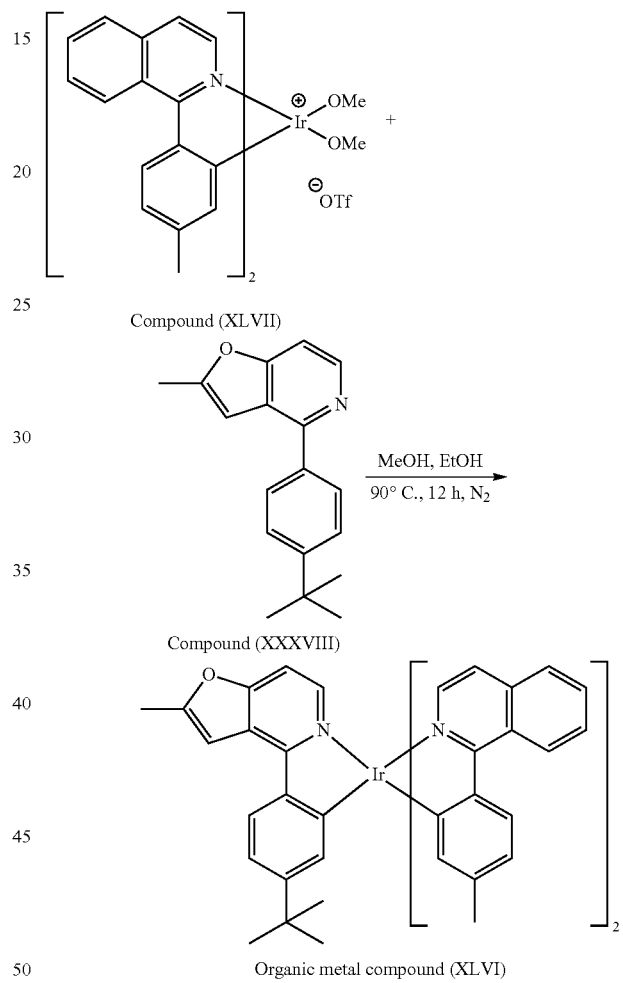

Compound (XLVII)

Compound (XXXVIII)

MeOH, EtOH
90° C., 12 h, N₂

Organic metal compound (XLVI)

The physical measurement of Organic metal compound (XLVI) is listed below: ¹H NMR (500 MHz, CDCl₃, 294 K): 8.92 (m, 1H), 8.05 (m, 1H), 7.86 (m, 2H), 7.73 (m, 1H), 7.60 (m, 2H), 7.37~7.20 (m, 3H), 7.16~7.12 (m, 4H), 6.98~6.78 (m, 10H), 2.52 (s, 3H), 2.20 (s, 3H), 2.16 (s, 3H), 1.10 (s, 9H).

Due to the furopyridine derivative functional group, the organic metal compound having the structure of Formula (I) or Formula (II) of the disclosure can serve as a dapant of the light emitting layer, resulting in the organic light-emitting device employing the organic metal compound of the disclosure having increased electron conductivity, high luminous efficiency, and improved life-time.

In addition, since the reactants and reagents for synthesizing the compound having furopyridine derivative functional group are dangerous and the steps are complicated time-consuming, it is generally considered that the compound having furopyridine derivative functional group is difficult to be synthesized. As a result, few reports on the research and development of the compound having furopyridine derivative functional group. The disclosure provides an iridium complex having furopyridine functional group and a process for preparing the iridium complex having furopyridine derivative functional group with a relatively high yield.

The conventional blue phosphorescent material FIr(pic) (having a structure represented by (having a structure represented by

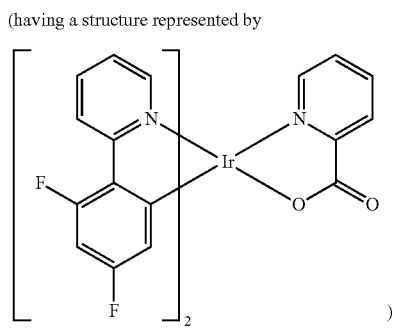

)

has a sublimation yield of about 50%. On the other hand, due to the furopyridine derivative functional group bonded to Ir, the organic metal compound having a structure of Formula (I) or Formula (II) of the disclosure is suitable for being purified by a sublimation process (i.e. the organic metal compound having a structure of Formula (I) or Formula (II) of the disclosure has a sublimation yield that is greater than 80%).

The photoluminescence (PL) spectra of the organic metal compound having a structure of Formula (I) or Formula (II) of the disclosure as disclosed in Examples were measured, and the results were shown in Table 1.

TABLE 1

| organic metal compound | maximum PL wavelength (nm) |
|---|---|
| organic metal compound (I) | 532 |
| organic metal compound (II) | 504 |
| organic metal compound (VI) | 562 |
| organic metal compound (VII) | 501 |
| organic metal compound (XI) | 534 |
| organic metal compound (XII) | 497 |
| organic metal compound (XIII) | 562 |
| organic metal compound (XIV) | 520 |
| organic metal compound (XVI) | 561 |
| organic metal compound (XX) | 534 |
| organic metal compound (XXI) | 529 |
| organic metal compound (XXII) | 530 |
| organic metal compound (XXIII) | 520 |
| organic metal compound (XXIV) | 518 |
| organic metal compound (XXV) | 523 |
| organic metal compound (XXVI) | 532 |
| organic metal compound (XXVII) | 516 |
| organic metal compound (XXVIII) | 506 |
| organic metal compound (XXIX) | 516 |
| organic metal compound (XXX) | 516 |
| organic metal compound (XXXI) | 566 |
| organic metal compound (XXXII) | 529 |
| organic metal compound (XXXIII) | 529 |
| organic metal compound (XXXIV) | 522 |
| organic metal compound (XXXV) | 519 |
| organic metal compound (XXXVI) | 524 |

TABLE 1-continued

| organic metal compound | maximum PL wavelength (nm) |
|---|---|
| organic metal compound (XXXVII) | 534 |
| organic metal compound (XXXVIII) | 518 |
| organic metal compound (XXXIX) | 508 |
| organic metal compound (XL) | 518 |
| organic metal compound (XLI) | 518 |
| organic metal compound (XLII) | 563 |
| organic metal compound (XLIII) | 620 |

FIG. 1 shows an embodiment of an organic light-emitting device 10. The organic light-emitting device 10 includes a substrate 12, a bottom electrode 14, an organic light-emitting element 16, and a top electrode 18, as shown in FIG. 1. The organic light-emitting device can be a top-emission, bottom-emission, or dual-emission devices. The substrate 12 can be a glass, plastic, or semiconductor substrate. Suitable materials for the bottom and top electrodes can be Ca, Ag, Mg, Al, Li, In, Au, Ni, W, Pt, Cu, indium tin oxide (ITO), indium zinc oxide (IZO), aluminum zinc oxide (AZO), or zinc oxide (ZnO), formed by sputtering, electron beam evaporation, thermal evaporation, or chemical vapor deposition. Furthermore, at least one of the bottom and top electrodes 14 and 18 is transparent.

The organic light-emitting element 16 at least includes an emission layer, and can further include a hole injection layer, a hole transport layer, an electron transport layer, and an electron injection layer. In an embodiment of the disclosure, at least one layer of the organic light-emitting element 16 includes the organic metal compound having a structure of Formula (I) of the disclosure.

According to another embodiment of the disclosure, the organic light-emitting device can be a phosphorescent organic light-emitting device, and the emission layer of the organic light-emitting element can include a host material and a dopant, wherein the dopant can include the organic metal compound having a structure of Formula (I) of the disclosure. The dose of the dopant is not limited and can be optionally modified by a person of ordinary skill in the field In order to clearly disclose the organic light-emitting devices of the disclosure, the following examples (having an emitting layer employing the organic metal compounds of the disclosure formed by deposition (dry process) or coating (wet process)) are intended to illustrate the disclosure more fully without limiting their scope, since numerous modifications and variations will be apparent to those skilled in this art.

Example 47: Organic Light-Emitting Device (I)

A glass substrate with an indium tin oxide (ITO) film with a thickness of 120 nm was provided and then washed with a cleaning agent, acetone, and isopropanol with ultrasonic agitation. After drying with nitrogen flow, the ITO film was subjected to a UV/ozone treatment for 30 min.

Next, PEDOT:PSS (Poly(3,4-ethylenedioxythiophene)-poly(styrenesulfonate)) was coated on the ITO film by a spin coating process (with a rotation rate of 800 rpm for 3 sec and a rotation rate of 2000 rpm for 40 sec) and baked at 130° C. for 40 min to form a PEDOT:PSS film serving as a hole injection layer (with a thickness of 40 nm). Next, TAPC (1,1-bis[4-[N,N'-di(p-tolyl)amino]phenyl]cyclohexane, with a thickness of 35 nm), TCTA (4,4',4'-tri(N-carbazolyl) triphenylamine) doped with Organic metal compound (I) (the weight ratio between TCTA and Organic metal compound (I) was 94:6, with a thickness of 15 nm), TmPyPB (1,3,5-tri(m-pyrid-3-yl-phenyl)benzene, with a thickness of 42 nm), LiF (with a thickness of 0.5 nm), and Al (with a thickness of 120 nm), were subsequently formed on the PEDOT:PSS film at $10^{-6}$ torr, obtaining the organic light-emitting device (I) after encapsulation. The materials and layers formed therefrom are described in the following: ITO/PEDOT:PSS/TAPC/TCTA:organic metal compound (I) (6%)/TmPyPB/LiF/Al Next, the optical properties (such as maximum emission peak, driving voltage, current efficiency, power efficiency, and C.I.E coordinate) of the light-emitting device (I) were measured by a spectra colorimeter PR650 (purchased from Photo Research Inc.) and a luminance meter LS110 (purchased from Konica Minolta). The results are shown in Table 2.

Example 48: Organic Light-Emitting Device (II)

Example 48 was performed in the same manner as in Example 47 except that Organic metal compound (II) was substituted for Organic metal compound (I), obtaining the organic light-emitting device (II). The materials and layers formed therefrom are described in the following: ITO/PEDOT:PSS/TAPC/TCTA:Organic metal compound (II) (6%)/TmPyPB/LiF/Al Next, the optical properties (such as maximum emission peak, driving voltage, current efficiency, power efficiency, and C.I.E coordinate) of the light-emitting device (II) were measured by a spectra colorimeter PR650 (purchased from Photo Research Inc.) and a luminance meter LS110 (purchased from Konica Minolta). The results are shown in Table 2.

Comparative Example 1: Organic Light-Emitting Device (III)

Comparative Example 1 was performed in the same manner as in Example 47 except that compound (R1) (having a structure of

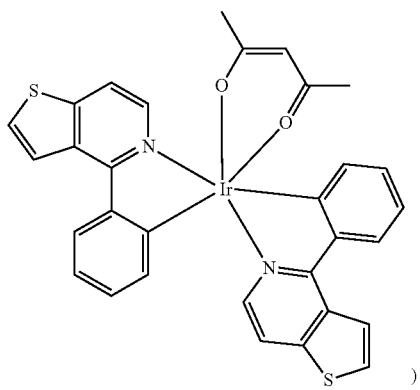

)

was substituted for Organic metal compound (I), obtaining the organic light-emitting device (III). The materials and layers formed therefrom are described in the following: ITO/PEDOT:PSS/TAPC/TCTA:compound (R1) (6%)/TmPyPB/LiF/Al Next, the optical properties (such as maximum emission peak, driving voltage, current efficiency, power efficiency, and C.I.E coordinate) of the light-emitting device (III) were measured by a spectra colorimeter PR650 (purchased from Photo Research Inc.) and a luminance meter LS110 (purchased from Konica Minolta). The results are shown in Table 2.

Comparative Example 2: Organic Light-Emitting Device (IV)

Comparative Example 2 was performed in the same manner as in Example 47 except that compound (R2) (having a structure of

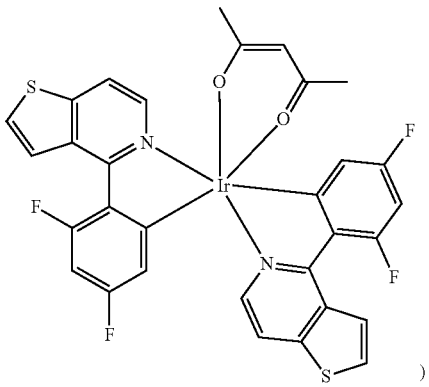

)

was substituted for Organic metal compound (I), obtaining the organic light-emitting device (IV). The materials and layers formed therefrom are described in the following: ITO/PEDOT:PSS/TAPC/TCTA:compound (R2) (6%)/TmPyPB/LiF/Al Next, the optical properties (such as maximum emission peak, driving voltage, current efficiency, power efficiency, and C.I.E coordinate) of the light-emitting device (IV) were measured by a spectra colorimeter PR650 (purchased from Photo Research Inc.) and a luminance meter LS110 (purchased from Konica Minolta). The results are shown in Table 2.

Comparative Example 3: Organic Light-Emitting Device (V)

Comparative Example 3 was performed in the same manner as in Example 47 except that Ir(ppy)$_3$ (having a structure of

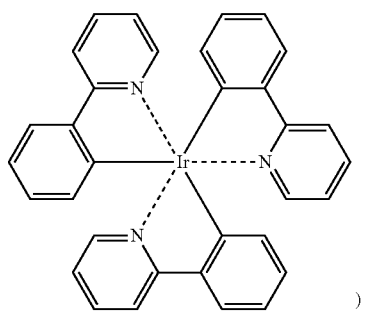

)

was substituted for Organic metal compound (I), obtaining the organic light-emitting device (V). The materials and layers formed therefrom are described in the following: ITO/PEDOT:PSS/TAPC/TCTA: Ir(ppy)$_3$ (6%)/TmPyPB/LiF/Al Next, the optical properties (such as maximum emission peak, driving voltage, current efficiency, power efficiency, and C.I.E coordinate) of the light-emitting device (V) were measured by a spectra colorimeter PR650 (purchased from Photo Research Inc.) and a luminance meter LS110 (purchased from Konica Minolta). The results are shown in Table 2.

TABLE 2

| | measured at a brightness of 1000 Cd/m² | | | measured at a brightness of 1000 Cd/m² | |
|---|---|---|---|---|---|
| | current efficiency (cd/A) | power efficiency (lm/W) | driving voltage (V) | C.I.E coordinate | maximum luminous intensity peak (nm) |
| organic light-emitting device (I) | 91.6 | 86.9 | 3.4 | (0.40, 0.58) | 540 |
| organic light-emitting device (II) | 86.0 | 77.2 | 3.5 | (0.29, 0.62) | 504 |
| organic light-emitting device (III) | 74 | 58.2 | 4.0 | (0.47, 0.49) | 564 |
| organic light-emitting device (IV) | 48.9 | 34.2 | 4.5 | (0.39, 0.58) | 528 |
| organic light-emitting device (V) | 56.3 | 36.8 | 4.8 | (0.31, 0.62) | 516 |

As shown in Table 1, in comparison with the driving voltage of the organic light-emitting device (III) of Comparative Example 1, the organic light-emitting device (I) (employing the organic metal compound (I) as phosphorescent dopant) has a 0.6V decrease of driving voltage. Furthermore, the current efficiency of the organic light-emitting device (I) is about 1.2 times higher than that of the organic light-emitting device (III), and the power efficiency of the organic light-emitting device (I) is about 1.5 times higher than that of the organic light-emitting device (III).

Example 49: Organic Light-Emitting Device (VI)

A glass substrate with an indium tin oxide (ITO) film with a thickness of 120 nm was provided and then washed with a cleaning agent, acetone, and isopropanol with ultrasonic agitation. After drying with nitrogen flow, the ITO film was subjected to a UV/ozone treatment for 30 min.

Next, PEDOT:PSS (Poly(3,4-ethylenedioxythiophene)-poly(styrenesulfonate)) was coated on the ITO film by a spin coating process (with a rotation rate of 800 rpm for 3 sec and a rotation rate of 2000 rpm for 40 sec) and baked at 130° C. for 40 min to form a PEDOT:PSS film serving as a hole injection layer (with a thickness of 40 nm). Next, a composition was used for forming a light-emitting layer coated on the PEDOT:PSS film by a blade coating process and baked at 100° C. for 40 min to form the light-emitting layer (with a thickness of 15 nm). The composition used for forming a light-emitting layer includes TCTA (4,4',4'-tri(N-carbazolyl)triphenylamine) and Organic metal compound (I), wherein the weight ratio of TCTA and Organic metal compound (I) was 94:6, dissolved in chlorobenzene. Next, TmPyPB (1,3,5-tri(m-pyrid-3-yl-phenyl)benzene was coated on the light-emitting layer by a spin coating process to form a TmPyPB film (with a thickness of 50 nm). Next, LiF (with a thickness of 1 nm), and Al (with a thickness of 100 nm) were subsequently formed on the TmPyPB film at 10⁻⁶ torr, obtaining the organic light-emitting device (VI) after encapsulation. The materials and layers formed therefrom are described in the following: ITO/PEDOT:PSS/TCTA:Organic metal compound (I) (6%)/TmPyPB/LiF/Al.

Next, the optical properties (such as maximum emission peak, driving voltage, current efficiency, power efficiency, and C.I.E coordinate) of the light-emitting device (VI) were measured by a spectra colorimeter PR650 (purchased from Photo Research Inc.) and a luminance meter LS110 (purchased from Konica Minolta). The results are shown in Table 3.

Example 50: Organic Light-Emitting Device (VII)

Example 50 was performed in the same manner as in Example 49 except that Organic metal compound (II) was substituted for Organic metal compound (I), obtaining the organic light-emitting device (VII). The materials and layers formed therefrom are described in the following: ITO/PEDOT:PSS/TCTA:Organic metal compound (II) (6%)/TmPyPB/LiF/Al.

Next, the optical properties (such as maximum emission peak, driving voltage, current efficiency, power efficiency, and C.I.E coordinate) of the light-emitting device (VII) were measured by a spectra colorimeter PR650 (purchased from Photo Research Inc.) and a luminance meter LS110 (purchased from Konica Minolta). The results are shown in Table 3.

Comparative Example 4: Organic Light-Emitting Device (VIII)

Comparative Example 4 was performed in the same manner as in Example 49 except that compound (R1) (having a structure of (having a structure of

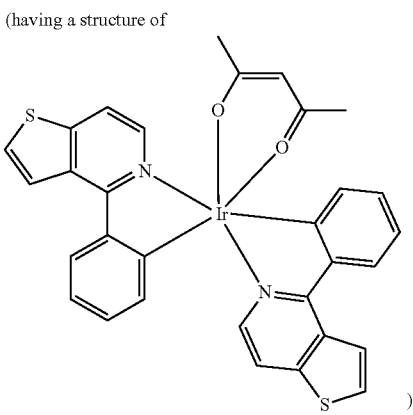

)

was substituted for Organic metal compound (I), obtaining the organic light-emitting device (VIII). The materials and layers formed therefrom are described in the following: ITO/PEDOT:PSS/TCTA: compound (R1) (6%)/TmPyPB/LiF/Al.

Next, the optical properties (such as maximum emission peak, driving voltage, current efficiency, power efficiency, and C.I.E coordinate) of the light-emitting device (VIII) were measured by a spectra colorimeter PR650 (purchased from Photo Research Inc.) and a luminance meter LS110 (purchased from Konica Minolta). The results are shown in Table 3.

Comparative Example 5: Organic Light-Emitting Device (IX)

Comparative Example 5 was performed in the same manner as in Example 49 except that compound (R2) (having a structure of (having a structure of

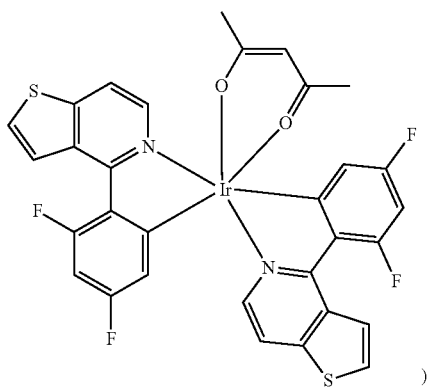

)

was substituted for Organic metal compound (I), obtaining the organic light-emitting device (IX). The materials and layers formed therefrom are described in the following: ITO/PEDOT:PSS/TCTA: compound (R2) (6%)/TmPyPB/LiF/Al.

Next, the optical properties (such as maximum emission peak, driving voltage, current efficiency, power efficiency, and C.I.E coordinate) of the light-emitting device (IX) were measured by a spectra colorimeter PR650 (purchased from Photo Research Inc.) and a luminance meter LS110 (purchased from Konica Minolta). The results are shown in Table 3.

As shown in Table 3, in comparison with the driving voltage of the organic light-emitting device (VIII) of Comparative Example 4, the organic light-emitting device (VI) (employing the organic metal compound (VI) as phosphorescent dopant) has a 0.2V decrease of driving voltage. Furthermore, the current efficiency and power efficiency of the organic light-emitting device (I) is about 1.2 times higher than that of the organic light-emitting device (VIII). In addition, in comparison with the driving voltage of the organic light-emitting device (IX) of Comparative Example 5, the organic light-emitting device (VII) (employing the organic metal compound (II) as phosphorescent dopant) has a 0.9V decrease of driving voltage. Furthermore, the current efficiency of the organic light-emitting device (VII) is about 1.1 times higher than that of the organic light-emitting device (IX), and the power efficiency of the organic light-emitting device (VII) is about 1.4 times higher than that of the organic light-emitting device (IX).

Example 51: Organic Light-Emitting Device (X)

A glass substrate with an indium tin oxide (ITO) film with a thickness of 120 nm was provided and then washed with a cleaning agent, acetone, and isopropanol with ultrasonic agitation. After drying with nitrogen flow, the ITO film was subjected to a UV/ozone treatment for 30 min.

Next, PEDOT:PSS (Poly(3,4-ethylenedioxythiophene)-poly(styrenesulfonate)) was coated on the ITO film by a spin coating process (with a rotation rate of 800 rpm for 3 sec and a rotation rate of 2000 rpm for 40 sec) and baked at 130° C. for 40 min to form a PEDOT:PSS film serving as a hole injection layer (with a thickness of 40 nm). Next, TAPC (1,1-bis[4-[N,N'-di(p-tolyl)amino]phenyl]cyclobexane, with a thickness of 40 nm), NPB (N,N'-bis(naphthalen-1-yl)-N,N'-bis(phenyl)-benzidine) doped with Organic metal compound (VI) (the weight ratio between TCTA and Organic metal compound (VI) was 97:3~96:4, with a thickness of 15 nm), TmPyPB (1,3,5-tri(m-pyrid-3-yl-phenyl) benzene, with a thickness of 50 nm), LiF (with a thickness of 0.8 nm), and Al (with a thickness of 120 nm), were subsequently formed on the PEDOT:PSS film at $10^{-6}$ torr, obtaining the organic light-emitting device (X) after encapsulation. The materials and layers formed therefrom are described in the following: ITO/PEDOT:PSS/TAPC/NPB: organic metal compound (VI) (3~4%)/TmPyPB/LiF/Al.

TABLE 3

|  | measured at a brightness of 1000 Cd/m² | | | measured at a brightness of 1000 Cd/m² | |
| --- | --- | --- | --- | --- | --- |
|  | current efficiency (cd/A) | power efficiency (lm/W) | driving voltage (V) | C.I.E coordinate | maximum luminous intensity peak (nm) |
| organic light-emitting device (VI) | 32.3 | 26.6 | 3.8 | (0.41, 0.58) | 540 |
| organic light-emitting device (VII) | 39.6 | 36.5 | 3.4 | (0.29, 0.62) | 504 |
| organic light-emitting device (VIII) | 26.7 | 21.0 | 4.0 | (0.49, 0.51) | 560 |
| organic light-emitting device (IX) | 35 | 25.9 | 4.3 | (0.39, 0.59) | 528 |

Next, the optical properties (such as maximum emission peak, driving voltage, current efficiency, power efficiency, and C.I.E coordinate) of the light-emitting device (X) were measured by a spectra colorimeter PR650 (purchased from Photo Research Inc.) and a luminance meter LS110 (purchased from Konica Minolta). The results are shown in Table 4.

Example 52: Organic Light-Emitting Device (XI)

A glass substrate with an indium tin oxide (ITO) film with a thickness of 120 nm was provided and then washed with a cleaning agent, acetone, and isopropanol with ultrasonic agitation. After drying with nitrogen flow, the ITO film was subjected to a UV/ozone treatment for 30 min.

Next, PEDOT:PSS (Poly(3,4-ethylenedioxythiophene)-poly(styrenesulfonate)) was coated on the ITO film by a spin coating process (with a rotation rate of 800 rpm for 3 sec and a rotation rate of 2000 rpm for 40 sec) and baked at 130° C. for 40 min to form a PEDOT:PSS film serving as a hole injection layer (with a thickness of 40 nm). Next, TAPC (1,1-bis[4-[N,N'-di(p-tolyl)amino]phenyl]cyclohexane, with a thickness of 40 nm), TCTA (4,4',4'-tri(N-carbazolyl) triphenylamine) doped with Organic metal compound (VII) (the weight ratio between TCTA and Organic metal compound (VII) was 94:6~92:8, with a thickness of 15 nm), TmPyPB (1,3,5-tri(m-pyrid-3-yl-phenyl)benzene, with a thickness of 50 nm), LiF (with a thickness of 0.8 nm), and Al (with a thickness of 120 nm), were subsequently formed on the PEDOT:PSS film at $10^{-6}$ torr, obtaining the organic light-emitting device (XI) after encapsulation. The materials and layers formed therefrom are described in the following: ITO/PEDOT:PSS/TAPC/TCTA:organic metal compound (VII) (6~8%)/TmPyPB/LiF/Al.

Next, the optical properties (such as maximum emission peak, driving voltage, current efficiency, power efficiency, and C.I.E coordinate) of the light-emitting device (XI) were measured by a spectra colorimeter PR650 (purchased from Photo Research Inc.) and a luminance meter LS110 (purchased from Konica Minolta). The results are shown in Table 4.

Example 53: Organic Light-Emitting Device (XII)

A glass substrate with an indium tin oxide (ITO) film with a thickness of 120 nm was provided and then washed with a cleaning agent, acetone, and isopropanol with ultrasonic agitation. After drying with nitrogen flow, the ITO film was subjected to a UV/ozone treatment for 30 min.

Next, PEDOT:PSS (Poly(3,4-ethylenedioxythiophene)-poly(styrenesulfonate)) was coated on the ITO film by a spin coating process (with a rotation rate of 800 rpm for 3 sec and a rotation rate of 2000 rpm for 40 sec) and baked at 130° C. for 40 min to form a PEDOT:PSS film serving as a hole injection layer (with a thickness of 40 nm). Next, TAPC (1,1-bis[4-[N,N'-di(p-tolyl)amino]phenyl]cyclohexane, with a thickness of 40 nm), NPB (N,N'-bis(naphthalen-1-yl)-N,N'-bis(phenyl)-benzidine) doped with Organic metal compound (VIII) (the weight ratio between NPB and Organic metal compound (VIII) was 95:5~94:6, with a thickness of 15 nm), TmPyPB (1,3,5-tri(m-pyrid-3-yl-phenyl)benzene, with a thickness of 50 nm), LiF (with a thickness of 0.8 nm), and Al (with a thickness of 120 nm), were subsequently formed on the PEDOT:PSS film at $10^{-6}$ torr, obtaining the organic light-emitting device (XII) after encapsulation. The materials and layers formed therefrom are described in the following: ITO/PEDOT:PSS/NPB:organic metal compound (VIII) (5~6%)/TmPyPB/LiF/Al.

Next, the optical properties (such as maximum emission peak, driving voltage, current efficiency, power efficiency, and C.I.E coordinate) of the light-emitting device (XII) were measured by a spectra colorimeter PR650 (purchased from Photo Research Inc.) and a luminance meter LS110 (purchased from Konica Minolta). The results are shown in Table 4.

Example 54: Organic Light-Emitting Device (XIII)

A glass substrate with an indium tin oxide (ITO) film with a thickness of 120 nm was provided and then washed with a cleaning agent, acetone, and isopropanol with ultrasonic agitation. After drying with nitrogen flow, the ITO film was subjected to a UV/ozone treatment for 30 min.

Next, PEDOT:PSS (Poly(3,4-ethylenedioxythiophene)-poly(styrenesulfonate)) was coated on the ITO film by a spin coating process (with a rotation rate of 800 rpm for 3 sec and a rotation rate of 2000 rpm for 40 sec) and baked at 130° C. for 40 min to form a PEDOT:PSS film serving as a hole injection layer (with a thickness of 40 nm). Next, TAPC (1,1-bis[4-[N,N'-di(p-tolyl)amino]phenyl]cyclohexane, with a thickness of 40 nm), TCTA (4,4',4'-tri(N-carbazolyl) triphenylamine) doped with Organic metal compound (IX) (the weight ratio between TCTA and Organic metal compound (IX) was 94:6~92:8, with a thickness of 15 nm), TmPyPB (1,3,5-tri(m-pyrid-3-yl-phenyl)benzene, with a thickness of 50 nm), LiF (with a thickness of 0.8 nm), and Al (with a thickness of 120 nm), were subsequently formed on the PEDOT:PSS film at $10^{-6}$ torr, obtaining the organic light-emitting device (XIII) after encapsulation. The materials and layers formed therefrom are described in the following: ITO/PEDOT:PSS/TAPC/TCTA:organic metal compound (IX) (6~8%)/TmPyPB/LiF/Al.

Next, the optical properties (such as maximum emission peak, driving voltage, current efficiency, power efficiency, and C.I.E coordinate) of the light-emitting device (XIII) were measured by a spectra colorimeter PR650 (purchased from Photo Research Inc.) and a luminance meter LS110 (purchased from Konica Minolta). The results are shown in Table 4.

Example 55: Organic Light-Emitting Device (XIV)

Example 55 was performed in the same manner as in Example 47 except that Organic metal compound (XXIII) was substituted for Organic metal compound (I), obtaining the organic light-emitting device (XIV). The materials and layers formed therefrom are described in the following: ITO/PEDOT:PSS/TAPC/TCTA:Organic metal compound (XIV) (6-8%)/TmPyPB/LiF/Al Next, the optical properties (such as maximum emission peak, driving voltage, current efficiency, power efficiency, and C.I.E coordinate) of the light-emitting device (XIV) were measured by a spectra colorimeter PR650 (purchased from Photo Research Inc.) and a luminance meter LS110 (purchased from Konica Minolta). The results are shown in Table 4.

Example 56: Organic Light-Emitting Device (XV)

Example 56 was performed in the same manner as in Example 47 except that Organic metal compound (XXVIII) was substituted for Organic metal compound (I), obtaining the organic light-emitting device (XV). The materials and layers formed therefrom are described in the following: ITO/PEDOT:PSS/TAPC/TCTA:Organic metal compound (XXVIII) (4-6%)/TmPyPB/LiF/Al Next, the optical properties (such as maximum emission peak, driving voltage, current efficiency, power efficiency, and C.I.E coordinate) of the light-emitting device (XV) were measured by a spectra colorimeter PR650 (purchased from Photo Research Inc.) and a luminance meter LS110 (purchased from Konica Minolta). The results are shown in Table 4.

Example 57: Organic Light-Emitting Device (XVI)

Example 57 was performed in the same manner as in Example 47 except that Organic metal compound (XXXVII) was substituted for Organic metal compound (I), obtaining the organic light-emitting device (XVI). The materials and layers formed therefrom are described in the following: ITO/PEDOT:PSS/TAPC/TCTA:Organic metal compound (XXXVII) (6-8%)/TmPyPB/LiF/Al Next, the optical properties (such as maximum emission peak, driving voltage, current efficiency, power efficiency, and C.I.E coordinate) of the light-emitting device (XVI) were measured by a spectra colorimeter PR650 (purchased from Photo Research Inc.) and a luminance meter LS110 (purchased from Konica Minolta). The results are shown in Table 4.

Example 58: Organic Light-Emitting Device (XVII)

Example 58 was performed in the same manner as in Example 47 except that Organic metal compound (XLII) was substituted for Organic metal compound (I), obtaining the organic light-emitting device (XVII). The materials and layers formed therefrom are described in the following: ITO/PEDOT:PSS/TAPC/TCTA:Organic metal compound (XLII) (2-6%)/TmPyPB/LiF/Al Next, the optical properties (such as maximum emission peak, driving voltage, current efficiency, power efficiency, and C.I.E coordinate) of the light-emitting device (XVII) were measured by a spectra colorimeter PR650 (purchased from Photo Research Inc.) and a luminance meter LS110 (purchased from Konica Minolta). The results are shown in Table 4.

Example 59: Organic Light-Emitting Device (XVIII)

Example 59 was performed in the same manner as in Example 47 except that Organic metal compound (XLIII) was substituted for Organic metal compound (I), obtaining the organic light-emitting device (XVIII). The materials and layers formed therefrom are described in the following: ITO/PEDOT:PSS/TAPC/TCTA:Organic metal compound (XLIII) (2-4%)/TmPyPB/LiF/Al Next, the optical properties (such as maximum emission peak, driving voltage, current efficiency, power efficiency, and C.I.E coordinate) of the light-emitting device (XVIII) were measured by a spectra colorimeter PR650 (purchased from Photo Research Inc.) and a luminance meter LS110 (purchased from Konica Minolta). The results are shown in Table 4.

Example 60: Organic Light-Emitting Device (XIX)

Example 60 was performed in the same manner as in Example 47 except that Organic metal compound (XX) was substituted for Organic metal compound (I), obtaining the organic light-emitting device (XIX). The materials and layers formed therefrom are described in the following: ITO/PEDOT:PSS/TAPC/TCTA:Organic metal compound (XX) (2-8%)/TmPyPB/LiF/Al Next, the optical properties (such as maximum emission peak, driving voltage, current efficiency, power efficiency, and C.I.E coordinate) of the light-emitting device (XIX) were measured by a spectra colorimeter PR650 (purchased from Photo Research Inc.) and a luminance meter LS110 (purchased from Konica Minolta). The results are shown in Table 4.

TABLE 4

|  | measured at a brightness of 1000 Cd/m$^2$ | | | | measured at a brightness of 1000 Cd/m$^2$ |
| --- | --- | --- | --- | --- | --- |
|  | current efficiency (cd/A) | power efficiency (lm/W) | driving voltage (V) | C.I.E coordinate | maximum luminous intensity peak (nm) |
| organic light-emitting device (X) | 44.8 | 39.2 | 3.6 | (0.51, 0.46) | 580 |
| organic light-emitting device (XI) | 86.6 | 73.8 | 3.7 | (0.28, 0.61) | 500 |
| organic light-emitting device (XII) | 64.0 | 53.8 | 3.7 | (0.42, 0.56) | 544 |
| organic light-emitting device (XIII) | 86.6 | 68.3 | 4.1 | (0.41, 0.58) | 540 |
| organic light-emitting device (XIV) | 62.5 | 51.6 | 3.8 | (0.32, 0.62) | 520 |
| organic light-emitting device (XV) | 69.1 | 58.6 | 3.7 | (0.29, 0.61) | 506 |
| organic light-emitting device (XVI) | 77.4 | 62.3 | 3.9 | (0.40, 0.59) | 534 |
| organic light-emitting device (XVII) | 71.8 | 59.3 | 3.8 | (0.48, 0.51) | 563 |
| organic light-emitting device (XVIII) | 9.6 | 8.0 | 3.8 | (0.65, 0.34) | 620 |
| organic light-emitting device (XIX) | 50.7 | 40.8 | 3.9 | (0.40, 0.60) | 534 |

As shown in Table 4, during the formation of the light-emitting devices (X)-(XIII) via a dry process, it shows that the organic light-emitting device employing the organic metal compound having the structure of Formula (I) exhibits high luminous efficiency. Furthermore, the organic light-emitting device (XI) fabricated via the dry process has a current efficiency of 86.6 cd/A and a power efficiency of 73.8 lm/W.

It will be clear that various modifications and variations can be made to the disclosed methods and materials. It is intended that the specification and examples be considered as exemplary only, with the true scope of the disclosure being indicated by the following claims and their equivalents.

What is claimed is:

1. An organic metal compound, having a structure of Formula (I) or Formula (II):

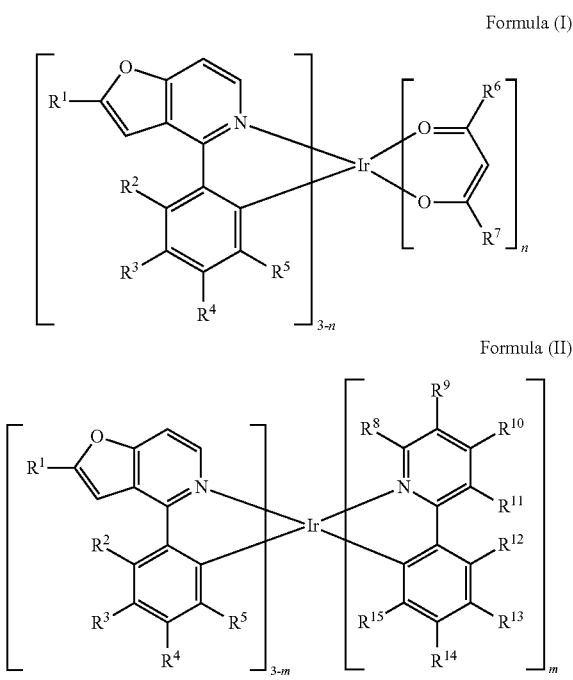

wherein, $R^1$ is independently hydrogen, $C_{1-12}$ alkyl group, $C_{1-12}$ alkoxy group, amine, $C_{2-6}$ alkenyl group, $C_{2-6}$ alkynyl group, $C_{5-10}$ cycloalkyl group, $C_{3-12}$ heteroaryl group, or $C_{6-12}$ aryl group; $R^2$, $R^3$, $R^4$, and $R^5$ are independently hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group; $R^6$ and $R^7$ are independent $C_{1-6}$ alkyl group, or phenyl group; $R^8$, $R^9$, $R^{10}$, and $R^{11}$ are independently hydrogen, halogen, $C_{1-12}$ alkyl group, $C_{1-12}$ fluoroalkyl group, or two adjacent groups of $R^8$, $R^9$, $R^{10}$, and $R^{11}$ are optionally combined with the carbon atoms which they are attached to, to form a cycloalkyl group, or aryl group; $R^{12}$, $R^{13}$, $R^{14}$, and $R^{15}$ are independently hydrogen, halogen, $C_{1-12}$ alkyl group, $C_{1-12}$ fluoroalkyl group, or two adjacent groups of $R^{12}$, $R^{13}$, $R^{14}$, and $R^{15}$ are optionally combined with the carbon atoms which they are attached to, to form a cycloalkyl group, or aryl group; m is 1 or 2; and, n is 0 or 1.

2. The organic metal compound as claimed in claim 1, wherein each $R^1$ is independently hydrogen, methyl group, ethyl group, propyl group, isopropyl group, n-butyl group, isobutyl group, tert-butyl group, pentyl group, hexyl group, cyclohexyl group, phenyl group, biphenyl group, or naphthyl group.

3. The organic metal compound as claimed in claim 1, wherein $R^2$, $R^3$, $R^4$, and $R^5$ are independently hydrogen, fluorine, methyl group, ethyl group, propyl group, isopropyl group, n-butyl group, isobutyl group, tert-butyl group, pentyl group, hexyl group, fluoromethyl, fluoroethyl, methoxy, ethoxy, propoxy, or isopropoxy, or $R^3$ and $R^4$ are combined with the carbon atoms which they are attached to, to form a phenyl group.

4. The organic metal compound as claimed in claim 1, wherein at least one of $R^1$, $R^2$, $R^3$, $R^4$, and $R^5$ is not hydrogen.

5. The organic metal compound as claimed in claim 1, wherein $R^6$ and $R^7$ are independently methyl group, ethyl group, propyl group, isopropyl group, n-butyl group, isobutyl group, tert-butyl group, pentyl group, hexyl group, or phenyl group.

6. The organic metal compound as claimed in claim 1, wherein $R^8$, $R^9$, $R^{10}$, and $R^{11}$ are independently hydrogen, fluorine, methyl group, ethyl group, propyl group, isopropyl group, n-butyl group, isobutyl group, tert-butyl group, pentyl group, hexyl group, fluoromethyl, or fluoroethyl, or $R^9$ and $R^{10}$ are combined with the carbon atoms which they are attached to, to form a phenyl group, and/or $R^{10}$ and $R^{11}$ are combined with the carbon atoms which they are attached to, to form a phenyl group.

7. The organic metal compound as claimed in claim 1, wherein $R^{12}$, $R^{13}$, $R^{14}$, and $R^{15}$ are independently hydrogen, fluorine, methyl group, ethyl group, propyl group, isopropyl group, n-butyl group, isobutyl group, tert-butyl group, pentyl group, hexyl group, fluoromethyl, or fluoroethyl, or $R^{12}$ and $R^{13}$ are combined with the carbon atoms which they are attached to, to form a phenyl group, and/or $R^{13}$ and $R^{14}$ are combined with the carbon atoms which they are attached to, to form a phenyl group.

8. The organic metal compound as claimed in claim 1, wherein the organic metal compound is

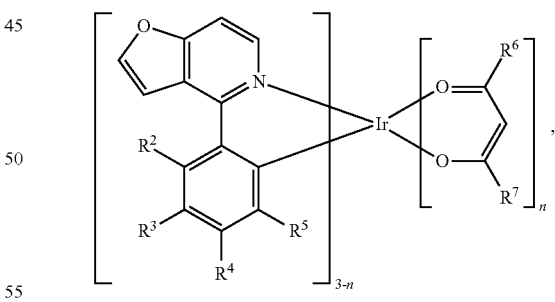

$R^2$, $R^3$, $R^4$, and $R^5$ are independently hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group; $R^6$ and $R^7$ are independent $C_{1-6}$ alkyl group, or phenyl group; and, n is 0 or 1.

9. The organic metal compound as claimed in claim 8, wherein at least one of $R^2$, $R^3$, $R^4$, and $R^5$ is not hydrogen.

10. The organic metal compound as claimed in claim 1, wherein the organic metal compound is

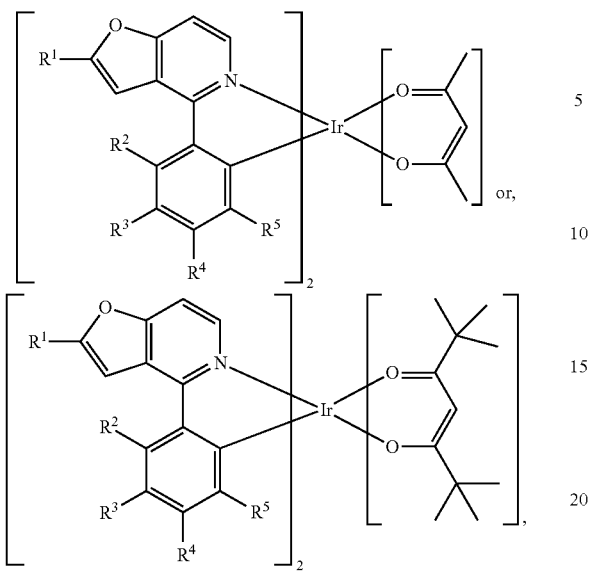

R¹ is independently hydrogen, $C_{1-12}$ alkyl group, $C_{1-12}$ alkoxy group, amine, $C_{2-6}$ alkenyl group, $C_{2-6}$ alkynyl group, $C_{5-10}$ cycloalkyl group, $C_{3-12}$ heteroaryl group, or $C_{6-12}$ aryl group; and, $R^2$, $R^3$, $R^4$, and $R^5$ are independently hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group.

11. The organic metal compound as claimed in claim 1, wherein the organic metal compound is

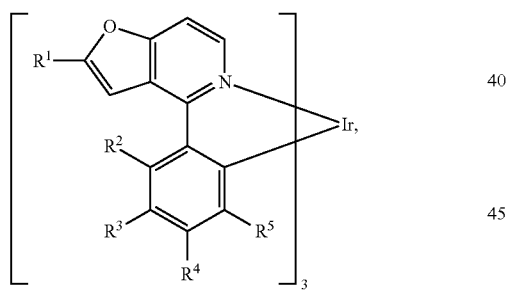

R¹ is independently hydrogen, $C_{1-12}$ alkyl group, $C_{1-12}$ alkoxy group, amine, $C_{2-6}$ alkenyl group, $C_{2-6}$ alkynyl group, $C_{5-10}$ cycloalkyl group, $C_{3-12}$ heteroaryl group, or $C_{6-12}$ aryl group; and, $R^2$, $R^3$, $R^4$, and $R^5$ are independently hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group.

12. The organic metal compound as claimed in claim 1, wherein R¹ is independently hydrogen, or $C_{1-12}$ alkyl group; $R^2$, $R^3$, $R^4$, and $R^5$ are independently hydrogen, halogen, $C_{1-12}$ alkyl group, $C_{1-12}$ alkoxy group, or two adjacent groups of $R^2$, $R^3$, $R^4$, and $R^5$ are optionally combined with the carbon atoms which they are attached to, to form an aryl group; and $R^6$ and $R^7$ are independent $C_{1-6}$ alkyl group.

13. The organic metal compound as claimed in claim 1, wherein the organic metal compound is

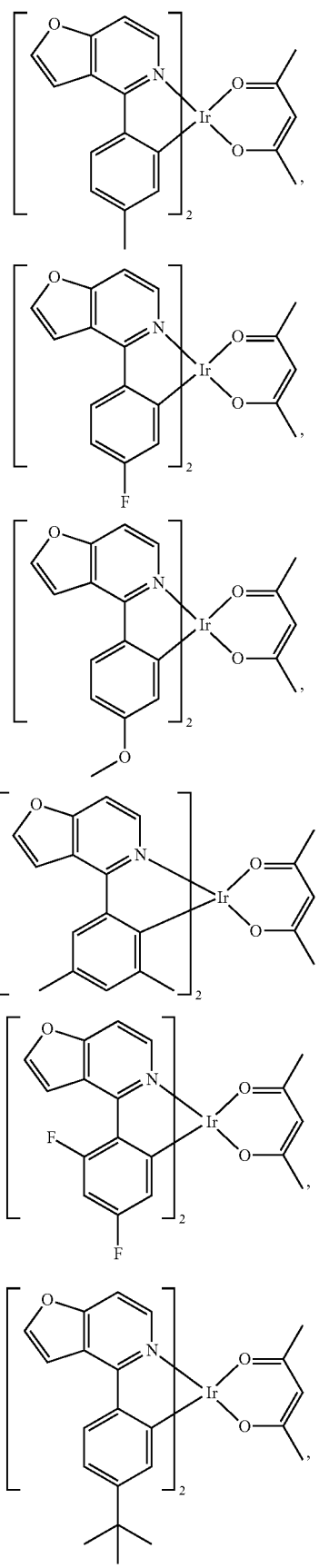

103
-continued
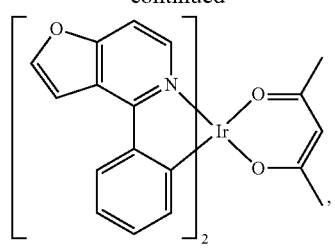
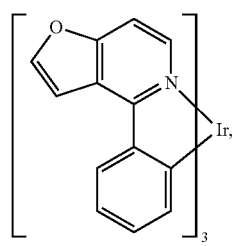
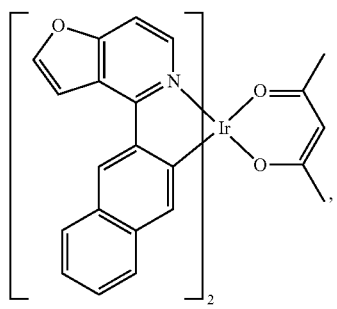
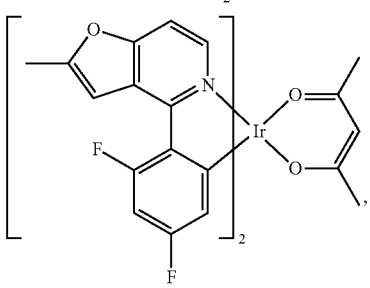
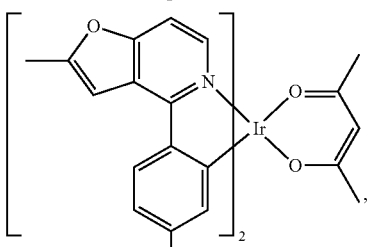
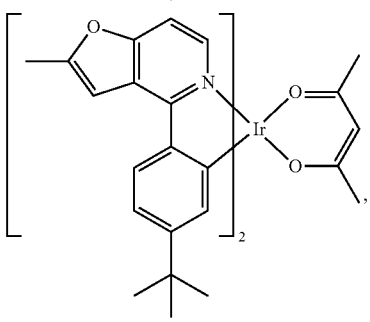
104
-continued
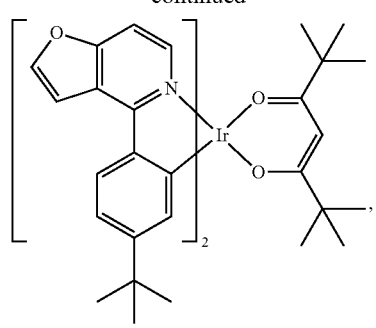
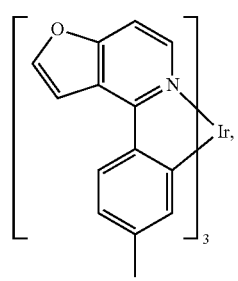
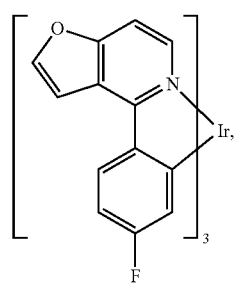
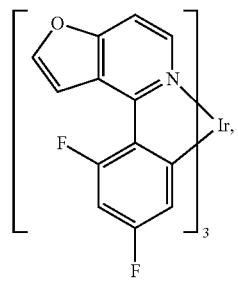
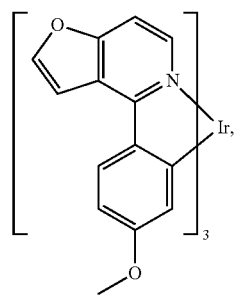

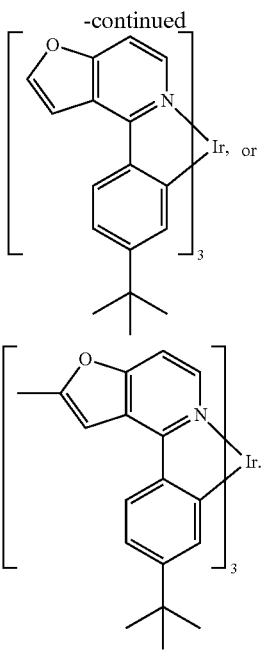

14. The organic metal compound as claimed in claim 1, wherein the organic metal compound is

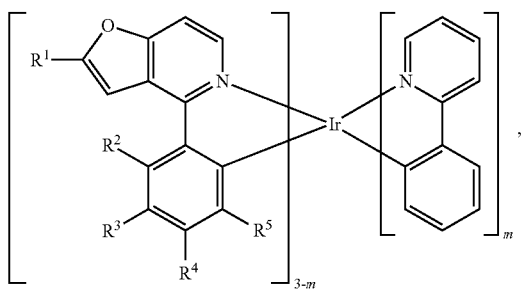

$R^1$ is independently hydrogen, $C_{1-12}$ alkyl group, $C_{1-12}$ alkoxy group, amine, $C_{2-6}$ alkenyl group, $C_{2-6}$ alkynyl group, $C_{5-10}$ cycloalkyl group, $C_{3-12}$ heteroaryl group, or $C_{6-12}$ aryl group; $R^2$, $R^3$, $R^4$, and $R^5$ are independently hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group; and, m is 1 or 2.

15. The organic metal compound as claimed in claim 1, wherein the organic metal compound is

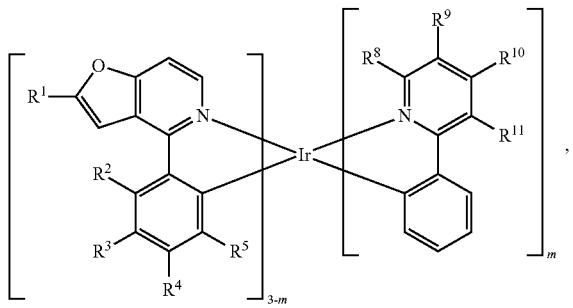

$R^1$ is independently hydrogen, $C_{1-12}$ alkyl group, $C_{1-12}$ alkoxy group, amine, $C_{2-6}$ alkenyl group, $C_{2-6}$ alkynyl group, $C_{5-10}$ cycloalkyl group, $C_{3-12}$ heteroaryl group, or $C_{6-12}$ aryl group; $R^2$, $R^3$, $R^4$, and $R^5$ are independently hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group; $R^8$, $R^9$, $R^{10}$, and $R^{11}$ are independently hydrogen, halogen, $C_{1-12}$ alkyl group, $C_{1-12}$ fluoroalkyl group, or two adjacent groups of $R^8$, $R^9$, $R^{10}$, and $R^{11}$ are optionally combined with the carbon atoms which they are attached to, to form a cycloalkyl group, or aryl group; and, m is 1 or 2.

16. The organic metal compound as claimed in claim 1, wherein the organic metal compound is

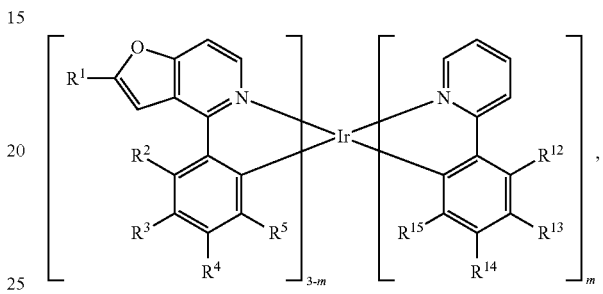

$R^1$ is independently hydrogen, $C_{1-12}$ alkyl group, $C_{1-12}$ alkoxy group, amine, $C_{2-6}$ alkenyl group, $C_{2-6}$ alkynyl group, $C_{5-10}$ cycloalkyl group, $C_{3-12}$ heteroaryl group, or $C_{6-12}$ aryl group; $R^2$, $R^3$, $R^4$, and $R^5$ are independently hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group; $R^{12}$, $R^{13}$, $R^{14}$, and $R^{15}$ are independently hydrogen, halogen, $C_{1-12}$ alkyl group, $C_{1-12}$ fluoroalkyl group, or two adjacent groups of $R^{12}$, $R^{13}$, $R^{14}$, and $R^{15}$ are optionally combined with the carbon atoms which they are attached to, to form a cycloalkyl group, or aryl group; and, m is 1 or 2.

17. The organic metal compound as claimed in claim 1, wherein the organic metal compound is

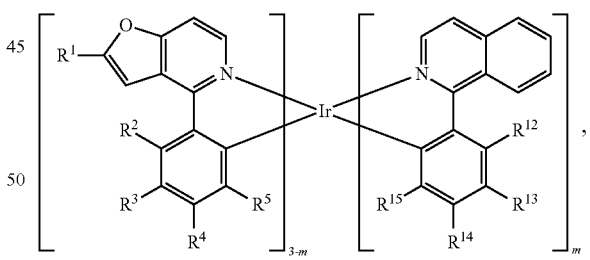

$R^1$ is independently hydrogen, $C_{1-12}$ alkyl group, $C_{1-12}$ alkoxy group, amine, $C_{2-6}$ alkenyl group, $C_{2-6}$ alkynyl group, $C_{5-10}$ cycloalkyl group, $C_{3-12}$ heteroaryl group, or $C_{6-12}$ aryl group; $R^2$, $R^3$, $R^4$, and $R^5$ are independently hydrogen, halogen, $C_{1-12}$ alkyl group, $C_{1-12}$ alkoxy group, $C_{1-12}$ fluoroalkyl group, or two adjacent groups of $R^2$, $R^3$, $R^4$, and $R^5$ are optionally combined with the carbon atoms which they are attached to, to form a cycloalkyl group, or aryl group; $R^{12}$, $R^{13}$, $R^{14}$, and $R^{15}$ are independently hydrogen, halogen, $C_{1-12}$ alkyl group, $C_{1-12}$ fluoroalkyl group, or two adjacent groups of $R^{12}$, $R^{13}$, $R^{14}$, and $R^{15}$ are optionally combined with the carbon atoms which they are attached to, to form a cycloalkyl group, or aryl group; and, m is 1 or 2.

18. The organic metal compound as claimed in claim 1, wherein $R^1$ is independently hydrogen, or $C_{1-12}$ alkyl group; $R^2$, $R^3$, $R^4$, and $R^5$ are independently hydrogen, halogen, $C_{1-12}$ alkyl group, $C_{1-12}$ alkoxy group, or two adjacent groups of $R^2$, $R^3$, $R^4$, and $R^5$ are optionally combined with the carbon atoms which they are attached to, to form an aryl group; $R^8$, $R^9$, $R^{10}$, and $R^{11}$ are independently hydrogen, $C_{1-12}$ alkyl group, or two adjacent groups of $R^8$, $R^9$, $R^{10}$, and $R^{11}$ are optionally combined with the carbon atoms which they are attached to, to form an aryl group; and $R^{12}$, $R^{13}$, $R^{14}$, and $R^{15}$ are independently hydrogen, or $C_{1-12}$ alkyl group.

19. The organic metal compound as claimed in claim 1, wherein the organic metal compound is

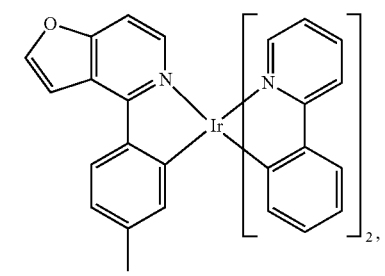

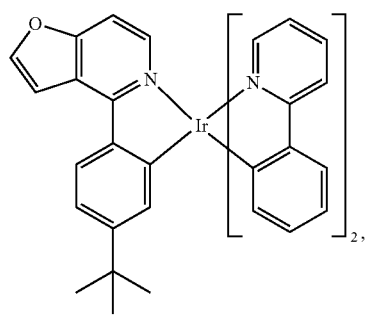

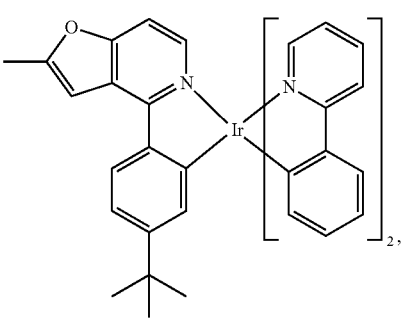

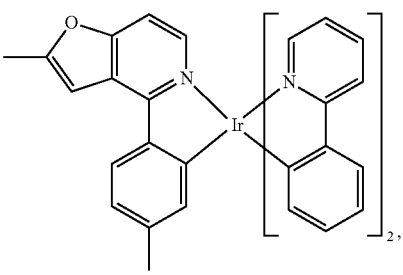

-continued

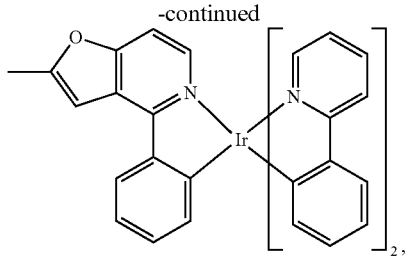

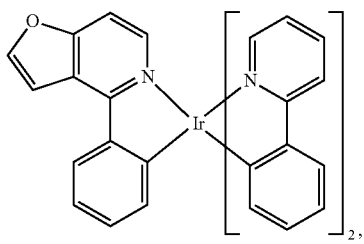

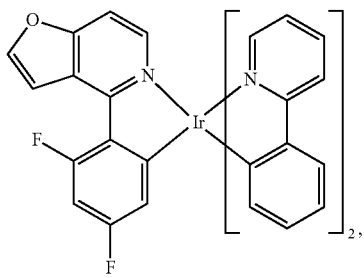

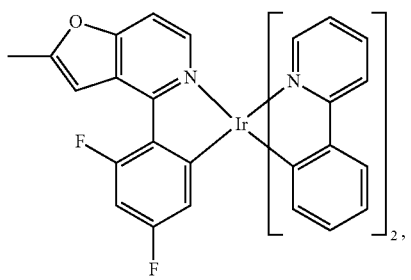

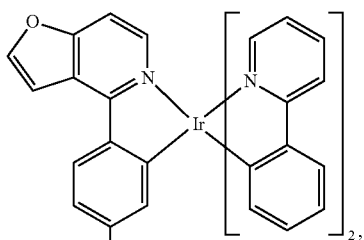

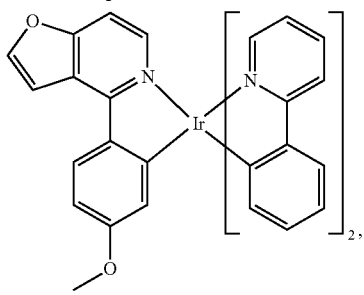

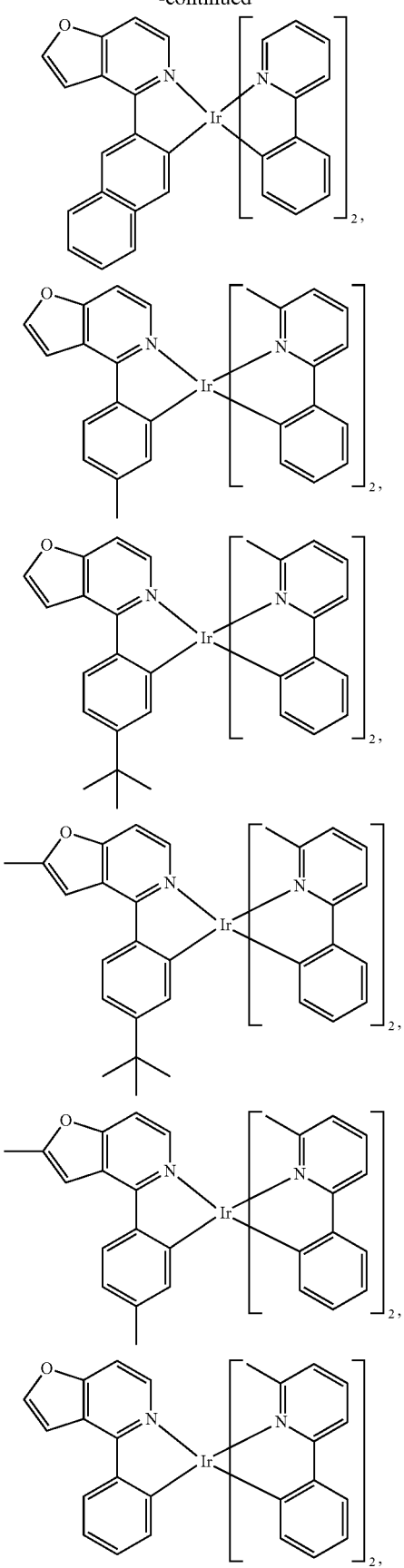
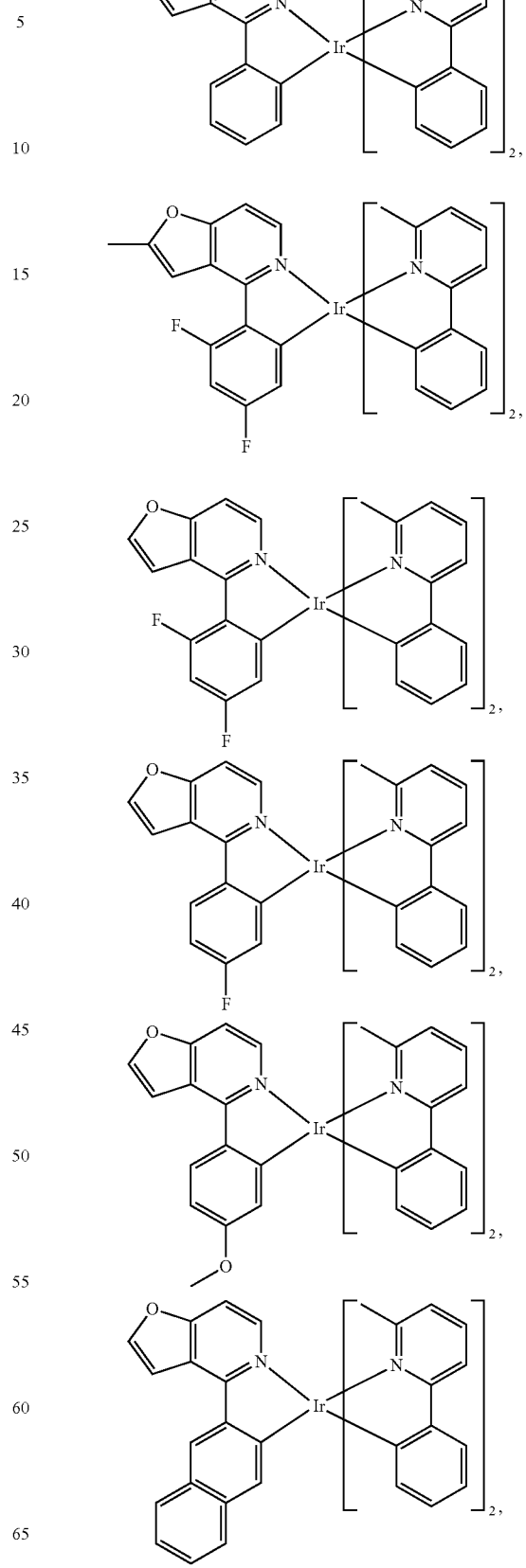

111
-continued
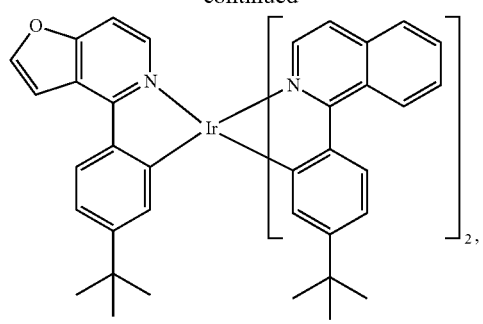
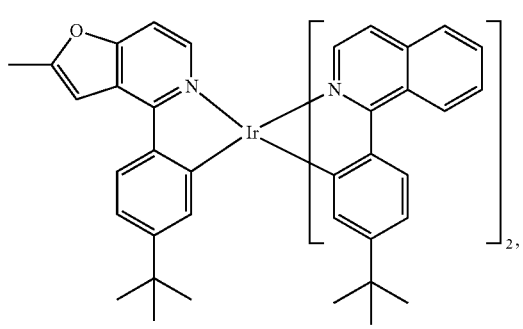
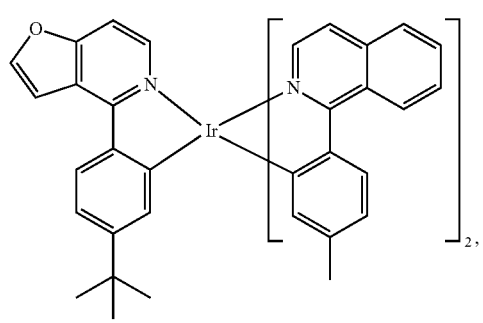
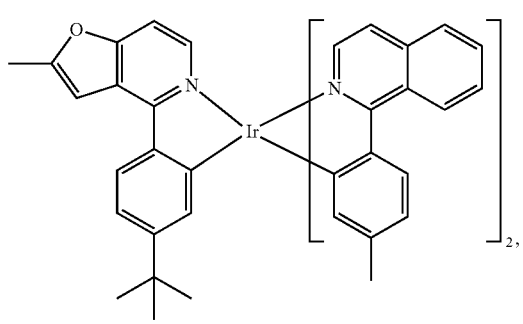
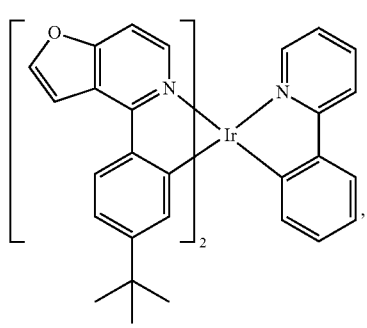
112
-continued
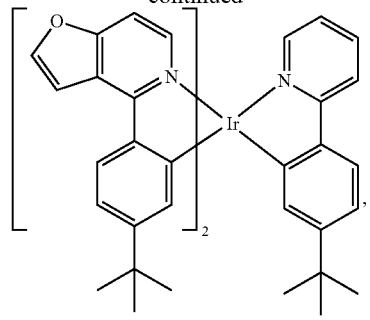
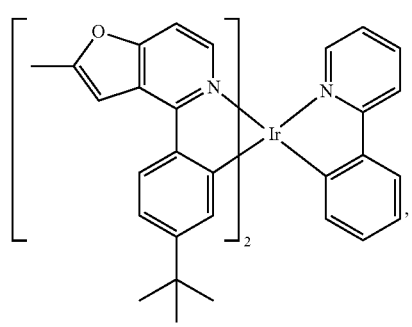
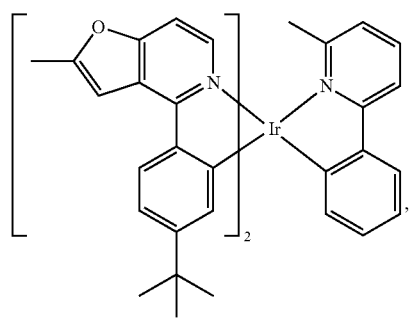
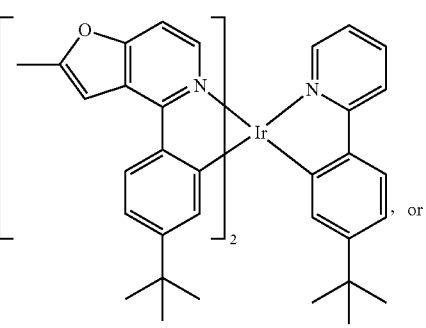, or
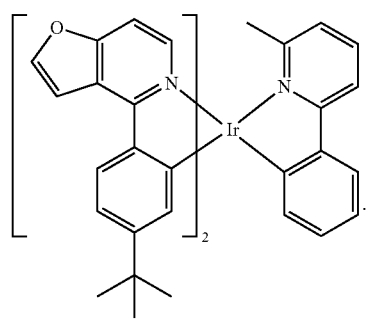.

20. An organic light-emitting device, comprising:
a pair of electrodes; and
an organic light-emitting element, disposed between the electrodes, wherein the organic light-emitting element comprises the organic metal compound as claimed in claim 1.

* * * * *